US012788790B2

(12) United States Patent
Quintana et al.

(10) Patent No.: US 12,788,790 B2
(45) Date of Patent: Nov. 10, 2026

(54) COMPOSITIONS AND USES FOR ENGINEERED THERAPEUTIC MICROBES AND ASSOCIATED RECEPTORS

(71) Applicants: The Brigham and Women's Hospital, Inc., Boston, MA (US); THE GOVERNING COUNCIL OF THE UNIVERSITY OF TORONTO, Toronto (CA)

(72) Inventors: Francisco J. Quintana, Jamaica Plain, MA (US); Benjamin M. Scott, Stratford (CA); Sergio G. Peisajovich, San Diego, CA (US); Belinda S. W. Chang, Toronto (CA)

(73) Assignees: The Brigham and Women's Hospital, Inc., Boston, MA (US); The Governing Council of the University of Toronto, Toronto (CA)

( * ) Notice: Subject to any disclaimer, the term of this patent is extended or adjusted under 35 U.S.C. 154(b) by 1054 days.

(21) Appl. No.: 17/637,771

(22) PCT Filed: Aug. 26, 2020

(86) PCT No.: PCT/US2020/048049

§ 371 (c)(1),
(2) Date: Feb. 23, 2022

(87) PCT Pub. No.: WO2021/041575

PCT Pub. Date: Mar. 4, 2021

(65) Prior Publication Data

US 2022/0323521 A1 Oct. 13, 2022

Related U.S. Application Data

(60) Provisional application No. 62/891,603, filed on Aug. 26, 2019.

(51) Int. Cl.

| | |
|---|---|
| ***A61K 36/064*** | (2006.01) |
| ***A61P 37/06*** | (2006.01) |
| ***C07K 14/47*** | (2006.01) |
| ***C07K 14/54*** | (2006.01) |
| ***C07K 14/55*** | (2006.01) |
| ***C07K 14/565*** | (2006.01) |
| ***C07K 14/72*** | (2006.01) |
| ***C12N 9/14*** | (2006.01) |

(52) U.S. Cl.

CPC ............ *A61K 36/064* (2013.01); *A61P 37/06* (2018.01); *C07K 14/4702* (2013.01); *C07K 14/54* (2013.01); *C07K 14/55* (2013.01); *C07K 14/565* (2013.01); *C07K 14/723* (2013.01); *C12N 9/14* (2013.01); *C12Y 306/01005* (2013.01); *C07K 2319/02* (2013.01); *C07K 2319/055* (2013.01)

(58) Field of Classification Search

CPC ... A61K 36/064; A61P 37/06; C07K 14/4702; C12N 9/14

See application file for complete search history.

(56) References Cited

U.S. PATENT DOCUMENTS

| | | | |
|---|---|---|---|
| 3,843,800 | A | 10/1974 | Langejan |
| 3,993,783 | A | 11/1976 | Langejan |
| 4,217,420 | A | 8/1980 | Langejan |
| 4,341,871 | A | 7/1982 | Langejan et al. |
| 4,764,472 | A | 8/1988 | Pomper et al. |
| 5,509,447 | A | 4/1996 | Kane et al. |
| 6,033,887 | A | 3/2000 | Charpentier |
| 6,372,481 | B1 | 4/2002 | Wada et al. |
| 2005/0106287 | A1 | 5/2005 | Groen et al. |
| 2005/0129808 | A1 | 6/2005 | Koster et al. |
| 2010/0092611 | A1 | 4/2010 | Degre et al. |
| 2019/0022197 | A1 | 1/2019 | Bellgrau et al. |

FOREIGN PATENT DOCUMENTS

| | | | |
|---|---|---|---|
| CN | 102803468 | A | 11/2012 |
| EP | 0616030 | A1 | 9/1994 |
| EP | 1931762 | B1 | 12/2012 |
| JP | 2001-516587 | A | 10/2001 |
| JP | 2010536360 | A | 12/2010 |

(Continued)

OTHER PUBLICATIONS

Gomes et al., Comparison of Yeasts as Hosts for Recombinant Protein Production. Microorganisms. 2018; 6: 38, p. 1-23. (Year: 2018).*

(Continued)

*Primary Examiner* — James D Schultz
*Assistant Examiner* — Jianjian Zhu
(74) *Attorney, Agent, or Firm* — Fish & Richardson P.C.

(57) ABSTRACT

Described herein are microbial probiotics that, in response to metabolite extracellular ATP (eATP) produced in the microenvironment of inflamed tissues detected, e.g., via an engineered mammalian P2Y2 receptor, secrete an anti-inflammatory protein, e.g., IL-2, IL-10, or the CD39-like eATP-degrading enzyme apyrase. Thus, provided herein is an isolated *Saccharomyces* cell (or cells, e.g., a population of such cells) that has been engineered to express one, two, or all three exogenous proteins selected from: (I) a mammalian P2Y purinoceptor 2 (P2Y2) protein, preferably human P2Y2; 15 (ii) a mutant Gpal protein comprising at least 5 C-terminal residues from a mammalian G alpha, preferably Gai3, wherein the mutant Gpal protein couples the P2Y2 protein to the yeast mating pathway; and (iii) an anti-inflammatory protein.

30 Claims, 43 Drawing Sheets

Specification includes a Sequence Listing.

(56) References Cited

FOREIGN PATENT DOCUMENTS

| | | | |
|---|---|---|---|
| RU | 2444566 C2 | 3/2012 |
| WO | WO 1985/002200 | 5/1985 |
| WO | WO 1999/055901 | 11/1999 |
| WO | WO 2005/100990 | 10/2005 |
| WO | WO 2007/039586 | 4/2007 |
| WO | WO 2009/130219 | 10/2009 |

OTHER PUBLICATIONS

Spiller et al., Randomized double blind placebo-controlled trial of *Saccharomyces cerevisiae* CNCM I-3856 in irritable bowel syndrome: improvement in abdominal pain and bloating in those with predominant constipation. United European Gastroenterology Journal. 2016; 4(3): 353-362. (Year: 2016).*

Andrews et al., "Interleukin-27 as a novel therapy for inflammatory bowel disease: a critical review of the literature," Inflammatory Bowel Diseases, Sep. 1, 2016, 22(9):2255-64.

Atarashi et al., "ATP drives lamina propria TH17 cell differentiation," Nature, Oct. 2008, 455(7214):808-12.

Babicki et al., "Heatmapper: web-enabled heat mapping for all, " Nucleic Acids Research, Jul. 8, 2016, 44(W1):W147-53.

Ballesteros et al., "[19] Integrated methods for the construction of three-dimensional models and computational probing of structure-function relations in G protein-coupled receptorse," Methods in Neurosciences, Jan. 1995, 366-428.

Bashor et al., "Complex signal processing in synthetic gene circuits using cooperative regulatory assemblies, " Science, May 10, 2019, 364(6440):593-7.

Bashor et al., "Rewiring cells: synthetic biology as a tool to interrogate the organizational principles of living systems," Annual Review of Biophysics, Jun. 6, 2010, 39:515-37.

Bashor et al., "Using engineered scaffold interactions to reshape MAP kinase pathway signaling dynamics," Science, Mar. 14, 2008, 319(5869):1539-43.

Berer et al., "Commensal microbiota and myelin autoantigen cooperate to trigger autoimmune demyelination," Nature, Nov. 2011, 479(7374):538-41.

Bernstein, "Treatment of IBD: where we are and where we are going. Official journal of the American College of Gastroenterologyl," ACG, Jan. 1, 2015, 110(1):114-26.

Blander et al., "Regulation of inflammation by microbiota interactions with the host," Nature Immunology, Aug. 2017, 18(8):851-60.

Bours et al., "P2 receptors and extracellular ATP: a novel homeostatic pathway in inflammation," Frontiers in Bioscience-Scholar, Jun. 1, 2011, 3(4):1443-56.

Braat et al., "A phase I trial with transgenic bacteria expressing interleukin-10 in Crohn's disease," Clinical Gastroenterology and Hepatology, Jun. 1, 2006, 4(6):754-9.

Brown et al., "Functional coupling of mammalian receptors to the yeast mating pathway using novel yeast/mammalian G protein α-subunit chimeras," Yeast, Jan. 15, 2000, 16(1):11-22.

Burnstock et al., "Purinergic signalling and immune cells," Purinergic Signalling, Dec. 2014, 10(4):529-64.

Caporaso et al., "QUIME allows analysis of high-throughput community sequencing data, " Nature Methods, May 2010, 7(5):335-6.

Cauwels et al., "Extracellular ATP drives systemic inflammation, tissue damage and mortality, " Cell Death & Disease, Mar. 2014, 5(3):e1102, 7 pages.

Cekic et al., "Purinergic regulation of the immune system," Nature Reviews Immunology, Mar. 2016, 16(3):177-92.

Cervantes-Barragan et al., "Lactobacillus reuteri induces gut intraepithelial CD4+ CD8αα+ T cells," Science, Aug. 25, 2017, 357(6353):806-10.

Chen et al., "Synthetic biology toolkits and applications in *Saccharomyces cerevisiae*," Biotechnology Advances, Nov. 15, 2018, 36(7):1870-81.

Chu et al., "Gene-microbiota interactions contribute to the pathogenesis of inflammatory bowel disease," Science, May 27, 2016, 352(6289):1116-20.

Cox et al., "Calorie restriction slows age-related microbiota changes in an Alzheimer's disease model in female mice," Scientific Reports, Nov. 29, 2019, 9(1), 14 pages.

Deaglio et al., "Adenosine generation catalyzed by CD39 and CD73 expressed on regulatory T cells mediates immune suppression," The Journal of Experimental Medicine, Jun. 11, 2007, 204(6):1257-65.

Di Roberto et al., "Evolution of a G protein-coupled receptor response by mutations in regulatory network interactions," Nature Communications, Aug. 4, 2016, 7(1):1-1.

Di Roberto et al., "Directed evolution methods to rewire signaling networks," Synthetic Protein Switches, vol. 2017, 321-37.

Di Virgilio et al., "Assessing extracellular ATP as danger signal in vivo: the pmeLuc system, " NLR Proteins 2016, 115-29.

Donaldson et al., "Gut microbiota utilize immunoglobulin A for mucosal colonization," Science, May 18, 2018, 360(6390):795-800.

Dong et al., "Directed molecular evolution of DREADDs: a generic approach to creating next-generation RASSLs," Nature Protocols, Mar. 2010, 5(3):561-73.

Durmusoglu et al., "Establishing Probiotic *Saccharomyces boulardii* as a Model Organism for Synthesis and Delivery of Biomolecules," bioRxiv, Jan. 2020, retrieved Oct. 6, 2022 from URL <https://www.biorxiv.org/content/biorxiv/early/2020/23/2020.01.22.915389.full.pdf>, 56 pages.

Enaud et al., "The mycobiome: a neglected component in the microbiota-gut-brain axis, " Microorganisms, Mar. 2018, 6(1):22.

Fichtner-Feigl et al., "Induction of IL-13 triggers TGF-β1-dependent tissue fibrosis in chronic 2, 4, 6-trinitrobenzene sulfonic acid colitis," The Journal of Immunology, May 1, 2007, 178(9):5859-70.

Ford et al., "Opportunistic infections with anti-tumor necrosis factor-α therapy in inflammatory bowel disease: meta-analysis of randomized controlled trials," Official journal of the American College of Gastroenterologyl ACG, Aug. 2013, 108(8):1268-76.

Frank et al., "Molecular-phylogenetic characterization of microbial community imbalances in human inflammatory bowel diseases," Proceedings of the National Academy of Sciences, Aug. 21, 2007,104(34):13780-5.

Friedman et al., "CD39 deletion exacerbates experimental murine colitis and human polymorphisms increase susceptibility to inflammatory bowel disease," Proceedings of the National Academy of Sciences, Sep. 29, 2009, 106(39):16788-93.

Garrett et al., "Homeostasis and inflammation in the intestine," Cell, Mar. 19, 2010, 140(6):859-70.

Gevers et al., "The treatment-naive microbiome in new-onset Crohn's disease," Cell Host & Microbe, Mar. 12, 2014, 15(3):382-92.

Gibson et al., "Heightened expression of CD39 by regulatory T lymphocytes is associated with therapeutic remission in inflammatory bowel disease," Inflammatory Bowel Diseases, Dec. 1, 2015, 21(12):2806-14.

Goettel et al., "AHR activation is protective against colitis driven by T cells in humanized mice," Cell Reports, Oct. 25, 2016, 17(5):1318-29.

Goettel et al., "Low-dose interleukin-2 ameliorates colitis in a preclinical humanized mouse model," Cellular and Molecular Gastroenterology and Hepatology, 2019, 8(2):193, 3 pages.

Grootjans et al., "Epithelial endoplasmic reticulum stress orchestrates a protective IgA response," Science, Mar. 1, 2019, 363(6430):993-8.

Gulbransen et al., "Activation of neuronal P2X7 receptor-pannexin-1 mediates death of enteric neurons during colitis," Nature Medicine, Apr. 2012, 18(4):600-4.

Gurung et al., "Chronic TLR stimulation controls NLRP3 inflammasome activation through IL-10 mediated regulation of NLRP3 expression and caspase-8 activation," Scientific Reports, Sep. 28, 2015, 5(1):1-0.

Hasty et al., "Engineered gene circuits," Nature, Nov. 2002, 420(6912):224-30.

He et al., "Dysbiosis of the fecal microbiota in the TNBS-induced Crohn's disease mouse model," Applied Microbiology and Biotechnology, May 2016, 100(10):4485-94.

(56) References Cited

OTHER PUBLICATIONS

Heng et al., “Protein-Coupled Receptors Revisited: Therapeutic Applications Inspired by Synthetic Biology,” Annual Review of Pharmacology and Toxicology, Jan. 6, 2014, 54:227-49.
Heydenreich et al., “Stabilization of G protein-coupled receptors by point mutations, ” Frontiers in Pharmacology, Apr. 20, 2015, 6:82.
Higashikuni et al., “Advancing therapeutic applications of synthetic gene circuits,” Current Opinion in Biotechnology, Oct. 1, 2017, 47:133-41.
Hillmann et al., “Key determinants of nucleotide-activated G protein-coupled P2Y2 receptor function revealed by chemical and pharmacological experiments, mutagenesis and homology modeling,” Journal of Medicinal Chemistry, May 14, 2009, 52(9):2762-75.
Huang et al., “Fine-mapping inflammatory bowel disease loci to single-variant resolution,” Nature, Jul. 2017, 547(7662):173-8.
Hudson et al., “Functional heterologous protein expression by genetically engineered probiotic yeast *Saccharomyces boulardii*,” PloS one, Nov. 12, 2014, 9(11):e112660, 12 pages.
Idzko et al., “Nucleotide signalling during inflammation,” Nature, May 2014, 509(7500):310-7.
Inami et al., “ATP as a pathophysiologic mediator of bacteria-host crosstalk in the gastrointestinal tract,” International Journal of Molecular Sciences, Aug. 12, 2018, 19(8):2371.
Jostins et al., “Host-microbe interactions have shaped the genetic architecture of inflammatory bowel disease, ” Nature, Nov. 2012, 491(7422):119-24.
Junger, “Immune cell regulation by autocrine purinergic signalling, ” Nature Reviews Immunology, Mar. 2011, 11(3):201-12.
Kaplan, “The global burden of IBD: from 2015 to 2025,” Nature Reviews Gastroenterology & Hepatology, Dec. 2015, 12(12):720-7.
Keppler-Ross et al., “A new purple fluorescent color marker for genetic studies in Saccharomyces cerevisiae and Candida albicans,” Genetics, May 1, 2008, 179(1):705-10.
Knowles, “The GDA1_CD39 superfamily: NTPDases with diverse functions,” Purinergic Signalling, Mar. 2011, 7(1):21-45.
Komoszyński, “Comparative studies on animal and plant apyrases (ATP diphosphohydrolase EC 3.6. 1.5) with application of immunological techniques and various ATPase inhibitors,” Comparative Biochemistry and Physiology Part B: Biochemistry and Molecular Biology, Mar. 1, 1996, 113(3):581-91.
Kuleshov et al., “Enrichr: a comprehensive gene set enrichment analysis web server 2016 update,” Nucleic Acids Research, Jul. 2016, 44(W1):W90-7.
Kurashima et al., “Pathophysiological role of extracellular purinergic mediators in the control of intestinal inflammation,” Mediators of Inflammation, Oct. 2015, vol. 2015, 8 pages.
Ladds et al., “Functional analysis of heterologous GPCR signalling pathways in yeast,” Trends in Biotechnology, Jul. 1, 2005, 23(7):367-73.
Lagkouvardos et al., “The Mouse Intestinal Bacterial Collection (miBC) provides host-specific insight into cultured diversity and functional potential of the gut microbiota, ” Nature Microbiology, Aug. 8, 2016, 1(10):1-5.
Lamas et al., “CARD9 impacts colitis by altering gut microbiota metabolism of tryptophan into aryl hydrocarbon receptor ligands,” Nature Medicine, Jun. 2016, 22(6):598-605.
Landry et al., “Engineering diagnostic and therapeutic gut bacteria, ” Microbiology Spectrum, Oct. 2017, 5(5), 22 pages.
Lawrance et al., “A murine model of chronic inflammation-induced intestinal fibrosis down-regulated by antisense NF-κB,” Gastroenterology, Dec. 1, 2003, 125(6):1750-61.
Lee et al., “Galaxy7TM: flexible GPCR-ligand docking by structure refinement,” Nucleic Acids Research, Jul. 8, 2016, 44(W1):W502-6.
Lee et al., “A highly characterized yeast toolkit for modular, multipart assembly,” ACS Synthetic Biology, Sep. 18, 2015, 4(9):975-86.
Li et al., “Role of interleukin-22 in inflammatory bowel disease, ” World Journal of Gastroenterology: WJG, Dec. 12, 2014, 20(48):18177.
Lloyd-Price et al., “Multi-omics of the gut microbial ecosystem in inflammatory bowel diseases,” Nature, May 2019, 569(7758):655-62.
Lovell et al., “Structure validation by Cα geometry: ϕ, ψ and Cβ deviation,” Proteins: Structure, Function, and Bioinformatics, Feb. 15, 2003, 50(3):437-50.
Lozupone et al., “UniFrac: an effective distance metric for microbial community comparison,” The ISME Journal, Feb. 2011, 5(2):169-72.
Machiels et al., “A decrease of the butyrate-producing species *Roseburia hominis* and *Faecalibacterium prausnitzii* defines dysbiosis in patients with ulcerative colitis,” Gut, Aug. 1, 2014, 63(8):1275-83.
Magnani et al., “Co-evolving stability and conformational homogeneity of the human adenosine A2a receptor,” Proceedings of the National Academy of Sciences, Aug. 5, 2008, 105(31):10744-9.
Mao et al., “Probiotic strains detect and suppress cholera in mice,” Science Translational Medicine, Jun. 13, 2018, 10(445):eaao2586, 9 pages.
Marinissen et al., “G-protein-coupled receptors and signaling networks: emerging paradigms,” Trends in Pharmacological Sciences, Jul. 1, 2001, 22(7):368-76.
Marlow et al., “Why interleukin-10 supplementation does not work in Crohn’s disease patients,” World Journal of Gastroenterology: WJG, Jul. 7, 2013, 19(25):3931.
Martins et al., “Oral treatment with *Saccharomyces cerevisiae* strain UFMG 905 modulates immune responses and interferes with signal pathways involved in the activation of inflammation in a murine model of typhoid fever,” International Journal of Medical Microbiology, Apr. 1, 2011, 301(4):359-64.
Mascanfroni et al., “VK. IL-27 acts on DCs to suppress the T cell response and autoimmunity by inducing expression of the immunoregulatory molecule CD39,” Nature Immunology, Oct. 2013, 14(10):1054-63.
Mascanfroni et al., “Metabolic control of type 1 regulatory T cell differentiation by AHR and HIFI-α, ” Nature Medicine, Jun. 2015, 21(6):638-46.
McKay et al., “A platform of genetically engineered bacteria as vehicles for localized delivery of therapeutics: Toward applications for Crohn’s disease,” Bioengineering & Translational Medicine, Sep. 2018, 3(3):209-21.
Mimee et al., “Programming a human commensal bacterium, Bacteroides thetaiotaomicron, to sense and respond to stimuli in the murine gut microbiota,” Cell Systems, Jul. 29, 2015, 1(1):62-71.
Mimee et al., “Microbiome therapeutics—advances and challenges,” Advanced Drug Delivery Reviews, Oct. 1, 2016, 105:44, 30 pages.
Montaner et al., “Molecular Mechanisms Deployed by Virally Encoded G Protein Coupled Receptors in Human Diseases,” Annual Review of Pharmacology and Toxicology, 2013, 53:331, 24 pages.
Moon et al., “Genetic programs constructed from layered logic gates in single cells,” Nature, Nov. 2012, 491(7423):249-53.
Moser et al., “Genetic sensor for strong methylating compounds,” ACS Synthetic Biology, Oct. 18, 2013, 2(10):614-24.
Nash et al., “The gut mycobiome of the Human Microbiome Project healthy cohort,” Microbiome, Dec. 2017, 5(1):1-3.
Neurath, “Targeting immune cell circuits and trafficking in inflammatory bowel disease,” Nature Immunology, Aug. 2019, 20(8):970-9.
Nielsen et al., “Genetic circuit design automation,” Science, Apr. 1, 2016, 352(6281):aac7341, 13 pages.
Nikolaus et al., “Interferon β-1a in ulcerative colitis: a placebo controlled, randomised, dose escalating study,” Gut, Sep. 1, 2003, 52(9):1286-90.
Nourizad et al., “Methylotrophic yeast *Pichia pastoris* as a host for production of ATP-diphosphohydrolase (apyrase) from potato tubers (*Solanum tuberosum*),” Protein Expression and Purification, Feb. 1, 2003, 27(2):229-37.
Nowarski et al., “The stromal intervention: regulation of immunity and inflammation at the epithelial-mesenchymal barrier,” Cell, Jan. 26, 2017, 168(3):362-75.

(56) References Cited

OTHER PUBLICATIONS

Nygaard et al., “Ligand binding and micro-switches in 7TM receptor structures,” Trends in Pharmacological Sciences, May 1, 2009, 30(5):249-59.
Palma et al., “Probiotic *Saccharomyces cerevisiae* strains as biotherapeutic tools: is there room for improvement?,” Applied Microbiology and Biotechnology, Aug. 2015, 99(16):6563-70.
Paul et al., “Inflamed gut mucosa: downstream of interleukin-10,” European Journal of Clinical Investigation, Jan. 2012, 42(1):95-109.
PCT International Preliminary Report on Patentability in International Appln. No. PCT/US2020/048049, dated Mar. 10, 2022, 8 pages.
PCT International Search Report and Written Opinion in International Appln. No. PCT/US2020/048049, dated Jan. 4, 2021, 12 pages.
Peisajovich et al., “Protein engineers turned evolutionists,” Nature Methods, Dec. 2007, 4(12):991-4.
Peisajovich et al., “Rapid diversification of cell signaling phenotypes by modular domain recombination,” Science, Apr. 16, 2010, 328(5976):368-72.
Pliatsika et al., “Off-Spotter: very fast and exhaustive enumeration of genomic lookalikes for designing CRISPR/Cas guide RNAs,” Biology Direct, Dec. 2015, 10(1):1-0.
Proctor et al., “The Integrative Human Microbiome Project,” Nature, May 30, 2019, 569(7758):641-8.
Proietti et al., “ATP released by intestinal bacteria limits the generation of protective IgA against enteropathogens,” Nature Communications, Jan. 16, 2019, 10(1), 11 pages.
Prykhozhij et al., “CRISPR multitargeter: a web tool to find common and unique CRISPR single guide RNA targets in a set of similar sequences,” PloS one, Mar. 5, 2015, 10(3):e0119372, 18 pages.
Rafehi et al., “Molecular recognition of agonists and antagonists by the nucleotide- activated G protein-coupled P2Y2 receptor,” Journal of Medicinal Chemistry, Oct. 26, 2017, 60(20):8425, 58 pages.
Reeves et al., “Suppression of Clostridium difficile in the gastrointestinal tracts of germfree mice inoculated with a murine isolate from the family Lachnospiraceae,” Infection and Immunity, Nov. 2012, 80(11):3786-94.
Riglar et al., “Engineered bacteria can function in the mammalian gut long-term as live diagnostics of inflammation,” Nature Biotechnology, Jul. 2017, 35(7):653-8.
Rizzetto et al., “Fungal chitin induces trained immunity in human monocytes during cross-talk of the host with *Saccharomyces cerevisiae*,” Journal of Biological Chemistry, Apr. 8, 2016, 291(15):7961-72.
Rocchi et al., “Inflammatory bowel disease: a Canadian burden of illness review,” Canadian Journal of Gastroenterology, Nov. 1, 2012, 26(11):811-7.
Rogala et al., “Strategies to dissect host-microbial immune interactions that determine mucosal homeostasis vs. intestinal inflammation in gnotobiotic mice, ” Frontiers in Immunology, Feb. 18, 2020, 11:214.
Rothhammer et al., “Microglial control of astrocytes in response to microbial metabolites,” Nature, May 2018, 557(7707):724-8.
Rothhammer et al., “Type I interferons and microbial metabolites of tryptophan modulate astrocyte activity and central nervous system inflammation via the aryl hydrocarbon receptor,” Nature Medicine, Jun. 2016, 22(6):586-97.
Ryan et al., “Selection of chromosomal DNA libraries using a multiplex CRISPR. system,” elife, Aug. 19, 2014, 3:e03703, 15 pages.
Sato et al., “The robustness of a signaling complex to domain rearrangements facilitates network evolution,” PLoS biology, Dec. 9, 2014, 12(12):e1002012, 13 pages.
Schenk et al., “ATP inhibits the generation and function of regulatory T cells through the activation of purinergic P2X receptors,” Science Signaling, Mar. 1, 2011, 4(162):ra12, 31 pages.
Schmidt et al., “Identification of determinants required for agonistic and inverse agonistic ligand properties at the ADP receptor P2Y12,” Molecular Pharmacology, Jan. 1, 2013, 83(1):256-66.
Schott et al., “BlastPhyMe: A toolkit for rapid generation and analysis of protein- coding sequence datasets, ” bioRxiv, Jun. 19, 2016, 15 pages.
Schütz et al., “Directed evolution of G protein-coupled receptors in yeast for higher functional production in eukaryotic expression hosts,” Scientific Reports, Feb. 25, 2016, 6(1):1-6.
Scott et al., “Coupling of human rhodopsin to a yeast signaling pathway enables characterization of mutations associated with retinal disease,” Genetics, Feb. 1, 2019, 211(2):597-615.
Scott, “Building New Senses for Yeast: Responding to Light and Inflammation with S. 30-37 *Cerevisiae*,” Thesis, University of Toronto, Aug. 29, 2018, retrieved Nov. 29, 2020 from URL <https://tspace.library.utoronto.ca/bitstreamn/1807/102948/1/Scott_Benjamin_M_201811_PhD_thesis.pdf> [link now dead], pp. ii-iii, 111-164 (48 pages total).
Segata et al., “Metagenomic biomarker discovery and explanation,” Genome Biology, Jun. 2011, 12(6):1-8.
Sen et al., “Yeasts as probiotics: Mechanisms, outcomes, and future potential,” Fungal Genetics and Biology, Apr. 1, 2020, 137:103333, 26 pages.
Shaw et al., “Engineering a model cell for rational tuning of GPCR signaling,” Cell, Apr. 18, 2019, 177(3):782, 43 pages.
Siegel et al., “Risk of lymphoma associated with combination anti-tumor necrosis factor and immunomodulator therapy for the treatment of Crohn’s disease: a meta-analysis,” Clinical Gastroenterology and Hepatology, Aug. 1, 2009, 7(8):874-81.
Siuti et al., “Synthetic circuits integrating logic and memory in living cells,” Nature Biotechnology, May 2013, 31(5):448-52.
Sokol et al., “Fungal microbiota dysbiosis in IBD,” Gut, Jun. 1, 2017, 66(6):1039-48.
Sonnenberg et al., “Border patrol: regulation of immunity, inflammation and tissue homeostasis at barrier surfaces by IL-22,” Nature Immunology, May 2011, 12(5):383-90.
Speca et al., “Cellular and molecular mechanisms of intestinal fibrosis,” World Journal of Gastroenterology: WJG, Jul. 7, 2012, 18(28):3635, 27 pages.
Strati et al., “Age and gender affect the composition of fungal population of the human gastrointestinal tract,” Frontiers in Microbiology, Aug. 3, 2016, 7:1227, 16 pages.
Suez et al., “The pros, cons, and many unknowns of probiotics,” Nature Medicine, May 2019, 25(5):716-29.
Takemura et al., “Eosinophil depletion suppresses radiation-induced small intestinal fibrosis,” Science Translational Medicine, Feb. 21, 2018, 10(429):eaan0333, 15 pages.
Takenaka et al., “Control of tumor-associated macrophages and T cells in glioblastoma via AHR and CD39,” Nature Neuroscience, May 2019, 22(5):729-40.
Takenaka et al., “Regulation of the T cell response by CD39,” Trends in Immunology, Jul. 2016, 37(7):427-39.
Tehan et al., “Unifying family A GPCR theories of activation,” Pharmacology & Therapeutics, Jul. 1, 2014, 143(1):51-60.
Trivedi et al., “Dextran sulfate sodium-induced ulcerative colitis leads to increased hematopoiesis and induces both local as well as systemic genotoxicity in mice,” Mutation Research/Genetic Toxicology and Environmental Mutagenesis, May 15, 2012, 744(2):172-83.
Veloria et al., “Optimization of a Luminescence-Based High-Throughput Screening Assay for Detecting Apyrase Activity,” SLAS Discovery: Advancing Life Sciences R&D, Jan. 2017, 22(1):94-101.
Venkatakrishnan et al., “Diverse activation pathways in class A GPCRs converge near the G-protein-coupling region,” Nature, Aug. 2016, 536(7617):484-7.
Vuerich et al., “Ectonucleotidases in intestinal and hepatic inflammation,” Frontiers in Immunology, Mar. 19, 2019, 10:507, 11 pages.
Wan et al., “Extracellular ATP mediates inflammatory responses in colitis via P2× 7 receptor signaling,” Scientific Reports, Jan. 7, 2016, 6(1):1-0.

(56) References Cited

OTHER PUBLICATIONS

Webb et al., "Comparative protein structure modeling using MODELLER," Current Protocols in Bioinformatics, Jun. 2016, 54(1), 15 pages.
Wei et al., "Bacterial virulence proteins as tools to rewire kinase pathways in yeast and immune cells, " Nature, Aug. 2012, 488(7411):384, 19 pages.
Wiederstein et al., "ProSA-web: interactive web service for the recognition of errors in three-dimensional structures of proteins," Nucleic Acids Research, Jul. 1, 2007, 35(suppl_2):W407-10.
Wilhelm et al., "Graft-versus-host disease is enhanced by extracellular ATP activating P2X7R," Nature Medicine, Dec. 2010, 16(12):1434-8.
Xia et al., "Synthetic genetic circuits for programmable biological functionalities," Biotechnology Advances, Nov. 1, 2019, 37(6):107393, 36 pages.
Yeste et al., "IL-21 induces IL-22 production in CD4+ T cells," Nature Communications, May 6, 2014, 5(1), 13 pages.
Zanello et al., "*Saccharomyces cerevisiae* modulates immune gene expressions and inhibits ETEC-mediated ERK1/2 and p38 signaling pathways in intestinal epithelial cells," PloS one, Apr. 4, 2011, 6(4):e18573, 13 pages.
Zenewicz et al., "Innate and adaptive interleukin-22 protects mice from inflammatory bowel disease, " Immunity, Dec. 19, 2008, ;29(6):947-57.
Zhang et al., "Inflammasome activation has an important role in the development of spontaneous colitis," Mucosal Immunology, Sep. 2014, 7(5):1139-50.
Zhu et al., "Roseburia intestinalis inhibits interleukin-17 excretion and promotes regulatory T cells differentiation in colitis," Molecular Medicine Reports, Jun. 1, 2018, 17(6):7567-74.
EP Extended European Search Report in European Appln. No. 20858489.6, mailed on Sep. 1, 2023, 6 pages.
Bagchi et al., "The P2Y2 nucleotide receptor interacts with αv integrins to activate Go and induce cell migration," Journal of Biological Chemistry, Nov. 2005, 280(47):39050-7.
JP Office Action in Japanese Appln. No. 2022-513490, mailed on May 21, 2024, 17 pages (with English translation).

* cited by examiner

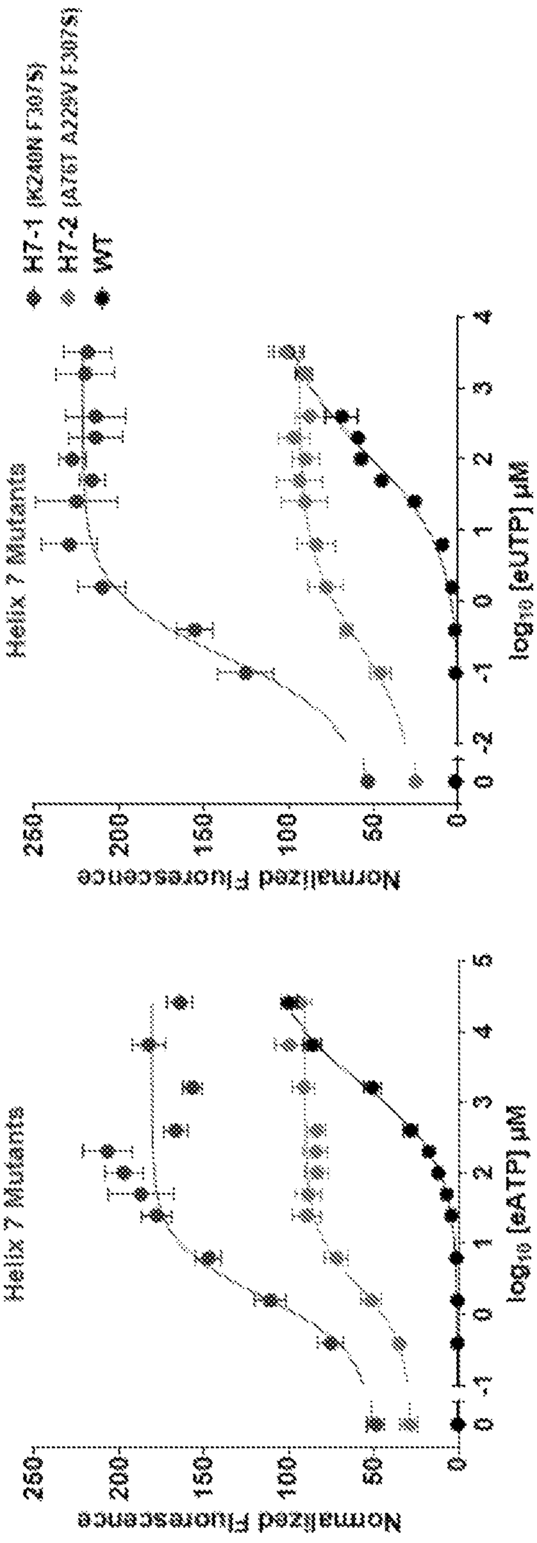
*FIG. 2B, continued*

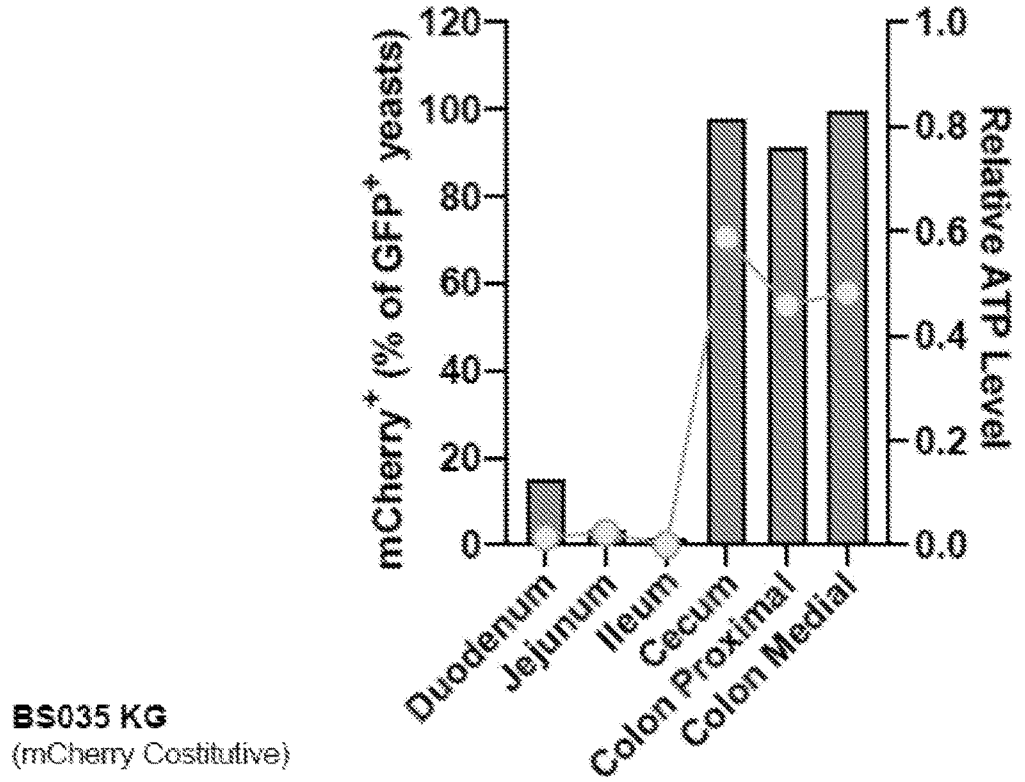
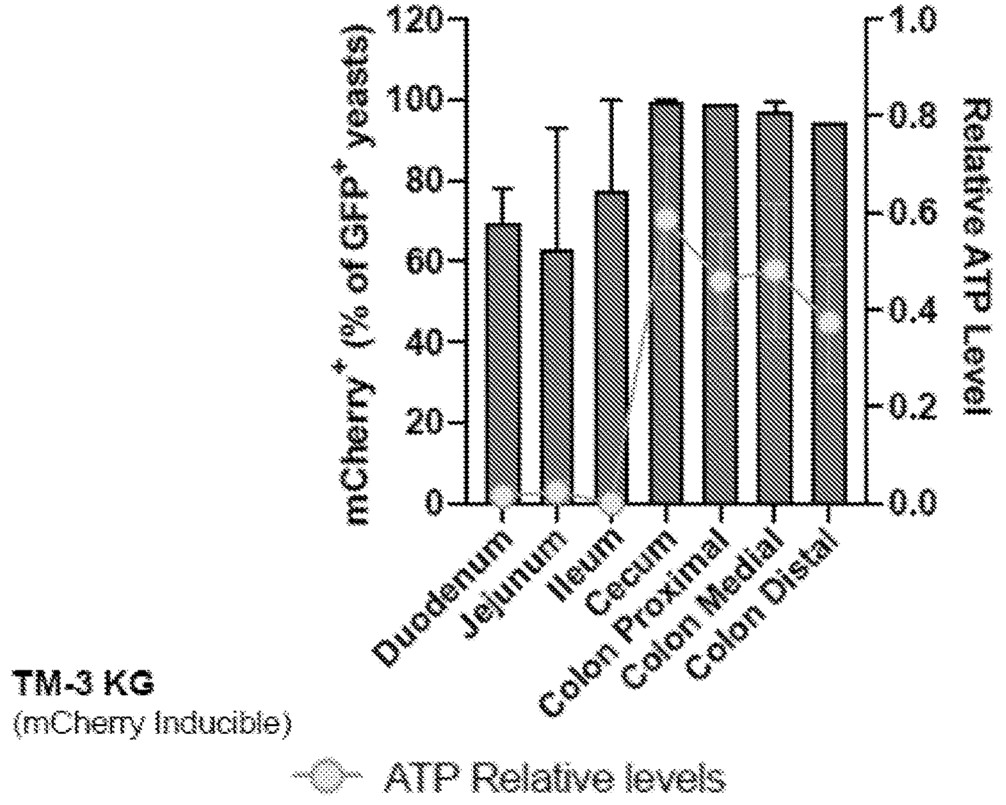
*FIG. 5A*

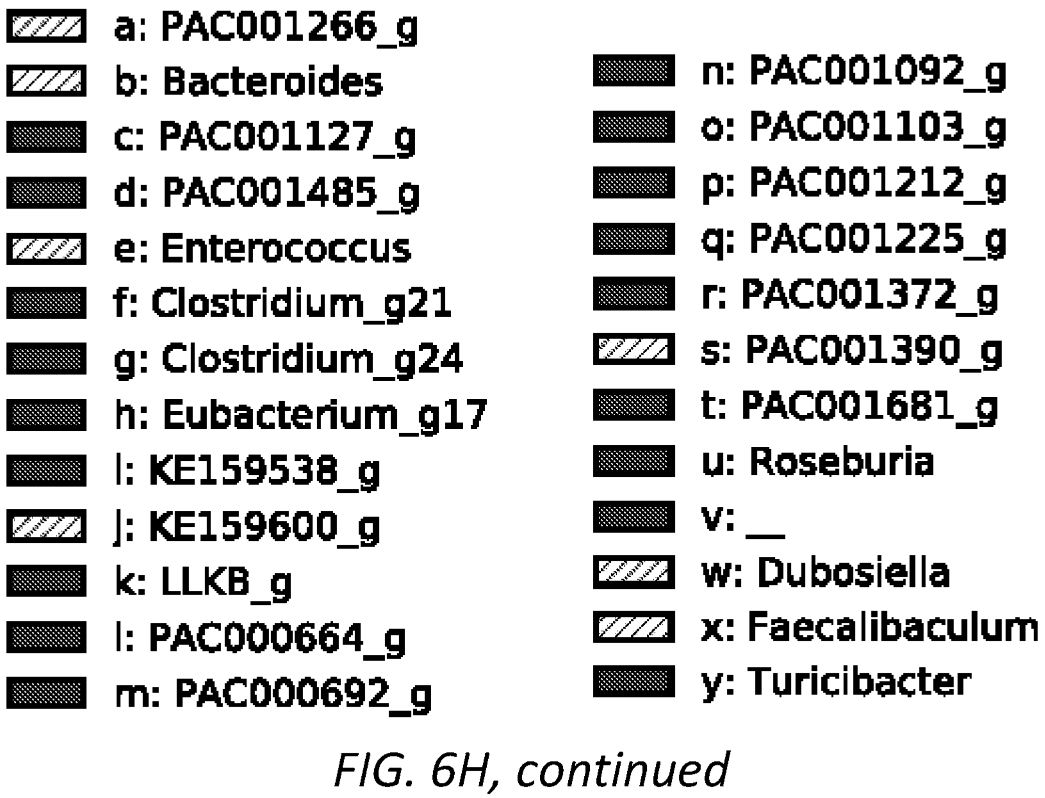
*FIG. 6H, continued*
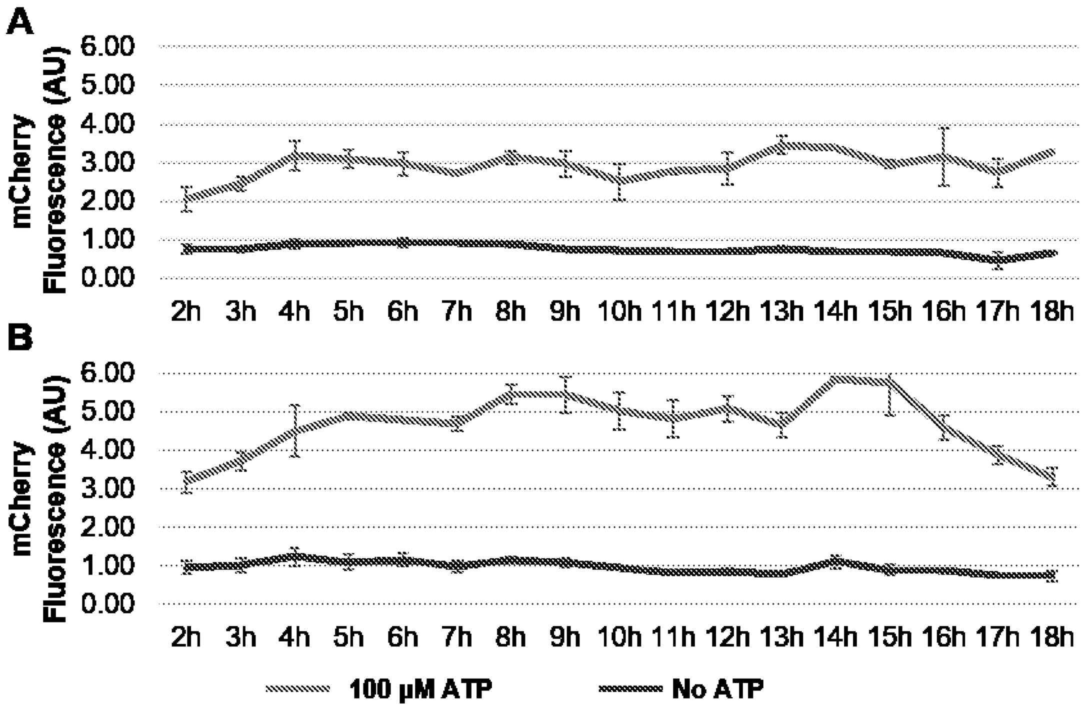
*FIGs. 7A-B*

FIG. 9A
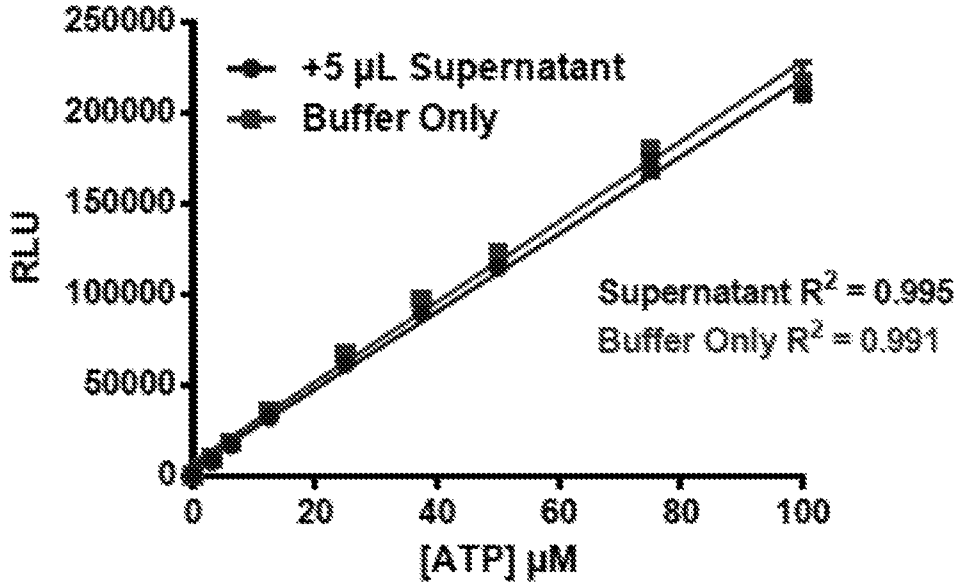
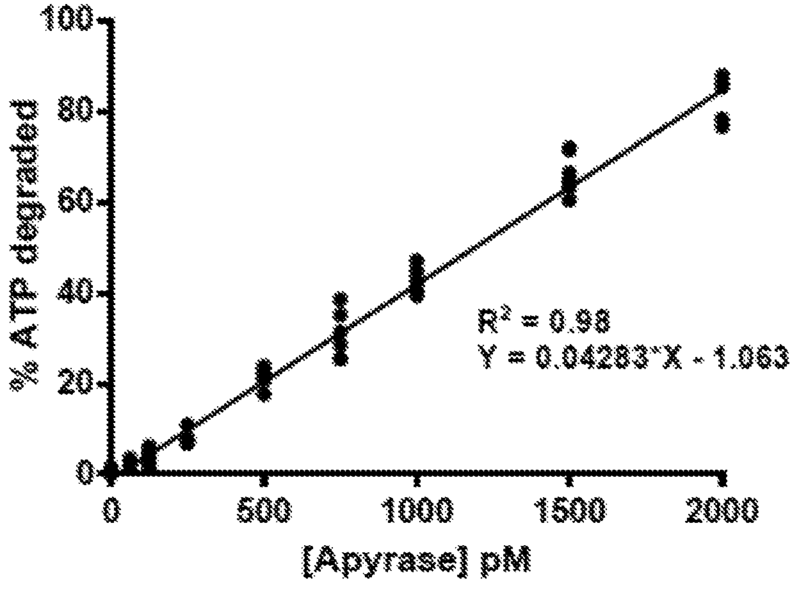
FIG. 9B

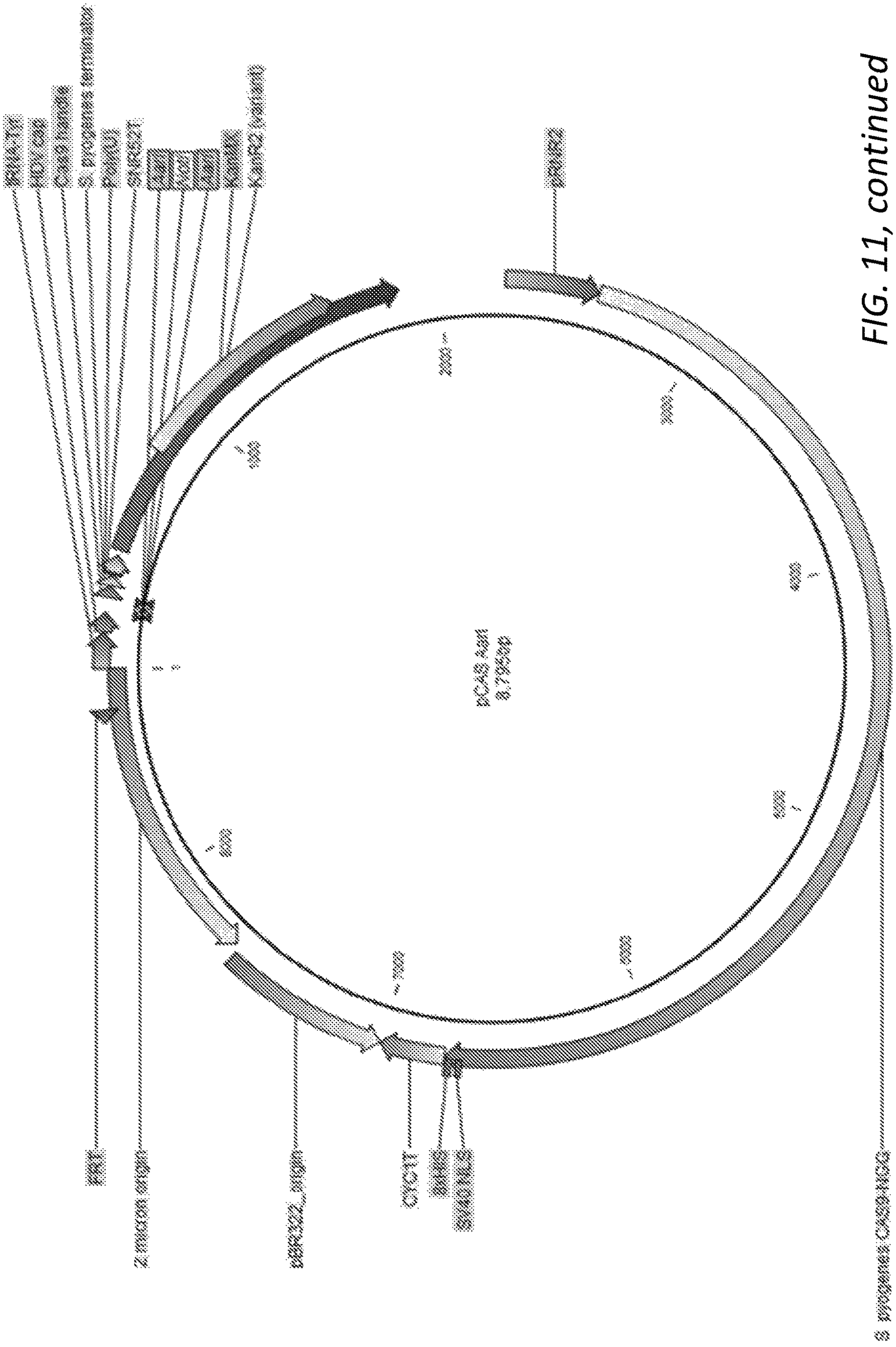
FIG. 11, continued

COMPOSITIONS AND USES FOR ENGINEERED THERAPEUTIC MICROBES AND ASSOCIATED RECEPTORS

CLAIM OF PRIORITY

This application is a national stage filing under 35 U.S.C. § 371 of PCT International Application No. PCT/US2020/048049, filed Aug. 26, 2020, which claims the benefit of U.S. Provisional Application Ser. No. 62/891,603, filed on 26 Aug. 2019. The entire contents of the foregoing are incorporated herein by reference.

SEQUENCE LISTING

This application contains a Sequence Listing that has been submitted electronically as an ASCII text file named "29618-0267US1_SL ST25.txt." The ASCII text file, created on Nov. 20, 2025, is 47,436 bytes in size. The material in the ASCII text file is hereby incorporated by reference in its entirety.

TECHNICAL FIELD

Described herein are microbial probiotics that, in response to metabolite extracellular ATP (eATP) produced in the microenvironment of inflamed tissues detected, e.g., via an engineered mammalian P2Y purinoceptor 2 (P2Y2) receptor, secrete an anti-inflammatory protein, e.g., IL-2, IL-10, or the CD39-like eATP-degrading enzyme apyrase.

BACKGROUND

Inflammatory Bowel Disease (IBD) is a complex chronic inflammatory disorder of the gastrointestinal tract that includes Crohn's Disease and Ulcerative Colitis (1). Most available IBD therapies suppress the immune system systemically, increasing the risk of infections and some types of cancer (2). In addition, many patients with IBD do not respond to therapy or show loss of clinical response over time (2). Thus, there is a need for novel therapeutic approaches for IBD.

The microbiome controls immune processes relevant to the pathology of multiple human diseases including IBD (3-5). For example, IBD-associated single-nucleotide polymorphisms promote changes in the intestinal microbiota that result in the reduced production of anti-inflammatory microbial metabolites (6). Genetic polymorphisms associated to IBD also control the responsiveness to anti-inflammatory microbial metabolites (7). The role of the microbiome in disease pathogenesis, and in particular the anti-inflammatory effects of certain commensal microorganisms, supports the use of probiotic-based approaches for the treatment of IBD (8-10). However, therapies based solely on the intrinsic anti-inflammatory properties of un-manipulated probiotics may not be efficacious in controlling ongoing intestinal inflammation (10).

SUMMARY

The development of therapeutic probiotics is a major area of IBD research. Previous attempts used engineered probiotics expressing therapeutic proteins in an uncontrolled manner, based on plasmid systems which require constant selection pressure and present the risk of horizontal transfer to other bacteria (80, 81). To overcome these limitations, the present inventors applied directed evolution and CRISPR/

Cas9 to engineer microbes with a gene circuit that produces an anti-inflammatory in response to eATP levels, delivering a probiotic-based dynamic anti-inflammatory response in the inflamed tissue microenvironment. Provided herein are engineered therapeutic microbes designed to detect pathogenic gastrointestinal (GI) inflammation, and dynamically respond by delivery of a therapeutic protein, and methods of use thereof.

Thus, provided herein is an isolated *Saccharomyces* cell (or cells, e.g., a population of such cells) that has been engineered to express one, two, or all three exogenous proteins selected from: (i) a mammalian P2Y purinoceptor 2 (P2Y2) protein, preferably human P2Y2; (ii) a mutant Gpa1 protein comprising at least 5 C-terminal residues from a mammalian G alpha, preferably Gai3, wherein the mutant Gpa1 protein couples the P2Y2 protein to the yeast mating pathway; and (iii) an anti-inflammatory protein, optionally wherein the anti-inflammatory protein is mammalian, preferably human, and wherein the anti-inflammatory protein is expressed under the control of a promoter activated downstream of P2Y2 activation, optionally a mating-responsive promoter, wherein the isolated *Saccharomyces* cell secretes the anti-inflammatory protein in the presence of extracellular adenosine triphosphate (eATP). Preferably the anti-inflammatory protein is secreted in the presence of eATP at pro-inflammatory concentrations (~100 micromolar to high millimolar). Preferably, the anti-inflammatory protein is secreted in an eATP concentration-dependent manner, where a greater eATP concentration leads to a greater secretion of the anti-inflammatory protein within the dynamic range of the engineered P2Y2 receptor.

In some embodiments, the *Saccharomyces* cell has been engineered to reduce or remove expression of one or more endogenous proteins selected from the group consisting of: (i) a yeast GPCR, e.g., alpha-factor pheromone receptor STE2 (NP_116627.2); (ii) negative regulator of pathway function GTPase-activating protein SST2 (NP_013557.1); (iii) cell cycle regulator cyclin-dependent protein serine/threonine kinase inhibiting protein FAR1 (NP_012378.1); and (iv) yeast G alpha protein guanine nucleotide-binding protein subunit alpha GPA1 (NP_011868.1).

In some embodiments, the anti-inflammatory protein comprises a yeast-derived leader peptide that directs the protein to be secreted, and optionally lacks any signal or leader sequence endogenous to the anti-inflammatory protein.

In some embodiments, the anti-inflammatory protein comprises apyrase, interleukin 10 (IL-10), IL-2, IL-27, IL-22, or IFN-beta.

In some embodiments, at least one of the P2Y2 protein, mutant Gpa1, or anti-inflammatory protein are expressed from sequences codon-optimized for expression in the *Saccharomyces* cell.

In some embodiments, the P2Y2 comprises one or more mutations that increase expression of the anti-inflammatory protein. In some embodiments, the mutations are in residues peripheral to the ligand binding pocket (optionally $A76^{2.47}$, $N116^{3.35}$, $C119^{3.38}$, $L162^{4.54}$, $Q165^{4.57}$) and/or in residues in the intracellular facing side of the receptor (optionally $F58^{1.57}$, $L59^{1.58}$, $C60^{1.59}$, $A229^{ICL3}$, $K240^{6.31}$, $F307^{7.54}$, $G310^{C\text{-}term}$). In some embodiments, one or more mutations are in residues $F58^{1.57}$, $N116^{3.35}$, $F307^{7.54}$ and/or $Q165^{4.57}$. In some embodiments, the one or more mutations comprise F58C, Q165H, F307S, and/or N116S. In some embodiments, the mutations comprise a mutation at N116. In some embodiments, the mutations comprise a mutation at N116 in combination with a mutation at F58 or F307. In some embodiments, the mutations comprise mutations N116S, optionally in combination with mutations F58I or F307S. In some embodiments, the P2Y2 further comprises mutations at L59 and/or C119. In some embodiments, the further mutations comprise L59I and/or C119S.

In some embodiments, the promoter activated downstream of P2Y2 activation is a mating-responsive promoter, e.g., pFUS1 or pFIG. 1

In some embodiments, the expression of the anti-inflammatory protein is driven by a synthetic transcription factor comprising a pheromone responsive domain and a DNA binding domain, binding to non-yeast DNA operator sequences upstream of the sequence encoding the anti-inflammatory protein.

In some embodiments, the isolated *Saccharomyces* cell is *S. cerevisiae* or *S. boulardii.*

Also provided herein are compositions that include the isolated *Saccharomyces* cells described herein, and optionally a physiologically-acceptable carrier. In some embodiments, the compositions are in a solid form for oral administration, e.g., tablets, pills, capsules, soft gelatin capsules, sugarcoated pills, orodispersing/orodispersing tablets, or effervescent tablets.

In some embodiments, the compositions are in a liquid form for oral administration, e.g., a drinkable solution.

In some embodiments, the compositions are nutritional compositions, optionally comprising liquid or solid food, feed or drinking water.

In some embodiments, the nutritional composition is selected from beverages (optionally smoothies or cultured beverages, flavored beverages, yogurt, drinking yogurt, set yogurt, fruit and/or vegetable juices or concentrates thereof, fruit and vegetable juice powders, reconstituted fruit products, powders, malt or soy or cereal based beverages, breakfast cereal such as muesli flakes, spreads, meal replacements, confectionary, chocolate, gels, ice creams, cereal, fruit, and/or chocolate bars, energy bars, snack bars, food bars, sauces, dips, and sports supplements including dairy and non-dairy based sports supplements.

Also provided herein are methods for reducing inflammation in a subject, the method comprising administering to the subject an effective amount of the isolated *Saccharomyces* cells or compositions as described herein. Further provided are the isolated *Saccharomyces* cells and the compositions for use in a method of reducing inflammation in a subject. In some embodiments, the subject has or is at risk of developing inflammatory bowel disease (IBD).

Additionally provided herein are engineered mammalian P2Y purinoceptor 2 (P2Y2) proteins comprising one or more mutations in residues peripheral to the ligand binding pocket (optionally $A76^{2.47}$, $N116^{3.35}$, $C119^{3.38}$, $L162^{4.54}$, $Q165^{4.57}$) and/or in residues in the intracellular facing side of the receptor (optionally $F58^{1.57}$, $L59^{1.58}$, $C60^{1.59}$, $A229^{ICL3}$ $K240^{6.31}$, $F307^{7.54}$, $G310^{C\text{-}term}$).

In some embodiments, the one or more mutations are in residues $F58^{1.57}$, $N116^{3.35}$, $F307^{7.54}$ and/or $Q165^{4.57}$.

In some embodiments, the one or more mutations comprise F58C, Q165H, F307S, and/or N116S.

In some embodiments, the mutations comprise a mutation at N116.

In some embodiments, the mutations comprise a mutation at N116 in combination with a mutation at F58 or F307.

In some embodiments, the mutations comprise mutations N116S, optionally in combination with mutations F58I or F307S.

In some embodiments, the P2Y2 further comprises mutations at L59 and/or C119.

In some embodiments, the further mutations comprise L59I and/or C119S.

Also provided herein is an isolated nucleic acid sequence encoding the engineered mammalian P2Y2 described herein.

Also provided herein is a host cell comprising the isolated nucleic acid sequence described herein, and optionally expressing the engineered mammalian P2Y2 described herein.

In some embodiments, the cell is a *Saccharomyces* cell, and the isolated nucleic acid sequence is codon-optimized for expression in the *Saccharomyces* cell.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 5A-K: eATP-responsive synthetic yeast ameliorate TNBS-induced colitis. (A) mCherry positive yeasts (% of total GFP yeast) quantified by flow cytometry in the fecal content of the specified portion of the gut 2 hours after oral gavage with ATP-induced TM-3 yeast strains (left) or BS035 constitutive (right). ATP levels were measured in the same portions of the gut. (B) Changes in body weight following TNBS rectal administration. Statistical significance among groups was evaluated by a two-way ANOVA followed by Tukey's multiple comparisons post-hoc test, ***P<0.05; *P<0.05; ns=not significant; (n=10). (C) Colon length of mice from experimental groups shown in (B) (n=4). (D) Hematoxylin and eosin staining 20× (top) and 40× (bottom) magnification. Representative colon section of each group is shown. Open arrowheads: immune cell infiltrates in the mucosa with structure disruption. Black arrows: immune cells infiltration at submucosa: Black brackets: edematous submucosa. Scale bars=100 μm (E) Histomorphology disease score of mice from groups like (B) where higher score means higher severity of the tissue disruption. (n=4) (F) RNAseq analysis of colon samples from mice in the experimental groups shown in (B). Heatmap of differentially expressed genes. (G) $Foxp3^+$ T regulatory cells in mesenteric lymph nodes in the experimental groups shown in (B) (n=3). (H) Foxp3, Ifng and Il17 mRNA expression determined by qPCR in colon tissue of samples from groups like (B) (n=3). (I) Changes in body weight during the course of DSS-induced colitis in mice treated with probiotic yeasts as in (B). Statistical significance among groups was evaluated by a two-way ANOVA followed by Tukey's multiple comparisons post-hoc test, **P<0.01 *P<0.05; ns=not significant. (n=12). (J) Gene expression in colon samples from yeast-treated mice determined by NanoString 21 days after the initiation of DSS administration. Heatmap of differentially expressed genes. Data are representative of two independent experiments of pooled samples from n=3 mice per group. (K) Nos2, Ccl2 and Il1b mRNA expression determined by qPCR in RNA extracted from colon tissue from mice from groups as in (J) (n=3). *P<0.01, P<0.01; *P<0.05; ns=not significant as determined by one-way ANOVA followed by post-hoc tests Tukey's or Sidak's test for selected multiple comparisons. Data representative of 3 independent experiments.

FIGS. 7A-B. Response to eATP over time of engineered mating pathway. (A,B) Yeasts from the BS016 strain transformed with plasmid pRS316 pTDH3 P2Y2 (WT human P2Y2 receptor) were incubated with 100 μM ATP in 300 μL (A) or 5 mL SD-URA media (B); and mCherry fluorescence was quantified (2 individual colonies each, error bars represent standard deviation).

FIGS. 9A-B: ATP concentration in yeast supernatants. (A) Slopes are not statistically different. (B) To estimate the amount of active apyrase secreted by yeast, 50 μM ATP was incubated with the indicated concentration of commercial apyrase for 30 minutes at 30° C., with 5 μL supernatant from a culture of strain CB008, in a 50 μL reaction volume and residual ATP was quantified. No apyrase activity was observed when 31.3 μM commercial apyrase was added.

DETAILED DESCRIPTION

Figure 1A:
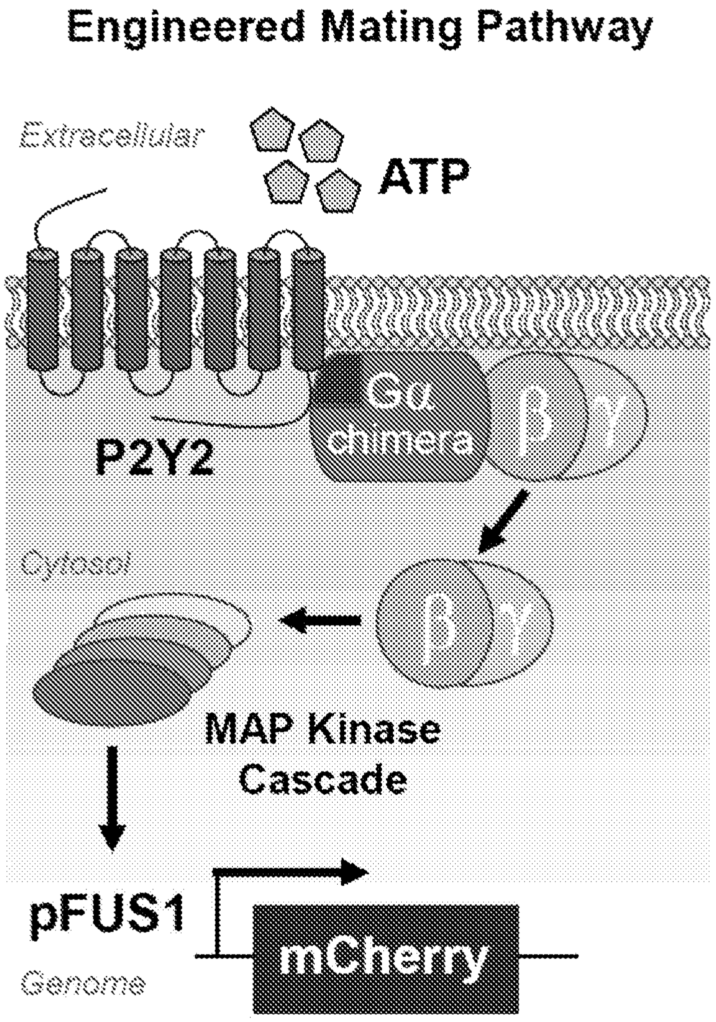
FIGS. 1A-D: Directed evolution of human P2Y purinoceptor 2 (P2Y2) receptor. (A) Human P2Y2 receptor activation was functionally coupled to the expression of a fluorescent reporter protein, mCherry, utilizing the mating-responsive promoter pFUS1. Modifications to the mating pathway included the knockout of negative regulator Sst2, and the gene encoding Far1 which halts cell growth in the wild-type mating pathway. The chimeric G alpha protein (Gpa1-Gai3) contains the 5 C-terminal amino acids of mammalian $G\alpha_{i3}$. (B) Engineered mating pathway response to UTP using the wild type (WT) human P2Y2 receptor and various yeast strains with integrated Gpa1-Gα chimeras as follows: BS019 ($G_{14}$), BS020 ($G_q$), BS016 ($G_{i3}$). Following incubation for 6 hours with the indicated concentration of UTP, the activation of the mating pathway was monitored by quantifying mCherry fluorescence by flow cytometry. Data points represent the mean of two colonies. Error bars represent the SEM. *$P<0.05$ vs 0 μM UTP. (C) Cells expressing the human WT P2Y2 receptor were treated with UTP and ATP, and mCherry fluorescence was quantified by flow cytometry. Data points represent the mean of six colonies for ATP, three colonies for UTP. Error bars represent the SEM. (D) A plasmid library of human P2Y2 receptor mutants generated by error-prone PCR was transformed into the Gpa1-Gai3 mCherry reporter strain. Cells were treated with 100 μM ATP, and fluorescence-activated cell sorting was used to select for highly-activating mutants (top 1% of mCherry fluorescence). Individual yeast colonies were then screened to confirm the desired phenotype and sequenced.
Figure 1B:
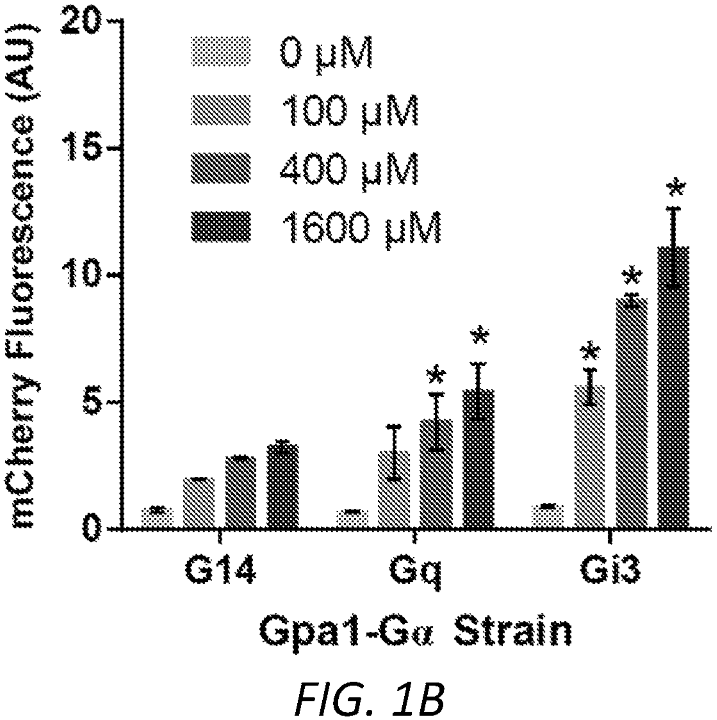

The convergence of efficient genetic manipulation (11, 12) and advanced synthetic gene circuit design (13, 14) paved the way for increasingly complex microbial engineering (15-18). In fact, recent advances in synthetic biology enabled the engineering of probiotics to deliver therapeutic proteins in response to disease-associated signals (19-22). One such signal relevant to IBD is extracellular adenosine triphosphate (eATP) which, upon release by activated immune cells and commensal bacteria, signals via purinergic receptors to trigger pro-inflammatory cytokine production, boost effector T cell activation, suppress regulatory T-cell responses and promote enteric neuron apoptosis among other biological responses thought to contribute to IBD pathology (23-27). eATP signaling is limited by the membrane-bound ectonucleoside triphosphate diphosphohydrolase 1 (ENTPD1, also known as CD39), which hydrolyzes eATP into AMP; AMP is then metabolized by CD73 into immunosuppressive adenosine. CD39 limits eATP-driven pro-inflammatory responses, while it boosts the differentiation, stability and function of regulatory T cells (26). Further support for the physiological role of eATP and CD39 in the control of intestinal inflammation is provided by reports of dysregulated purinergic signaling in IBD patients resulting from increased eATP production and/or its decreased hydrolysis (25, 28).

Genetic polymorphisms that decrease CD39 expression have been associated with Crohn's disease (68). CD39 on Tregs suppresses effector T-cell generation and function in experimental and human IBD (26-28, 69). Indeed, increased CD39 levels are associated with disease remission induced by blocking antibodies against TNFα in IBD patients (70). Conversely, purinergic signaling driven by eATP promotes inflammation through multiple mechanisms including the modulation of antigen presenting cells (71), the boost of effector T-cell activation (23, 72) and the decreased function and stability of regulatory T cells (26, 27, 73). eATP also limits the production of immunoglobulin A (74), which protects the intestinal barrier and promotes the engraftment of anti-inflammatory commensal bacteria (75, 76). In addition, eATP also acts on non-immune cells to promote IBD pathogenesis by triggering the apoptosis of enteric neurons (24). Thus, the blockade of eATP-driven signaling is an attractive therapeutic approach for IBD.

eATP-depletion with apyrase has been shown to ameliorate intestinal inflammation (23). These anti-inflammatory effects of apyrase likely involve both eATP depletion through its conversion into AMP, and also the generation of immunosuppressive adenosine from AMP (29). Adenosine suppresses T-cell activation via the A2A adenosine receptor (29). Indeed, we recently reported that adenosine production driven by CD39 suppresses tumor-specific T cells in glioblastoma (77). Hence, the modulation of the eATP/adenosine balance is a potential approach to treat inflammation. However, the clinical application of this approach requires suitable methods for therapeutic agent administration and inducible systems that modulate the eATP/adenosine balance where and when needed to minimize unwanted side effects such as immunosuppression and fibrosis (26, 28, 77) and intestinal microbiome dysregulation (29, 30).

Utilizing the modularity of the *S. cerevisiae* mating pathway, with directed evolution (33) and synthetic biology (34) approaches, strains of this yeast were modified to express an engineered human G protein-coupled receptor (GPCR) that is activated by a pro-inflammatory signal, eliciting the secretion of a therapeutic protein. GPCRs function as biological sensors to detect a wide diversity of signals, including the detection of molecules indicative of disease (Marinissen, M. J. & Gutkind, J. S. G-protein-coupled receptors and signaling networks: emerging paradigms. Trends in pharmacological sciences 22, 368-376 (2001)). This ability makes GPCRs useful components of synthetic gene circuits, to elicit programed responses to specific disease cues (Heng, B. C., Aubel, D. & Fussenegger, M. G protein-coupled receptors revisited: therapeutic applications inspired by synthetic biology. Annu Rev Pharmacol Toxicol 54, 227-249 (2014)). The *S. cerevisiae* mating pathway provides a well characterized model for GPCR signaling that can be rewired to accommodate activation by human GPCRs (Ladds, G., Goddard, A. & Davey, J. Functional analysis of heterologous GPCR signalling pathways in yeast. Trends Biotechnol 23, 367-373 (2005)). Elevated extracellular adenosine triphosphate (ATP) is a major pro-inflammatory signal (Bours, M. J., Dagnelie, P. C., Giuliani, A. L., Wesselius, A. & Di Virgilio, F. P2 receptors and extracellular ATP: a novel homeostatic pathway in inflammation. Frontiers in bioscience 3, 1443-1456 (2011)), which increases over 100-fold in the gut in IBD (>100 μM) (Kurashima, Y., Kiyono, H. & Kunisawa, J. Pathophysiological role of extracellular purinergic mediators in the control of intestinal inflammation. Mediators of inflammation 2015, 427125 (2015)), and is specifically detected by the purinergic family of GPCRs (Burnstock, G. & Boeynaems, J. M. Purinergic signalling and immune cells. Purinergic signalling 10, 529-564 (2014)). The enzyme apyrase directly degrades ATP, converting it to immunosuppressive adenosine (Cekic, C. & Linden, J. Purinergic regulation of the immune system. Nature reviews. Immunology 16, 177-192 (2016)), and apyrase was shown to reduce GI inflammation in an animal model of IBD (Wan, P. et al. Extracellular ATP mediates inflammatory responses in colitis via P2×7 receptor signaling. Sci Rep 6, 19108 (2016)). The anti-inflammatory cytokine interleukin 10 (IL-10) is critical to limiting inflammation responses in the gut (Paul, G., Khare, V. & Gasche, C. Inflamed gut mucosa: downstream of interleukin-10. Eur J Clin Invest 42, 95-109 (2012)). Microbes have been engineered to constitutively secrete IL-10 (Braat, H. et al. A phase I trial with transgenic bacteria expressing interleukin-10 in Crohn's disease. Clin Gastroenterol Hepatol 4, 754-759 (2006); Rottiers, P., Vandenbroucke, K. & Iserentant, D., Vol. EP1931762 (B1). (ed. E. P. Office) 1-26 (Actogenix NV, Belgium; 2012)), but not in response to a pro-inflammatory signal, which have shown promise in a Phase I clinical trial for treating IBD (Braat, H. et al. (2006).).

Described herein are microbial probiotics that, in response to metabolite eATP produced in the microenvironment of inflamed tissues detected, e.g., via an engineered human P2Y2 receptor, secrete an anti-inflammatory protein, e.g., IL-2, IL-10, or the CD39-like eATP-degrading enzyme apyrase, which depletes pro-inflammatory eATP and promotes the generation of immunosuppressive adenosine. These engineered apyrase-expressing yeasts suppressed experimental intestinal inflammation in mice, reducing intestinal fibrosis and dysbiosis. The specific molecular pathways involved in purinergic signaling during inflammation are outlined in FIG. 12; without wishing to be bound by theory, FIG. 12 includes indications of how the engineered microbes are believed to modulate these pathways to dynamically treat inflammation in the GI tract.

The present data show that controlled eATP depletion by yeast probiotics engineered to produce apyrase in response to eATP-sensing minimize fibrosis induction. Moreover, the use of an inducible engineered yeast strain to modulate purinergic signaling also allowed the recovery of healthy microbiome, minimizing the dysbiosis thought to contribute to the pathology IBD and other human disorders (3, 4).

Engineered Microbes

The inherent modularity of signaling pathways (78) enables engineering using exogenous proteins (79). *Saccharomyces* species are long-known for their use in foods, and certain *Saccharomyces* species have also been used as safe probiotics harboring engineered gene circuits to drive the controlled expression of proteins in response to stimuli of interest (15, 31, 32). In some embodiments, the present engineered microbes are made in *S. cerevisiae*. *S. boulardii* has been more commonly used as a probiotic than *S. cerevisiae* (89, 90), and the genetic tools to manipulate *S. boulardii* are available (91, 92). Thus, although *S. cerevisiae* is exemplified herein, the inducible system described herein can be established using other microbes, including *S. boulardii*.

In some embodiments, the microbes are generated by modifying the genome of the parental microbe, e.g., *Saccharomyces*, e.g., *S. cerevisiae*. The modifications can include (but are not limited to) introduction of the following proteins to the genome of the yeast: (i) engineered P2Y2, containing up to three mutations making it more responsive to eATP, e.g. under the control of a constitutive promoter (pTDH3); (ii) a mutant Gpa1 protein, e.g., containing the 5 C-terminal residues of a mammalian G alpha (Gai3), which couples P2Y2 to the yeast mating pathway; and (4) potato apyrase or interleukin 10 (IL-10) containing a yeast-derived leader peptide that directs the apyrase to be secreted, controlled by a promoter downstream of GPCR activation, e.g., from the Fus1 gene. The modifications can also include (but are not limited to) deletion of one or more endogenous yeast proteins from the genome: (i) the natural yeast GPCR mating pathway receptor Ste2 (e.g., alpha-factor pheromone receptor STE2 (NP_116627.2); to avoid pathway activation by natural ligands), (ii) the negative regulator of pathway function Sst2 (e.g., negative regulator of pathway function GTPase-activating protein SST2 (NP_013557.1); to increase the pathway response when activated by P2Y2), (iii) the cell cycle regulator Far1 (e.g., cell cycle regulator cyclin-dependent protein serine/threonine kinase inhibiting protein FAR1 (NP_012378.1); to avoid cell cycle arrest upon mating pathway activation), and (iv) the yeast G alpha protein Gpa1 (e.g., yeast G alpha protein guanine nucleotide-binding protein subunit alpha GPA1 (NP_011868.1); to avoid competition for binding to other pathway components).

Thus the methods can include introducing a mutant G alpha protein where the 5 C-terminal amino acids of Gpa1 (KIGII) was replaced with the 5 C-terminal amino acids from the indicated mammalian Gα protein (Brown et al., Yeast. 2000 Jan. 15; 16 (1): 11-22. 2000) (e.g., a chimeric yeast Gpa1-human Gai3 protein), introducing P2Y2 (e.g., a mutant P2Y2 optionally codon optimized for expression by yeast), and introducing an anti-inflammatory molecules such as apyrase or interleukin 10 (IL-10) controlled by a promoter activated downstream of P2Y2 activation (e.g. a mating pathway-responsive promoter). As shown herein, engineered variants of the GPCR P2Y2 responded to concentrations of eATP indicative of inflammation (~100 micromolar to high millimolar). In addition, apyrase or IL-10 were secreted by engineered yeast strains in response to P2Y2 activation, in an ATP concentration dependent manner, and the apyrase functioned to degrade extracellular ATP. Finally, in a mouse model of IBD, treatment with engineered yeast strains that secrete apyrase directly improved disease outcomes and reduced pro-inflammatory cytokine production. The engineered yeast described herein can include, for example, a self-tunable P2Y2-RROP1 gene circuit responsive to pro-inflammatory eATP, which is itself hydrolyzed by the secreted apyrase encoded by RROP1 to dynamically control the eATP/adenosine balance in a time- and location-specific manner.

The exogenous sequences can be introduced into the microbe using molecular biological methods known in the art. In some embodiments, the engineered gene circuit is integrated into the yeast genome, e.g., using CRISPR-mediated integration, to avoid the use of antibiotic selection markers, while maintaining uracil auxotrophy for biocontainment, in agreement with Food and Drug Administration (FDA) guidelines on Live Biotherapeutic Organisms (docket number FDA-2010-D-0500). *S. cerevisiae* strains are present in healthy microbiomes and reduced during IBD (82-84), and have been associated with the physiological training the immune system (85-88).

P2Y Purinoceptor 2 (P2Y2)

The P2Y2 receptor is the most sensitive purinergic GPCR to eATP, and has previously been functionally linked to the *S. cerevisiae* mating pathway (Junger, W. G. Immune cell regulation by autocrine purinergic signalling. Nature reviews. Immunology 11, 201-212 (2011); Brown, A. J. et al. Functional coupling of mammalian receptors to the yeast mating pathway using novel yeast/mammalian G protein alpha-subunit chimeras. Yeast 16, 11-22 (2000)). The present methods can include the use of yeast engineered to express a G protein-coupled receptor (GPCR) that is activated by a pro-inflammatory signal, e.g., a P2Y2 GPCR, e.g., human P2Y2.

An exemplary reference sequence for human P2Y2 protein is provided in GenBank at NP_002555.4. Exemplary reference sequences encoding human P2Y2 protein are provided in GenBank at NM_176072.3 (variant 1); NM_002564.4 (variant 2); and NM_176071.3 (variant 3). Transcript variants 1, 2 and 3 encode the same protein. The DNA sequence of human P2Y2 used in the exemplary engineered yeast strains presented here was codon optimized for expression in yeast, with a protein sequence as shown in NP_002555.4 (NP_002555.4), optionally with up to 2%, 5%, 10%, 15%, or 20% amino acids, e.g., including or in addition to the mutations described herein.

In some embodiments, an engineered human P2Y2 is used, wherein the mutations tune the response to physiological levels of eATP, i.e., by increasing G-protein signaling and expression of the anti-inflammatory protein. In some embodiments the mutations are in residues peripheral to the ligand binding pocket (A76$^{2.47}$, N116$^{3.35}$, C119$^{3.38}$, L162$^{4.54}$, Q165$^{4.57}$), or residues located in the intracellular facing side of the receptor (F58$^{1.57}$, L59$^{1.58}$, C60$^{1.59}$, A229$^{ICL3}$, K240$^{6.31}$, F307$^{7.54}$, G310$^{C\text{-}term}$). In some embodiments, the P2Y2 includes one or more mutations in residues that contributed the most to the increase in eATP sensitivity (i.e. F58$^{1.57}$, N116$^{3.35}$, F307$^{7.54}$ and Q165$^{4.57}$), e.g., one or more mutations in residues F58 (e.g., F58C), Q165 (e.g., Q165H), and F307 (e.g., F307S). In some embodiments, the mutations include a mutation at N116, e.g., N116S, optionally in combination with mutations at either F58, e.g., F58I, or F307, e.g., F307S. In some embodiments, the P2Y2 includes mutations at L59, e.g., L59I, and/or C119, e.g., C119S. In addition to the specific mutations described herein, mutations to other amino acids can also be used, e.g., F58 can be changed to any other amino acid. (Numbering corresponds to NP_002555.4-SEQ ID NO:13)

Anti-Inflammatory Agents

The microbes described herein are engineered to express one or more anti-inflammatory agents. Exemplary anti-inflammatory agents include apyrase, interleukin-10 (IL-10), IL-2, IL-27, IL-22, and IFN-beta. The anti-inflammatory agents are placed under the control of a promoter that is triggered by binding of eATP to the GPCR P2Y2, which (without wishing to be bound by theory) causes G protein mediated triggering of the MAP Kinases cascade and expression of the anti-inflammatory agents. Exemplary promoters include pFUS1 (defined as the 1636 bp immediately upstream of the Fus1 start codon; Gene ID 850330, GenBank Acc. No. NC_001135.5, Range 71803-73341), or pFIG. 1 (defined as the 500 bp immediately upstream of the Fig1 start codon; Gene ID 852328, GenBank Acc. No. NC_001134.8, Range 316968-317864). Alternatively a synthetic transcription factor containing a pheromone responsive domain and a DNA binding domain, paired with non-yeast DNA operator sequences upstream of the anti-inflammatory gene, similar to those described by Mukherjee et al., ACS Synth. Biol. 2015, 4, 12, 1261-1269 (2015) and Shaw et al. Cell. 177 (3): 782-796.e27 (April 2019), can be used.

Apyrase (RROP)

In mouse models of IBD and chronic inflammation, intraperitoneal injection of apyrase reduces T cell activation, prevents the production of pro-inflammatory cytokines, and attenuates colitis (Wan, P. et al. Extracellular ATP mediates inflammatory responses in colitis via P2×7 receptor signaling. Sci Rep 6, 19108 (2016); Atarashi, K. et al. ATP drives lamina propria T (H) 17 cell differentiation. Nature 455, 808-812 (2008); Cauwels, A., Rogge, E., Vandendriessche, B., Shiva, S. & Brouckaert, P. Extracellular ATP drives systemic inflammation, tissue damage and mortality. Cell death & disease 5, e1102 (2014)). Apyrase degrades pro-inflammatory ATP, assisting in its conversion to an anti-inflammatory signal, adenosine (Cekic, C. & Linden, J. Purinergic regulation of the immune system. Nature reviews. Immunology 16, 177-192 (2016)).

Apyrase isolated from the potato species *S. tuberosum* (RROP1; GenBank accession U58597.1) has the highest ATPase activity reported (115). The BlastPhyMe tool was employed for genome mining of homologous genes (116), using RROP1 as the initial input sequence. Apyrase from wild einkorn wheat *Triticum urartu* (named "TUAP1" and used in the examples described herein), was eventually selected as it had conserved domains known to be required for apyrase function (Knowles, Purinergic Signal. 2011 March; 7 (1): 21-45), and based on previous reports of wheat apyrase activity (Komoszynski Comp Biochem Physiol B Biochem Mol Biol. 1996 March; 113 (3): 581-91); see GenBank accession KD039156.1). The DNA sequences of *S. tuberosum* (RROP1) and *Triticum urartu* (TUAP1) used in the exemplary engineered yeast strains presented here were codon optimized for expression in yeast (see below). In addition, the endogenous apyrase N-terminal signal peptide (e.g., the first 30 nucleotides of U58597.1, or first 18 amino acids of KD039156.1) can be replaced by a yeast secretion signal, e.g., MFα1 signal peptide (first 85 or first 89 amino acids of NP_015137.1, depending on if Ste13 cut site is desired). Other signal sequences can alternatively be used, e.g., from pre-pro-α-factor, see, e.g., Wittke et al., Mol Biol Cell. 2002 July; 13 (7): 2223-2232; Microb Cell Fact. 2014; 13:125; or the BGL2 signal peptide (or the artificial BGL2 pre-Val7 variant) (see Achstetter et al., Gene 110 (1): 25-21, 2 Jan. 1992); or the AGA2 or EXG1 signal peptide sequences (see Mori et al., J. Biosci. Bioeng. 2015; 120 (5): 518-525); or engineered peptide sequences not found in nature (see Rakestraw et al., Biotechnol. Bioeng. 2009; 103 (6): 1192-1201).

Interleukin 10 (IL-10)

IL-10 is required for the proper regulation of inflammation, acting to downregulate pro-inflammatory genes (Paul, G., Khare, V. & Gasche, C. Inflamed gut mucosa: downstream of interleukin-10. Eur J Clin Invest 42, 95-109 (2012)). Delivery of IL-10 has been explored as a treatment for IBD, but its efficacy may be limited by a low concentration once it reaches the gut (Marlow, G. J., van Gent, D. & Ferguson, L. R. Why interleukin-10 supplementation does not work in Crohn's disease patients. World J Gastroenterol 19, 3931-3941 (2013)).

An exemplary reference sequence for human IL-10 protein is provided in GenBank at NP_000563.1 (interleukin-10 isoform 1 precursor) and for mouse IL-10 (mIL-10) NP_034678.1 (interleukin-10 precursor); exemplary DNA reference sequences encoding these two are provided in GenBank at NM_000572.3 and NM_010548.2, respectively. The DNA sequence of mIL-10 used in the exemplary engineered yeast strains presented here was codon optimized for expression in yeast. The endogenous IL-10 N-terminal signal peptide (first 21 amino acids of NP_034678.1) can be replaced by a yeast secretion signal, e.g., MFα1 signal peptide (first 85 or first 89 amino acids of NP_015137.1, depending on if Ste13 cut site is desired). Other signal sequences can alternatively be used, e.g., from pre-pro-a-factor, see, e.g., Wittke et al., Mol Biol Cell. 2002 July; 13 (7): 2223-2232; Microb Cell Fact. 2014; 13:125; or the BGL2 signal peptide (or the artificial BGL2 pre-Val7 variant) (see Achstetter et al., Gene 110 (1): 25-21, 2 Jan. 1992); or the AGA2 or EXG1 signal peptide sequences (see Mori et al., J. Biosci. Bioeng. 2015; 120 (5): 518-525); or engineered peptide sequences not found in nature (see Rakestraw et al., Biotechnol. Bioeng. 2009; 103 (6): 1192-1201).

See also WO2007039586.

Interleukin-2 (IL-2)

Low dose IL-2 has been shown to expand Tregs and ameliorate disease in a humanized mouse model of experimental colitis. Goettel et al., Cell Mol Gastroenterol Hepatol. 2019; 8 (2): 193-195.

An exemplary reference sequence for human IL-2 protein is provided in GenBank at NP_000563.1; an exemplary human reference sequence encoding IL2 is provided at NM_000586.4, optionally including a yeast secretion signal as described above.

IL-27

An exemplary reference sequence for human IL-27 protein is provided in GenBank at NP_663634.2; an exemplary human reference sequence encoding IL-27 is provided at NM_145659.3, optionally including a yeast secretion signal as described above. IL-27 therapy has been suggested as a treatment for IBD; see Andrews et al., Inflamm Bowel Dis. 2016 September; 22 (9): 2255-2264.

IL-22

An exemplary reference sequence for human IL-27 protein is provided in GenBank at NP_065386.1; an exemplary human reference sequence encoding IL-27 is provided at NM_020525.5, optionally including a yeast secretion signal as described above. IL-22 therapy has been suggested as a treatment for IBD; see Li et al., World J Gastroenterol. 2014 Dec. 28; 20 (48): 18177-18188.

Interferon Beta 1 (IFN-Beta)

An exemplary reference sequence for human IL-27 protein is provided in GenBank at NP_002167.1; an exemplary human reference sequence encoding IL-27 is provided at NM_002176.4, optionally including a yeast secretion signal as described above. Interferon β-1a is in clinical trials for IBD, e.g., in ulcerative colitis; see, e.g. Nikolaus et al., Gut. 2003 September; 52 (9): 1286-1290.

Codon Optimization and Variants

In addition, the nucleic acid sequences used in the present methods and compositions are preferably codon-optimized for expression in a selected expression system, e.g., in *S. cerevisiae*. In order to optimize expression in non-mammalian cells, codon optimization specific for a selected host organism can be used. For example, in embodiments where *S. cerevisiae* is used as a host organism, the following Table A (source: kazusa.or.jp) can be used to select codons:

TABLE A

| *Saccharomyces cerevisiae* codon frequency | | | |
|---|---|---|---|
| fields: [frequency: per thousand] ([number]) | | | |
| UUU 26.1(170666) | UCU 23.5(153557) | UAU 18.8(122728) | UGU 8.1(52903) |
| UUC 18.4(120510) | UCC 14.2(92923) | UAC 14.8(96596) | UGC 4.8(31095) |
| UUA 26.2(170884) | UCA 18.7(122028) | UAA 1.1(6913) | UGA 0.7(4447) |
| UUG 27.2(177573) | UCG 8.6(55951) | UAG 0.5(3312) | UGG 10.4(67789) |
| CUU 12.3(80076) | CCU 13.5(88263) | CAU 13.6(89007) | CGU 6.4(41791) |
| CUC 5.4(35545) | CCC 6.8(44309) | CAC 7.8(50785) | CGC 2.6(16993) |
| CUA 13.4(87619) | CCA 18.3(119641) | CAA 27.3(178251) | CGA 3.0(19562) |
| CUG 10.5(68494) | CCG 5.3(34597) | CAG 12.1(79121) | CGG 1.7(11351) |
| AUU 30.1(196893) | ACU 20.3(132522) | AAU 35.7(233124) | AGU 14.2(92466) |
| AUC 17.2(112176) | ACC 12.7(83207) | AAC 24.8(162199) | AGC 9.8(63726) |
| AUA 17.8(116254) | ACA 17.8(116084) | AAA 41.9(273618) | AGA 21.3(139081) |
| AUG 20.9(136805) | ACG 8.0(52045) | AAG 30.8(201361) | AGG 9.2(60289) |
| GUU 22.1(144243) | GCU 21.2(138358) | GAU 37.6(245641) | GGU 23.9(156109) |
| GUC 11.8(76947) | GCC 12.6(82357) | GAC 20.2(132048) | GGC 9.8(63903) |
| GUA 11.8(76927) | GCA 16.2(105910) | GAA 45.6(297944) | GGA 10.9(71216) |
| GUG 10.8(70337) | GCG 6.2(40358) | GAG 19.2(125717) | GGG 6.0(39359) |

Figure 12:
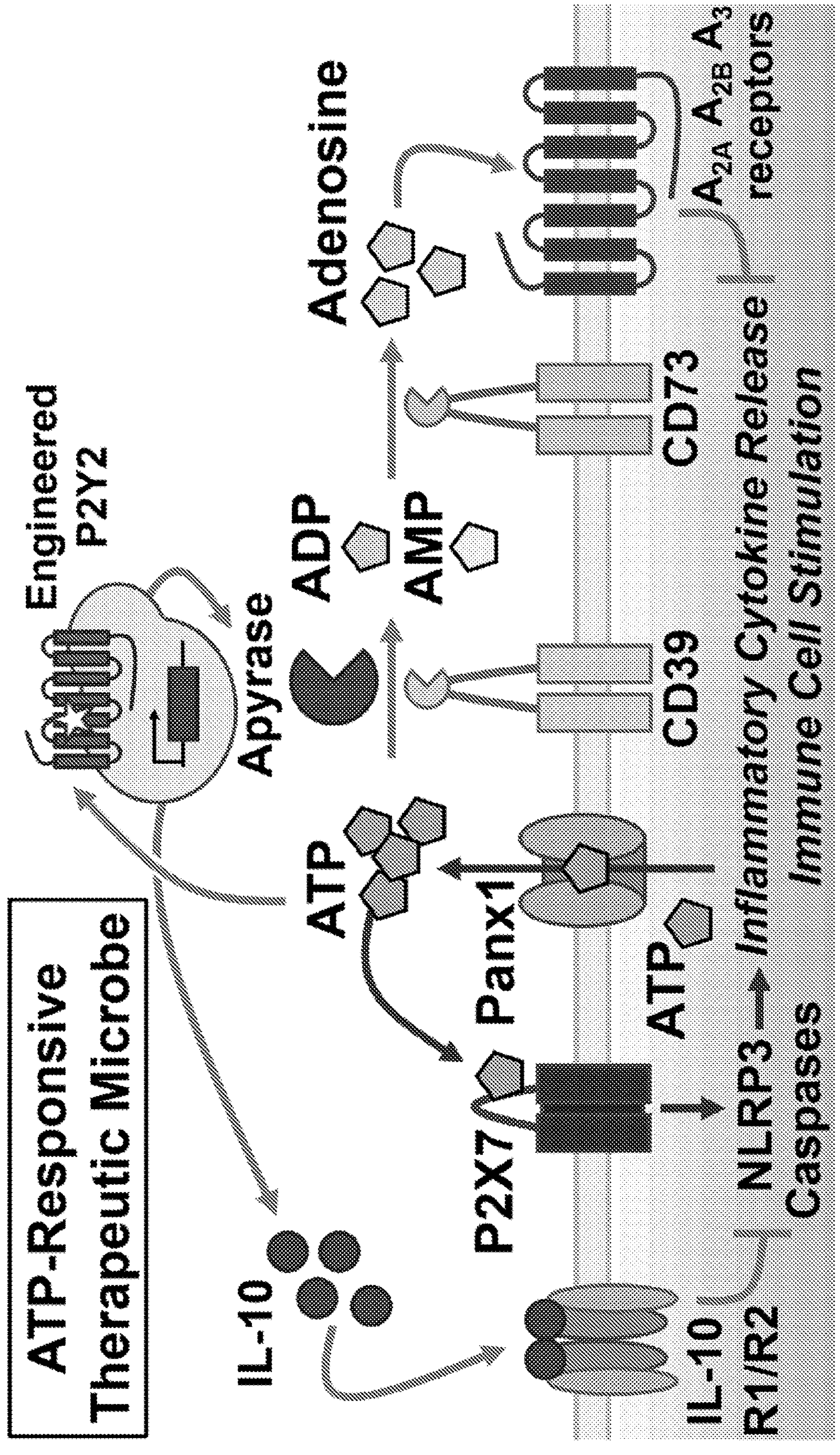
FIG. 12. How an ATP-Responsive Therapeutic Microbe Regulates Purinergic Signaling During Inflammation. Chronic inflammation is characterized by upregulated extracellular ATP (eATP), reaching >100 μM surrounding inflamed tissue (Bours, M. J., Dagnelie, P. C., Giuliani, A. L., Wesselius, A. & Di Virgilio, F. P2 receptors and extracellular ATP: a novel homeostatic pathway in inflammation. Frontiers in bioscience 3, 1443-1456 (2011), Di Virgilio, F., Pinton, P. & Falzoni, S. Assessing Extracellular ATP as Danger Signal In Vivo: The pmeLuc System. Methods in molecular biology 1417, 115-129 (2016)). eATP induces pro-inflammatory responses from a variety of immune and epithelial cells in the gut, primarily mediated through the P2X7 receptor (Kurashima, Y., Kiyono, H. & Kunisawa, J. Pathophysiological role of extracellular purinergic mediators in the control of intestinal inflammation. Mediators of inflammation 2015, 427125 (2015)). Activation of P2X7 promotes caspase-1 expression, leading to maturation of inflammatory cytokines and opening of pannexin-1 (Panx1) channels, facilitating efflux of additional ATP (Cekic, C. & Linden, J. Purinergic regulation of the immune system. Nature reviews. Immunology 16, 177-192 (2016)). To prevent eATP accumulation, ectonucleotidases CD39 and CD73 degrade ATP into ADP, AMP, and finally adenosine (Cekic, C. & Linden, (2016)). The A2A, A2B, and A3 receptors are GPCRs primarily expressed by immune cells, and their activation by adenosine leads to anti-inflammatory responses (Cekic, C. & Linden, (2016)). The invention, an eATP-responsive therapeutic microbe, dynamically modulates these existing immunoregulatory pathways. After being introduced to the GI tract, the yeast cells can sense upregulated eATP via the engineered P2Y2 receptors expressed on their surface. P2Y2 activates the rewired mating pathway, secreting apyrase or mouse IL-10 in an eATP concentration dependent manner. Apyrase functions to directly degrade eATP, shutting off the P2Y2-activating signal while helping to generate anti-inflammatory adenosine. IL-10 acts on the IL-10 R1/R2 receptors which lead to the downregulation of many pro-inflammatory genes (Paul, G., Khare, V. & Gasche, C. Inflamed gut mucosa: downstream of interleukin-10. Eur J Clin Invest 42, 95-109 (2012)), including the NLRP3 inflammasome and caspases (Gurung, P. et al. Chronic TLR Stimulation Controls NLRP3 Inflammasome Activation through IL-10 Mediated Regulation of NLRP3 Expression and Caspase-8 Activation. Sci Rep 5, 14488 (2015); Zhang, J., Fu, S., Sun, S., Li, Z. & Guo, B. Inflammasome activation has an important role in the development of spontaneous colitis. Mucosal Immunol 7, 1139-1150 (2014)).

In some embodiments, the methods include variants of a reference sequence as described herein. Thus, in some embodiments, the sequence can be at least 80%, 85%, 90%, 95%, or 99% identical to at least 60%, 70%, 80%, 90%, or 100% of a reference sequence; e.g., the sequence can include 1, 2, 3, 4, 5, 6, 7, 8, 9, 10, 11, 12, 13, 14, 15, 16, 17, 18, 19, or 20 mutations, e.g., in addition to a mutation described herein, so long as the additional mutations don't significantly reduce a relevant activity of the protein (e.g., for P2Y2, the ability to sense eATP and trigger expression and secretion of the anti-inflammatory; for apyrase, the ability to degrade eATP; for IL-10, the ability to downregulate inflammatory genes, e.g., as shown in FIG. 12, and so on). To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is typically at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. In another embodiment, the percent identity of two amino acid sequences can be assessed as a function of the conservation of amino acid residues within the same family of amino acids (e.g., positive charge, negative charge, polar and uncharged, hydrophobic) at corresponding positions in both amino acid sequences (e.g., the presence of an alanine residue in place of a valine residue at a specific position in both sequences shows a high level of conservation, but the presence of an arginine residue in place of an aspartate residue at a specific position in both sequences shows a low level of conservation).

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Methods of Treatment

The gut microbiome plays central roles in health and disease (67). Based on the multiple functions performed by the microbiome, the use of engineered probiotics is considered an attractive therapeutic approach for inflammatory diseases, among other human disorders. The engineered microbes described herein can be used, e.g., in the treatment and prophylaxis of inflammatory conditions, e.g., by administering an effective amount of the engineered microbe to the GI tract of patients, e.g., by oral ingestion of a composition comprising the engineered microbes as described herein, sufficient to reduce inflammation and treat or reduce the risk of or delay development of an inflammatory condition.

The microbes can be used, e.g., in the treatment and prophylaxis of inflammatory conditions, e.g., inflammatory gut conditions including inflammatory bowel disease (IBD) by administering the engineered microbe to the GI tract of patients, e.g., by oral ingestion of a composition comprising the engineered microbes. IBD can include Crohn's disease; ulcerative colitis (UC); microscopic colitis; diverticulosis-associated colitis; collagenous colitis; lymphocytic colitis; and Behçet's disease. The microbes can be used, e.g., in the treatment and prophylaxis of graft versus host disease (GVHD), or following anti-tumor therapy (e.g., chemotherapy, radiation therapy and checkpoint inhibitors, all of which induce GI inflammation). The microbes can be used, e.g., in the treatment and prophylaxis of GI inflammation.

eATP promotes intestinal inflammation in gut conditions including inflammatory bowel disease (IBD), as well as in other diseases besides IBD, such as graft versus host disease and irradiation-induced abdominal fibrosis (93, 94). Moreover, the intestinal microbiome controls inflammation at distant body sites such as the central nervous system (95-97). Thus, present methods can be used for the treatment and/or prophylaxis of inflammatory disorders targeting other tissues beyond the intestinal system, e.g., for the reduction of systemic inflammation.

Generally, the methods include administering an effective amount of engineered microbes as described herein, to a subject who is in need of, or who has been determined to be in need of, such treatment. The methods can include administering the microbes as often as needed to reduce inflammation, e.g., once or twice per day, e.g., one, two, three, four, five, six, or seven days a week (e.g., daily); and administration can be continued for at least one, two, three, four, five, six, seven, eight or more weeks, or indefinitely.

As used in this context, to "treat" means to ameliorate (e.g., reduce severity or frequency of) at least one symptom of the disorder associated with inflammation; administration of a therapeutically effective amount of engineered microbes as described herein can result in a decrease in one or more symptoms of a disorders associated with inflammation. As noted above, in some embodiments, the disorder is IBD. For example, Crohn's often results in frequent diarrhea; occasional constipation; abdominal pain; fever; blood in the stool; fatigue; skin conditions; joint pain; malnutrition; weight loss; and/or fistulas. UC often results in abdominal pain; loose stools; bloody stool; urgency of bowel movement; fatigue; loss of appetite; weight loss; and/or malnutrition. Administration of a therapeutically effective amount of engineered microbes can result in a reduction in any one or more of these symptoms. Administration of a prophylactically effective amount of engineered microbes as described herein can result in decreased risk or delayed development of a disorders associated with inflammation. Subjects who have a disorder associated with inflammation can be identified by one of skill in the art, e.g., using imaging methods such as colonoscopy or a CT scan. In some embodiments, subjects treated using a method described herein include those who have a risk of developing a disorder associated with inflammation, e.g., that have a risk that is higher than the risk of the general population, e.g., as a result of genetics/family history, age, race, diet, or other risk factors.

See also WO2007039586.

Compositions

Provided herein are compositions comprising the engineered microbes. Preferably the compositions are formulated for oral administration of the microbes, and include a physiologically-acceptable carrier or excipient, i.e., that is non-toxic and doesn't affect the activity of the engineered microbes.

In some embodiments, the compositions are solid forms, e.g., tablets, pills, capsules, soft gelatin capsules, sugar-coated pills, orodispersing/orodispersing tablets, effervescent tablets or other solids. In some embodiments, the compositions are in a liquid form, such as, for example, a drinkable solution.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In some embodiments, the compositions are nutritional compositions comprising liquid or solid food, feed or drinking water. In some embodiments, the compositions are food products, such as, for example, beverages including dairy and non-dairy based drinks, plant- or animal-based milk products (e.g., almond, cashew, soy, or oat milk; or cow, goat, or sheep milk), milk powder, reconstituted milk, cultured milk, smoothies or cultured beverages (resulting from fermentation of the carbohydrate containing media), flavored beverages, yogurt, drinking yogurt, set yogurt, fruit and/or vegetable juices or concentrates thereof, fruit and vegetable juice powders, reconstituted fruit products, powders, or malt or soy or cereal based beverages, and sports supplements including dairy and non-dairy based sports supplements; or solid foods including breakfast cereal such as muesli flakes, spreads, meal replacements, confectionary, chocolate, gels, ice creams, cereal, fruit puree, and/or chocolate bars, energy bars, snack bars, food bars, sauces, dips. The compositions can also be additives, e.g., to be mixed into solid food, e.g., by sprinkling onto or mixing into a food; or to be mixed into a beverage, e.g., into water, juice, or milk, and can include flavors. As used herein, a smoothie is a drink made from pureed raw fruit and/or vegetables, typically using a blender. A smoothie typically comprises a liquid base such as water, fruit juice, plant and/or animal based milk products such as milk, yogurt, ice cream or cottage cheese. Smoothies can comprise additional ingredients, e.g., crushed ice, sweeteners (e.g., natural sweeteners such as agave syrup, maple syrup, honey or sugar, or artificial sweeteners), vinegar, protein supplements such as whey powder, chocolate, or nutritional supplements, The microbes in the compositions should be viable, e.g., should either be alive or should be in a form that supports viability, e.g., in a dehydrated form that allows for the yeast to be viable when rehydrated, e.g., prepared as described in U.S. Pat. Nos. 3,843,800A1; 3,993,783A; 4,217,420A; 4,341,871A; 4,764,472; EP0616030A1; U.S. Pat. Nos. 6,033,887A; 6,372,481B1; US20050106287A1; US20050129808A1; US20100092611A1; WO2009130219A1; JP2010536360A; RU2444566C2; CN102803468A. See also WO2007039586.

EXAMPLES

The invention is further described in the following examples, which do not limit the scope of the invention described in the claims.

Materials and Methods

The following materials and methods were used in the Examples below.

Reporter yeast strains. All genome modifications of initial yeast strains were conducted using homologous recombination of selectable markers, transformed using a standard lithium-acetate transformation method with at least 1 μg of linear insert DNA. The parent strain was either CB008, for constitutive overexpression of fluorescent reporter genes (98), or BS004 for the P2Y2-mCherry or P2Y2-apyrase gene circuit (99) (see Table 1 for detailed strain genotypes). pFUS1-mCherry was integrated at the MFA2 locus using plasmid pJW609 containing the KanR marker. pFUS1 was defined as the 1636 bp immediately upstream of the Fus1 start codon, the mCherry sequence used is from Keppler-Ross, Noffz and Dean (100), and ~1 kb homology regions were used. Ste2 and Sst2 were targeted for deletion using Trp1 and HygB selectable markers respectively, each with 180 bp of flanking homology regions identical to the sequences flanking the ORF. The 5 C-terminal amino acids of Gpa1 (KIGII) were replaced with a Gpa1-Ga chimera containing the C-terminal amino acids from the indicated human Ga protein, using plasmid pBS600 containing selectable marker LEU2 and 800 bp homology regions. The *C. albicans* Adh terminator was used for the pFUS1-mCherry and Gpa1-Ga gene knock-ins. To create a strain that constitutively expresses mCherry, integration plasmid pJW609 was modified to replace the KanMX marker with HIS3 from *C. glabrata*, and pTDH3 mCherry was inserted at the PspOMI/BamHI sites. Linearized HIS3-pTDH3 mCherry cassette was transformed into strain CB008, and integrations selected by plating on SC-HIS. To create strains that contain the KanMX selectable marker and constitutively express GFP, an integration plasmid was constructed using the MoClo Yeast Toolkit (101). The resulting plasmid, pBS211, contained HO locus homology regions, the KanMX marker, and a yeast codon-optimized sfGFP gene downstream of pTDH3 (102). Linearized KanMX-pTDH3 sfGFP cassette was transformed into strains in Table 1, and integrations selected by plating on YPD-G418 sulfate (200 μg/mL). All strains were confirmed by PCR and flow cytometry.

Microscopy. Yeast strain BS016 expressing the endogenous yeast GPCR Ste2 or a yeast codon-optimized sequence of human P2Y2 (obtained from ATUM) C-terminally tagged with GFP were grown to log phase in SD-URA media. The centromere plasmid pRS316 was used, containing the endogenous Ste2 promoter for Ste2 expression, or pTDH3 for P2Y2 expression, and the GFP sequence used is from (103). Restriction enzyme sites introduced an amino acid linker (GGERGS) between the final GPCR residue and first GFP residue. Cells were plated on glass-bottomed dishes (Greiner Bio-One) that had been treated with concanavalin A (Sigma-Aldrich), then covered with 1 mL SD-URA media. Cells were imaged using a Leica TCS SP8 confocal microscope.

Flow cytometry evaluation of response to ATP and UTP. Yeast strain BS016 transformed with a human P2Y2 gene in the pRS316 pTDH3 vector was grown in SC-URA liquid media overnight. The same strain transformed with a plasmid not containing a P2Y2 sequence (Vector) was used as a negative control. Cells were diluted to $OD_{600}$ 0.05 in 600 μL SC-URA containing ATP (0-25.6 mM; pH 7.0, Bio Basic) or UTP (0-3.2 mM; pH 7.0, Sigma-Aldrich) and incubated for 6 hours at 30° C. Cells were then treated with cycloheximide to a final concentration of 10 μg/mL. The mCherry signal of at least 10,000 cells was measured for each sample with a Miltenyi Biotec MACSQuant VYB. The mean mCherry fluorescence was determined using FlowJo. For dose-response assays, data was fitted with the "log (agonist) vs. response-Variable slope (four parameters)" model in Prism (GraphPad). After subtracting the mCherry fluorescence signal of the Vector control, fluorescence values were normalized to the wild-type P2Y2 control used in the same experiment, to allow comparisons between experiments performed on different days.

Figure 8:
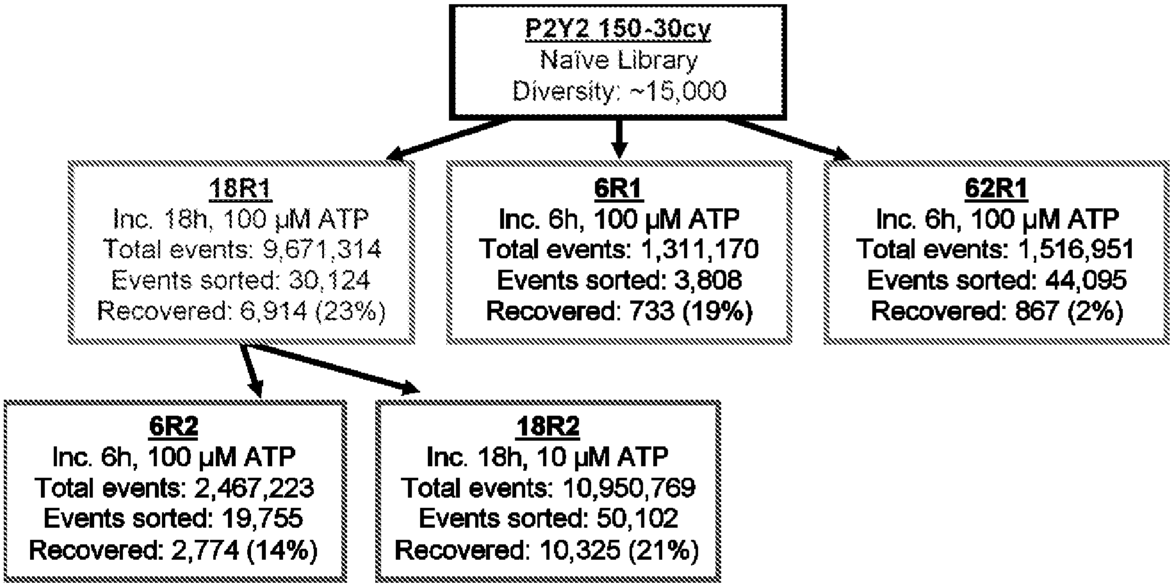
FIG. 8: Strategy for directed evolution of human P2Y2 receptor. During each FACS sort the top ~1% of mCherry fluorescence was collected. "Recovered" refers to the number of yeast colonies obtained after plating sorted cells on selective media.

Directed evolution of human P2Y2 receptor. Error-prone PCR mutagenesis was performed using the Agilent GeneMorph II Random Mutagenesis Kit with yeast codon-optimized human P2Y2 as a template, using previously described methods (104). 150 ng of template DNA and 30 cycles achieved the desired mutation rate of ~3 mutations per P2Y2 gene, determined by sequencing 12 randomly selected plasmids (Table 2). The random mutants were inserted into pRS316 pTDH3 using AarI-based cloning and transformed into NEB 5-alpha competent *E. coli* cells (New England Biolabs) generating >15,000 individual colonies. Cells were scraped off agar plates, mixed together, and plasmid DNA was extracted (QIAQuick Spin Miniprep Kit, Qiagen) to create the final plasmid library. The library was transformed into yeast strain BS016 using a high-efficiency lithium acetate-based method (105), yielding at least 10-fold the number of colonies as the total library size, so that each mutant would be screened multiple times. Transformed cells were incubated overnight, then diluted to $OD_{600}$ 0.05 into fresh 100 mL SC-URA liquid media containing 100 μM ATP (pH 7.0, Biobasic), and incubated for either 18 or 6 hours at 30° C. (FIG. 8). After brief sonication, $10^6$-$10^7$ cells were gated by side and forward scatter and sorted for the highest ~1% of mCherry signal using a BD Influx cell sorter (106). A total of 174 yeast colonies recovered from various sorting experiments were individually screened for their response to 100 M UTP, 100 UM ATP, or with no ligand, after a 6-hour incubation. Plasmids were isolated from selected colonies by first incubating with zymolase (BioShop Canada) then extracting plasmid DNA (QIAQuick Spin Miniprep Kit, Qiagen). Plasmid DNA was amplified using NEB 5-alpha competent *E. coli* cells (New England Biolabs), the plasmid DNA was sequenced, and fresh BS016 yeast cells were transformed for dose-response experiments.

Homology modeling of P2Y2. Modeling was conducted as described Rafehi, Neumann, Baqi, Malik, Wiese, Namasivayam and Muller (107) using the crystal structure of the human P2Y1 receptor (4XNW.pdb) bound to the nucleotide antagonist MRS2500 as a template. The sequences of human P2Y1 and P2Y2 were aligned using Clustal Omega. As only residues S38 to F331 of P2Y1 were visible in the crystal structure, these were used as the template to generate 500 models of the corresponding P2Y2 residues L20 to L313. Standard MODELLER 9.18 settings were used, maintaining MRS2500 in the models (108). The generated models were first analyzed based on the DOPE and GA341 scores, and the top five models were manually inspected to ensure the natural disulphide bonds were maintained (C25-C278, C106-C183). Next, models were evaluated by ProSA-WEB (109) and Ramachandran plots (110), and the final model was selected. ATP was docked to the wild-type P2Y2 homology model using the Galaxy7™ web server (111), which generated 10 docked models. The lowest energy model in which the adenine ring of ATP was oriented towards the key Y114 and F261 residues was selected (107). Publication quality images were generated with PyMOL (Schrödinger, Inc.).

Figure 11:
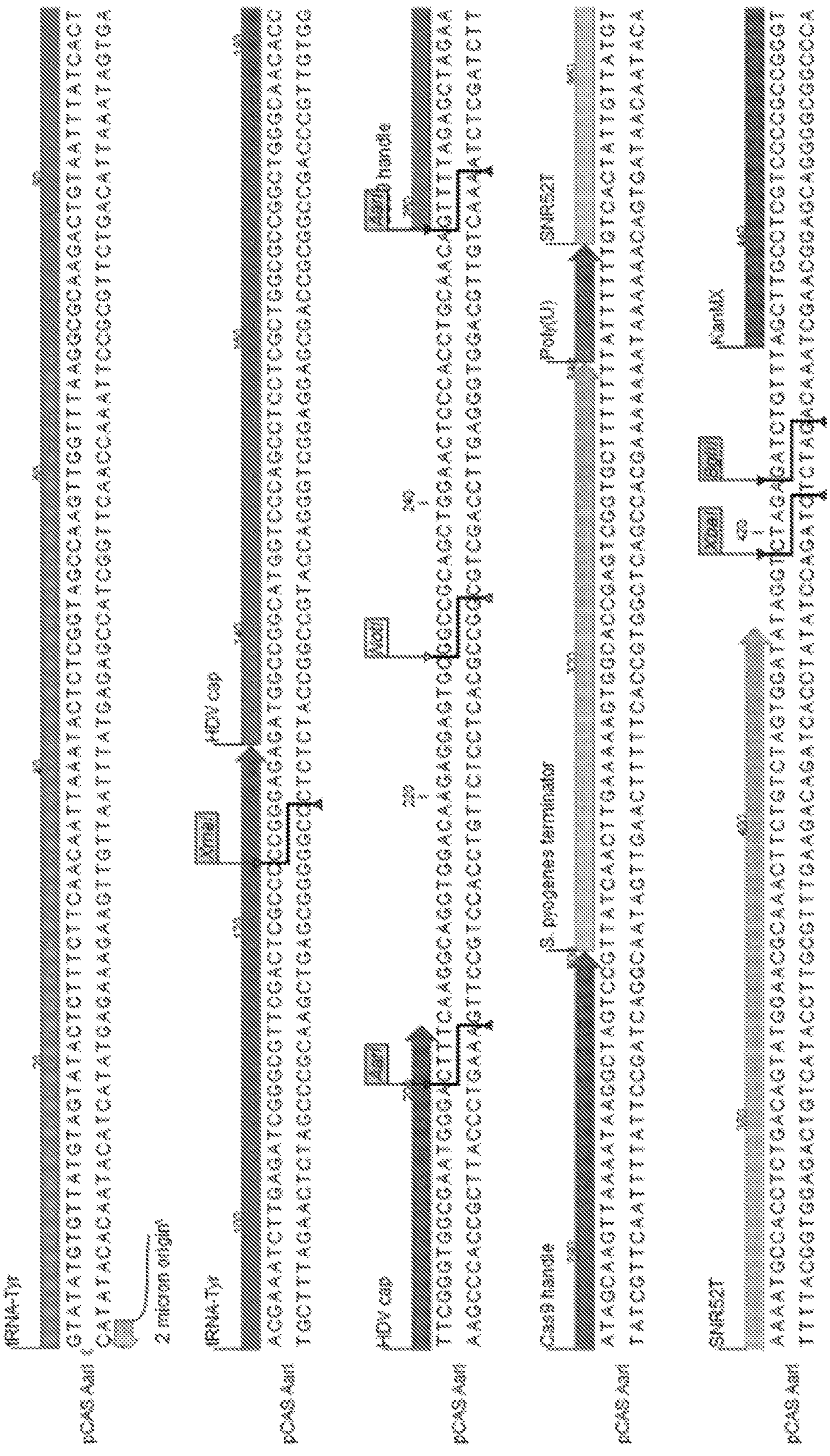
FIG. 11: Plasmid pCAS AarI. Custom multiple cloning site inserted at the XmaI and BglII sites in the pCAS plasmid, obtained from AddGene (112). Shown is SEQ ID NO: 22. Image generated with CLC Sequence Viewer.

Integration of P2Y2 mutants with CRISPR. The pCAS plasmid was obtained from AddGene, which expresses Cas9 and a yeast-optimized guide RNA (gRNA) (112). The gRNA sequence was replaced with an AarI-based multiple cloning site, to generate the pCAS AarI plasmid (FIG. 11). This enabled the use of AarI, a type IIS restriction enzyme, to insert any gRNA sequence (20 bp) without modifying the required nuclear localization signal or 3' tail of the gRNA. gRNA sequences were designed with CRISPR MultiTargeter (113) and Off-Spotter web servers (114).

| gRNA Name | gRNA Sequence | # | NNNN-Target-PAM-NNN | # |
|---|---|---|---|---|
| HygB g1143 | ACAAATCGCCCGCAGAAGCG | 1 | GTAC**ACAAATCGCCCGCAGAAGCG**CGGCCG | 2 |
| mCherry g664 | GCTGAAGGTAGACATTCAAC | 3 | AAGA**GCTGAAGGTAGACATTCAAC**TGGTGG | 4 |

#, SEQ ID NO:

#, SEQ ID NO:

The forward oligos were ordered with CTTT 5' overhang, and reverse oligos were ordered with AAAC 5' overhang to facilitate ligation to plasmid pCAS AarI following digestion with AarI enzyme.

A gene cassette containing an engineered P2Y2 mutant downstream of the pTDH3 promoter was assembled in the plasmid pBS600, flanked by 800 bp homology arms for the SST2 locus. The cassettes were amplified by PCR and transformed into strain BS021 along with plasmid pCAS AarI HygB 1143 as described Ryan, Skerker, Maurer, Li, Tsai, Poddar, Lee, DeLoache, Dueber, Arkin and Cate (112). Colonies were screened for mCherry expression in response to ATP, and P2Y2 integration was confirmed by sequencing.

Apyrase genome mining. Apyrase isolated from the potato species *S. tuberosum* (RROP1; GenBank accession U58597.1) has the highest ATPase activity reported (115). The BlastPhyMe tool was employed for genome mining of homologous genes (116), using RROP1 as the initial input sequence. Apyrase from wild einkorn wheat *Triticum urartu* (named "TUAP1" in our study; GenBank accession KD039156.1) was selected as it had conserved domains known to be required for apyrase function (115), and based on previous reports of wheat apyrase activity (117). Yeast codon optimized RROP1 and TUAP1 were modified to contain a N-terminal alpha factor signal peptide (first 85 amino acids of the yeast MFα1 gene, lacking Ste13 cut site) and a C-terminal HA tag (gene synthesis by ATUM).

Integration of apyrase genes into the genome of P2Y2 strains. A gene cassette containing one of the apyrase genes downstream of the pFUS1 promoter was assembled in the plasmid pBS600. The cassettes were amplified by PCR and transformed into a strain where P2Y2 had previously been integrated, along with plasmid pCAS AarI mCherry g664 as outlined by Ryan, Skerker, Maurer, Li, Tsai, Poddar, Lee, DeLoache, Dueber, Arkin and Cate (112). The promoter and terminator of the cassette functioned as homology arms, as mCherry had previously been inserted with pFUS1 and the *C. albicans* Adh terminator at the MFA2 locus. Colonies were screened for mCherry expression in response to ATP, and apyrase integration was confirmed by sequencing colonies that did not express mCherry. A second group of gene cassettes was assembled using plasmid pBS603 (pBS600 containing a HIS3 selection marker), with one of the apyrase genes downstream of the pTDH3 promoter, flanked by 1 kb homology arms for the MFA2 locus. The cassettes were amplified by PCR and transformed into strain CB008, before plating on selective media, to create strains BS029 (pTDH3 RROP1) and BS030 (pTDH3 TUAP1).

Western blot. Overnight cultures were diluted to $OD_{600}$ 0.05 in 50 mL YPD. ATP was added to 400 μM to induce apyrase expression in the initial media, and again at hour 6, and at hour 22 (final concentration of 1200 μM assuming no ATP was degraded). All cultures were incubated for 24 hours at 30° C. with shaking (225 rpm). Samples of lysed cells were resolved on a 10% SDS-PAGE gel (Bio-Rad) and transferred to a PVDF membrane using a Bio-Rad Trans-Blot Turbo. Membranes were blocked overnight with Odyssey® Blocking Buffer (TBS) (LI-COR Biosciences). The following primary antibodies were used: rabbit anti-HA tag (C29F4, Cell Signaling Technology), mouse anti-PGK (459250, Invitrogen). After washing, the following secondary antibodies were used: IRDye® 680LT Goat anti-Mouse IgG (926-68020, LI-COR Biosciences), IRDye® 800CW Goat anti-Rabbit IgG (926-32211, LI-COR Biosciences). Bands were visualized with a Licor Odyssey CLx infrared imaging system (LI-COR Biosciences).

Induction of apyrase secretion with ATP. Yeast strains containing a P2Y2 mutant gene and pFUS1 regulating the expression of RROP1 apyrase were incubated overnight in YPD media. Cells were diluted to $OD_{600}$ 0.05 in 2 mL fresh YPD, with 0-500 μM ATP (pH 7.0) added. After incubation for 16 hours at 30° C. with shaking (225 rpm) to $OD_{600}$ 3.5, 500 μL samples were pipetted into 1.5 mL tubes and centrifuged at 2000×g for 5 minutes to pellet cells. Culture supernatants were then evaluated for ATPase activity.

Quantification of secreted ATPase activity. The amount of ATP remaining following incubation with apyrase was determined by KinaseGlo Plus luminescence as previously described (118). In a white 96-well microplate (#655075, Greiner Bio-One) 5 μL of raw supernatant from yeast cultures at $OD_{600}$ 3.5, where ATP had been added at the start of culturing, was mixed with 50 μM ATP (pH 7.0) in assay buffer (60 mM HEPES pH 6.0, 2 mM $MgCl_2$, 2 mM $CaCl_2$), 1 mM dithiothreitol, 0.1 mg/mL bovine serum albumin, 0.1 mM EDTA, and 0.01% Tween-20) to a final volume of 50 μL. The reaction was incubated for 30 minutes at 30° C., and quenched by addition of 50 μL KinaseGlo Plus (Promega). Luminescence was measured with a Fluoroskan Ascent FL microplate reader (Thermo Fisher Scientific). ATPase activity was compared to that of commercial potato apyrase (A6410, Sigma-Aldrich), incubated with ATP under the same conditions. "Percent ATP degraded" was calculated by comparing to 50 μM ATP incubated in YPD media and assay buffer under the same conditions.

Yeast cultures for in vivo testing. Yeast strains were cultured in 550 mL or 1 L YPD media (BioShop Canada) at 30° C. with shaking (225 rpm). 200 μg/mL G418 sulfate antibiotic (BioShop Canada) was added to media when culturing strains containing the KanMX resistance marker. After 24 hours, cultures were centrifuged and yeast were resuspended in fresh YPD to an $OD_{600}$ of 92, or approximately $2\times10^9$ cfu/mL, and colony density was confirmed by plating. Yeast were stored as 800 μL aliquots at −80° C. for up to one year.

Mice. C57BL/6J female (for DSS model) or males (for TNBS model) mice between 8-10 weeks of age were used throughout the study. Mice were obtained from the Jackson Laboratory. All experiments were carried out in accordance with guidelines prescribed by the Institutional Animal Care and Use Committee (IACUC) at Brigham and Women's Hospital and Harvard Medical School.

Dextran sodium sulfate (DSS)-induced mouse colitis model. IBD was induced by adding 4% of dextran sulfate sodium salt (DSS colitis grade; MP Biomedicals) in the drinking water. Treatment was maintained for 7 days and two cycles were performed with a week without treatment in between. After the second cycle of DSS, DSS was removed and mice were sacrificed. Animal body weight was evaluated daily throughout the study.

Trinitrobenzenesulfonic acid (TNBS)-induced mouse colitis model. To induce TNBS colitis in C57BL/6J, males were pre-sensitized one week before the colitis induction by applying 150 μL of pre-sensitization TNBS solution (64% acetone (#179124, Sigma Aldrich), 16% olive oil (Sigma Aldrich #O1514), 20% of 50 mg/mL TNBS (Picrylsulfonic acid solution 5% Sigma Aldrich #P2297)) on their preshaved back. One week after, pre-sensitized mice were fasted for 4 hours and subsequently 100 μL of TNBS induction solution (50% ethanol, 50% 50 mg/mL TNBS). Was administered rectally. Control group was treated only with 50% Ethanol. Mice weight was monitored daily until the day of the euthanasia 72 hours after the colitis induction at the peak of the disease.

Mice treatment with yeasts: Both DSS and TNBS mice were given $2\times10^8$ cfu of the corresponding yeast strain by oral gavage for the whole length of the experiment meaning from day 0 for DSS mice and from the day of pre-sensitization for TNBS mice. For yeasts culture from feces studies, mice were gavaged once. For mCherry and ATP measurements studies mice were gavages for 3 days before the study with $2\times10^8$ cfu of the corresponding yeasts.

Yeast culture from mice feces: CB008, BS029 and APTM-3 yeasts expressing the resistance gene to the antibiotic $G_{418}$ were administered by oral gavage as above. Feces were collected 2, 4 and 6 hours after the gavage, weighted, homogenized in PBS and cultured at 30° C. in YPD agar (cat number #Y1500-Sigma Aldrich) containing 500 μg/mL of $G_{418}$ (cat number #A1720-Sigma Aldrich). Colony Forming Units (CFUs) were quantified after 72 hours.

ATP measurement in fecal content: In order to evaluate the ATP amount in the fecal content, feces from duodenum, jejunum, ileum, cecum and colon of TNBS mice treated with the corresponding yeast strain was collect 72 hours after TNBS induction, 2 hours after the last gavage the yeasts. The fecal content of the corresponding part of the gut was homogenized in PBS and the ATP measurement was performed using ATP determination kit (#A22066, Molecular Probes) following manufacturer's instructions. Data was normalized to weight of the fecal content and to the control sample.

mCherry Reporter Yeast Strains Detection In Vivo

To confirm the response to ATP of our engineered P2Y2 mutant in vivo, reporter yeasts expressing the mCherry under the control of the most efficient P2Y2 mutant (see above) and constitutive GFP were administered as above to TNBS colitis mice at the peak of the disease when we expect more ATP to be present in the gut. Content from the specified section of the gut was collected 2 hours after the gavage, homogenized in YPD media (#Y1375, Sigma-Aldrich) and cultured overnight. GFP and mCherry expression was measured by flow cytometry in a Fortessa flow cytometer (BD Biosciences) and the data analysis were performed at using FlowJo 10.6.1. software.

16S microbiome sequencing and analysis: Fecal samples were collected from control and TNBS colitis mice from each respective yeast treatment at the end of the study. DNA was extracted using the DNeasy PowerLyzer PowerSoil kit (#12855, Qiagen), following manufacturer's instructions. 16S rRNA gene V4 region was amplified and barcoded by PCR using HotMaster Taq DNA Polymerase and Hotmastermix (#10847-708, VWR) and a primer library that contain adaptors for MiSeq sequencing and dual index barcodes so that the PCR products can be pooled. DNA was then quantified using Quant-iT™ PicoGreen™ dsDNA Assay Kit (#P11496, Thermo Scientific) and 100 ng of each sample were pooled and cleaned-up using the QIAquick PCR Purification Kit (#28104, Qiagen). DNA was re quantified after clean-up by Qubit Fluorometric Quantification kit (Thermo Scientific) and submitted for paired-end 151 base-pair reads sequencing on the Illumina MiSeq instrument at the Harvard Medical School Biopolymer Facility as described (119). Quantitative insights for microbial ecology sofware 2 (QIIME2) was used for quality filtering and downstream analysis for Apha and Beta diversity, and compositional analysis following standardized protocols (120) (More detail here? Laurie?: Quality sequences were filtered by trimming reads below a of q20 and discarding reads shorter than 75% percent of the original length). Operational Taxonomic Units (OTUs) were picked and taxonomy was assigned. Distances between samples (β-diversity), were calculated using the phylogenetic based distance UniFrac (121). Statistical testing for differential clustering of samples on the PCoA plots was performed using the Permanova test using 999 permutations. Significant differences in taxa modulated by control or active yeast treatment was determined by linear discriminant analysis effect size (LEfSe) (122).

Cytokine quantification by ELISA. 2 cm of distal colon were extracted, thoroughly washed and cultured in RPMI supplemented with 10% FBS, 100 I.U./ml penicillin, 100 μg/ml streptomycin, 100 μg/ml of ampicillin and 50 μg/ml of kanamycin. Supernatants were collected for later ELISA analysis. ELISAs were performed following manufacturer's instructions (eBioscience).

Histological evaluation of colitis. Colonic tissue was removed and assessed for histological evaluation blindly upon Bouin's solution (Sigma-Aldrich) fixation. Paraffin-embedded tissues were sectioned, stained with hematoxylin and eosin and examined for evidence of colitis. Histology score (range: 0-6) was calculated based on the presence of lymphomononuclear cell infiltrate ('0': absence of inflammatory foci; '1': mild presence of inflammatory foci in mucosa; '2': presence of multiple inflammatory foci in mucosa and submucosa; '3': evidence of transmural infiltration) and intestinal architecture disruption ('0': normal architecture; '1': presence of focal erosions; '2': erosions and focal ulcerations; '3': extended ulceration, granulation of tissue and or pseudopolys) as previously described (Erben et al int J Clin Exp Pathol 2014).

Flow cytometry staining and acquisition. Cell suspensions were prepared from mesenteric lymph nodes. Antibodies for flow cytometry were purchased from eBioscience or BD Pharmingen and used at a concentration of 1:200 unless recommended otherwise by the manufacturer. Cells were then analyzed on a Fortessa flow cytometer (BD Biosciences and Miltenyi Biotec, respectively). Treg cells were defined as CD3+CD4+IFN-γ-IL-17-IL-10-FOXP3+.

RNA extraction and qPCR. 20 mg of the distal colon was flash frozen and later disrupted in Trizol (Invitrogen). RNA was extracted following manufacturer's instructions for miRNAeasy kit (Qiagen). When needed, to remove DSS from the RNA we further purified the mRNA using Oligotex kit (Qiagen). cDNA was prepared using High capacity RT kit (Applied Biosystems) and used for qPCR. Results were normalized to Gapdh. All primers and probes were from Applied Biosystems. Gapdh Mm99999915_g1, Il17a Mm00439618_m1, Ifng Mm00801778_m1, Foxp3 Mm00475162_m1, Ccl2 Mm00441242_m1, Nos2 Mm00440502_m1, Il1b Mm00434228_m1.

Gene expression analysis by Nanostring. 100 ng of total RNA from colon tissue was analyzed using nCounter Mouse Immunology Panel expression code sets according to manufacturer's instructions (NanoString Technologies). Data were analyzed using nSolver Analysis software and plotted with Heatmapper (123). Functional pathway enrichment analysis was conducted using Enrichr. The combined score was calculated as c=ln(p)*z where p is the p-value computed using Fisher's exact test and z is the rank score or z-score computed using a modification to Fisher's exact test in which a z-score for deviation from an expected rank is computed (124).

Gene expression analysis by RNA sequencing: 5 ng of total RNA form colon tissue was were sent for SMARTseq sequencing by the Broad Technology Labs and the Broad Genomics Platform. Processed RNA-Seq data was filtered, removing genes with low read counts. Read counts were normalized using TMM normalization and CPM (counts per million) were calculated to create a matrix of normalized expression values. The fastq files of each RNA-seq data sample were aligned to *Mus musculus* GRCm38 transcriptome using Kallisto (v0.46.1), and the same software was used to quantify the alignment results. The differential expression analysis was used to conduct using DESeq2, and the log 2 fold change was adjusted using apeGLM for downstream analysis. The Benjamini-Hochberg method was used for multiple hypothesis testing correction. The GSEA analysis was performed using the apeGLM adjusted differential expression analysis results. Genes that were differentially expressed with adjusted p values <0.05 were analyzed with the Ingenuity® Pathway Analysis (IPA) tool to determine significantly regulated pathways.

| Exemplary Sequences |
|---|
| RROP1: codon optimized with secretion signal and HA tag<br>ATGAGATTCCCATCAATCTTCACCGCAGTTCTTTTCGCAGCCTCTTCCGCACTCGCAGCCCC<br>TGTGAATACAACAACAGAAGATGAAACTGCTCAAATCCCAGCTGAAGCAGTCATTGGCTACT<br>TAGATTTGGAGGGGGATTTCGATGTTGCAGTTCTACCTTTCTCAAATTCAACAAACAATGGA<br>TTGCTGTTCATAAACACTACCATCGCTAGCATTGCAGCTAAGGAGGAGGGTGTGTCATTAGA<br>TAAGAGACAAATTCCATTACGTCGACATCTGTTAAGTCATGAATCTGAACACTACGCGGTTA<br>TCTTCGATGCAGGGTCTACAGGTTCAAGAGTACATGTTTTTCGTTTCGACGAAAAGTTAGGC<br>TTACTTCCTATTGGAAATAACATAGAATACTTCATGGCCACAGAGCCAGGTTTAAGTAGCTA<br>CGCCGAAGATCCAAAAGCTGCAGCTAACTCTTTAGAACCATTATTGGATGGTGCGGAAGGAG<br>TTGTGCCACAGGAACTACAATCAGAGACACCATTGGAACTTGGCGCTACAGCCGGTTTGAGA<br>ATGCTAAAAGGGGACGCCGCTGAGAAGATTCTCCAGGCAGTGAGAAACTTAGTGAAAAACCA<br>ATCAACATTCCATTCCAAGGATCAATGGGTGACAATCTTAGATGGTACACAAGAGGGCTCTT<br>ACATGTGGGCAGCAATTAACTATCTATTGGGCAATCTTGGGAAAGATTACAAGTCTACCACA<br>GCTACAATCGACCTAGGCGGAGGTTCCGTACAAATGGCTTACGCTATTAGTAACGAACAATT<br>TGCGAAGGCACCACAAAACGAGGACGGAGAGCCATACGTTCAACAAAAGCACTTGATGTCTA<br>AGGATTACAACTTATACGTCCATTCATACTTGAACTATGGTCAACTGGCTGGGAGAGCAGAA<br>ATCTTTAAAGCATCTAGAAACGAAAGTAACCCTTGTGCTTTGGAAGGTTGTGACGGTTATTA<br>CTCATACGGTGGCGTCGATTACAAGGTTAAGGCTCCTAAAAAGGGTTCATCTTGGAAGAGAT<br>GTAGAAGATTGACTAGACACGCTCTAAAGATCAATGCAAAATGCAATATTGAGGAATGCACT<br>TTCAATGGCGTTTGGAATGGTGGGGGTGGAGATGGACAGAAAAACATTCACGCATCCTCTTT<br>CTTTTACGATATTGGTGCTCAGGTCGGTATTGTTGATACAAAGTTTCCATCAGCTCTAGCAA<br>AGCCAATTCAATACTTAAATGCCGCAAAGGTCGCCTGCCAAACTAACGTAGCGGACATTAAG<br>AGCATATTCCCTAAAACTCAAGATAGAAATATCCCATATTTGTGTATGGACCTCATTTACGA<br>ATACACCCTTCTTGTAGATGGTTTCGGCCTAAACCCTCATAAGGAAATAACTGTTATCCATG<br>ACGTTCAGTACAAAAACTACTTGGTCGGAGCTGCCTGGCCACTGGGTTGTGCTATAGATCTC<br>GTGTCCTCTACTACAAACAAGATACGCGTTGCATCTTCTTACCCTTACGATGTCCCAGATTA<br>CGCCTGA (SEQ ID NO: 5) |
| RROP1: codon optimized with secretion signal and HAtag<br>MRFPSIFTAVLFAASSALAAPVNTTTEDETAQIPAEAVIGYLDLEGDFDVAVLPFSNSTNNG<br>LLFINTTIASIAAKEEGVSLDKRQIPLRRHLLSHESEHYAVIFDAGSTGSRVHVFRFDEKLG<br>LLPIGNNIEYFMATEPGLSSYAEDPKAAANSLEPLLDGAEGVVPQELQSETPLELGATAGLR<br>MLKGDAAEKILQAVRNLVKNQSTFHSKDQWVTILDGTQEGSYMWAAINYLLGNLGKDYKSTT<br>ATIDLGGGSVQMAYAISNEQFAKAPQNEDGEPYVQQKHLMSKDYNLYVHSYLNYGQLAGRAE<br>IFKASRNESNPCALEGCDGYYSYGGVDYKVKAPKKGSSWKRCRRLTRHALKINAKCNIEECT<br>FNGVWNGGGGDGQKNIHASSFFYDIGAQVGIVDTKFPSALAKPIQYLNAAKVACQINVADIK<br>SIFPKTQDRNIPYLCMDLIYEYTLLVDGFGLNPHKEITVIHDVQYKNYLVGAAWPLGCAIDL<br>VSSTTNKIRVASSYPYDVPDYA (SEQ ID NO: 6) |
| TUAP1: codon optimized with secretion signal and HAtag<br>ATGAGATTCCCATCAATCTTCACCGCAGTTCTTTTCGCAGCCTCTTCCGCACTCGCAGCCCC<br>TGTGAATACAACAACAGAAGATGAAACTGCTCAAATCCCAGCTGAAGCAGTCATTGGCTACT<br>TAGATTTGGAGGGGGATTTCGATGTTGCAGTTCTACCTTTCTCAAATTCAACAAACAATGGA<br>TTGCTGTTCATAAACACTACCATCGCTAGCATTGCAGCTAAGGAGGAGGGTGTGTCATTAGA<br>TAAGAGAGCCGAAATCGCTCAGGCCCGGGCAGCGGCAGTTCCTCCAGTCGGTAAGTATGCCG<br>TCATTTTAGACGCTGGTAGTACAGGTACACGTATGCATGTTTTTAGATTTGACAAGAGAATG<br>GACTTAGTAAAGATAGGGGATGATATAGAAGTGTTTGCAAAGGTCAACCCAGGTTTGAGCTC<br>ATACTCTGGTCGTCCAAAGGAAGCTACCGAGTCCATTTTACCATTGTTACAAAAGGCTAACT<br>CTGTAGTACCTCAAAGATTGATGAAAACCACCCCTGTAAAGCTTGGCGCTACAGCCGGTTTG<br>AGATTGATAGGGGATAAACAAGCTAAGCAAATCCTCGACGCGGTTAGAGGCGCTGTACACAC<br>AAACACTAAGTTTCAATACAACCCTAAATGGATTAACGTTCTTGAGGGTTCTCAGGAAGGTT<br>CCTACCTTTGGGTAGCTCTTAACTATCTATTGGATAATCTGGGGGGAGATTACTCTAAGACA<br>GTCGGAGTTATTGACTTAGGCGGTGGAAGTGTTCAAATGGCCTATGCTATTTCCCCAGCCAC<br>TGTGGTTGCCGCACCAGGTGTTCCACATGGAAAAGATCCTTACGTTACAAAGGAATACTTAA<br>AAGGTAGAGATTACAACATCTACGTCCACTCATACTTGAGATATGGAGCGCTGGCTTCCAGA<br>GTTGAAATCTTTAAAGCAAAGGAAGGCCCATTCTCTTACTGTATGTTGAGAGGCTTCAGTGG |

-continued

| Exemplary Sequences |
|---|

TAAGTACACTTACAATGGTGAAGAGTACAACGCTACAGCATCTACTGGTGGTGCACAATACG
GTAAATGCAGAGGTGATGTAATGAAGGCCCTTAAACTAGATGCCCCATGCCAAGCGAAAAAG
TGTACTTTTGATGGTGTCTGGAATGGAGGTGGAGGTCCAGGGCAAGCAAACTTGTACGTCGC
TTCTAGTTTCTACTATATGGCTTCTCAGGTTGGTCTAATCGACTCAGATGCTCCATCAGGAA
CATCTACACCAATGGCTTTCAGAGCCGTCGCACAGAAAATCTGTAGAATGTCTCTGAAGGAA
GTTAAGGCAAAGTACCCTAAGGTTAGAGATATCCCTTACATTTGCATGGATCTAGTGTATCA
ATACTCATTGTTAGTTGACGGCTTTGGTTTAGAACCTACTAAAAACATTACCCTCGTTGAAA
AGGTTAAACATGGCGAGTACTTCATTGAAGCAGCTTGGCCATTGGGCGAAGCAATTGAGGCA
GTGGCGCCGAAAAAGGGGACTTACCCATACGACGTGCCAGATTACGCCTAG (SEQ ID
NO: 7)

TUAP1: codon optimized with secretion signal and HAtag
MRFPSIFTAVLFAASSALAAPVNTTTEDETAQIPAEAVIGYLDLEGDFDVAVLPFSNSTNNG
LLFINTTIASIAAKEEGVSLDKRAEIAQARAAAVPPVGKYAVILDAGSTGIRMHVFRFDKRM
DLVKIGDDIEVFAKVNPGLSSYSGRPKEATESILPLLQKANSVVPQRLMKTTPVKLGATAGL
RLIGDKQAKQILDAVRGAVHTNTKFQYNPKWINVLEGSQEGSYLWVALNYLLDNLGGDYSKT
VGVIDLGGGSVQMAYAISPATVVAAPGVPHGKDPYVTKEYLKGRDYNIYVHSYLRYGALASR
VEIFKAKEGPFSYCMLRGFSGKYTYNGEEYNATASTGGAQYGKCRGDVMKALKLDAPCQAKK
CIFDGVWNGGGGPGQANLYVASSFYYMASQVGLIDSDAPSGTSTPMAFRAVAQKICRMSLKE
VKAKYPKVRDIPYICMDLVYQYSLLVDGFGLEPTKNITLVEKVKHGEYFIEAAWPLGEATEA
VAPKKGTYPYDVPDYA (SEQ ID NO: 8)

GPA1Gi3 chimera
ATGGGGTGTACAGTGAGTACGCAAACAATAGGAGACGAAAGTGATCCTTTTCTACAGAACAA
AAGAGCCAATGATGTCATCGAGCAATCGTTGCAGCTGGAGAAACAACGTGACAAGAATGAAA
TAAAACTGTTACTATTAGGTGCCGGTGAGTCAGGTAAATCAACGGTTTTAAAACAATTAAAA
TTATTACATCAAGGCGGTTTCTCCCATCAAGAAAGGTTACAGTATGCTCAAGTGATATGGGC
AGATGCCATACAATCAATGAAAATTTTGATTATTCAGGCCAGAAAACTAGGTATTCAACTTG
ACTGTGATGATCCGATCAACAATAAAGATTTGTTTGCATGCAAGAGAATACTGCTAAAGGCT
AAAGCTTTAGATTATATCAACGCCAGTGTTGCCGGTGGTTCTGATTTTCTAAATGATTATGT
ACTGAAGTACTCAGAAAGGTATGAAACTAGGAGGCGTGTTCAGAGTACCGGACGAGCAAAAG
CTGCTTTCGATGAAGACGGAAATATTTCTAATGTCAAAAGTGACACTGACAGAGATGCTGAA
ACGGTGACGCAAAATGAGGATGCTGATAGAAACAACAGTAGTAGAATTAACCTACAGGATAT
TTGCAAGGACTTGAACCAAGAAGGCGATGACCAGATGTTTGTTAGAAAAACATCAAGGGAAA
TTCAAGGACAAAATAGACGAAATCTTATTCACGAAGACATTGCTAAGGCAATAAAGCAACTT
TGGAATAACGACAAAGGTATAAAGCAGTGTTTTGCACGTTCTAATGAGTTTCAATTGGAGGG
CTCAGCTGCATACTACTTTGATAACATTGAGAAATTTGCTAGTCCGAATTATGTCTGTACGG
ATGAAGACATTTTGAAGGGCCGTATAAAGACTACAGGCATTACAGAAACCGAATTTAACATC
GGCTCGTCCAAATTCAAGGTTCTCGACGCTGGTGGGCAGCGTTCTGAACGTAAGAAGTGGAT
TCATTGTTTCGAAGGAATTACAGCAGTTTTATTTGTTTTAGCAATGAGTGAATACGACCAGA
TGTTGTTTGAGGATGAAAGAGTGAACAGAATGCATGAATCAATAATGCTATTTGACACGTTA
TTGAACTCTAAGTGGTTCAAAGATACACCGTTTATTTTGTTTTTAAATAAAATTGATTTGTT
CGAGGAAAAGGTAAAAAGCATGCCCATAAGAAAGTACTTTCCTGATTACCAGGGACGTGTCG
GCGATGCAGAAGCGGGTCTAAAATATTTTGAGAAGATATTTTTGAGCTTGAATAAGACAAAC
AAACCAATCTACGTGAAACGAACCTGCGCTACCGATACCCAAACTATGAAGTTCGTATTGAG
TGCAGTCACCGATCTAATCATCCAGCAAAACCTTAAAGAATGTGGTCTATATTGA (SEQ
ID NO: 9)

mIL-10_N8S codon optimized with secretion signal
ATGAGATTCCCATCAATCTTCACCGCAGTTCTTTTCGCAGCCTCTTCCGCACTCGCAGCCCC
TGTGAATACAACAACAGAAGATGAAACTGCTCAAATCCCAGCTGAAGCAGTCATTGGCTACT
TAGATTTGGAGGGGGATTTCGATGTTGCAGTTCTACCTTTCTCAAATTCAACAAACAATGGA
TTGCTGTTCATAAACACTACCATCGCTAGCATTGCAGCTAAGGAGGAGGGTGTGTCATTAGA
TAAGAGAGAGGCTGAAGCTCAATACAGTAGAGAAGATAACTCCTGCACTCATTTTCCAGTCG
GTCAATCTCATATGCTTCTAGAATTGAGAACAGCGTTTTCACAAGTAAAGACATTCTTTCAG
ACTAAAGACCAATTGGATAACATTTTACTCACTGATTCTTTGATGCAAGACTTCAAAGGCTA
CTTGGGTTGTCAGGCTTTATCCGAGATGATCCAATTCTACTTGGTAGAAGTCATGCCACAGG
CTGAAAAACACGGACCTGAGATTAAGGAACACCTTAACTCTTTAGGTGAAAAGTTGAAAACA
CTACGTATGAGACTTAGAAGATGCCATAGATTTCTGCCATGTGAGAACAAGTCTAAAGCCGT
TGAACAAGTTAAGAGTGATTTCAACAAGTTACAAGACCAGGGTGTTTATAAGGCCATGAATG
AATTTGACATTTTCATAAACTGTATTGAAGCCTACATGATGATCAAGATGAAATCTTAG
(SEQ ID NO: 10)

mIL-10_N8S codon optimized with secretion signal
MRFPSIFTAVLFAASSALAAPVNTTTEDETAQIPAEAVIGYLDLEGDFDVAVLPFSNSTNNG
LLFINTTIASIAAKEEGVSLDKREAEAQYSREDNSCTHFPVGQSHMLLELRTAFSQVKTFFQ
TKDQLDNILLTDSLMQDFKGYLGCQALSEMIQFYLVEVMPQAEKHGPEIKEHLNSLGEKLKT
LRMRLRRCHRFLPCENKSKAVEQVKSDFNKLQDQGVYKAMNEFDIFINCIEAYMMIKMKS
(SEQ ID NO: 11)

P2Y2 codon optimized DNA
ATGGCAGCTGATTTGGGACCTTGGAACGATACAATTAACGGTACTTGGGATGGTGATGAACT
AGGTTACAGATGCAGATTCAATGAGGACTTCAAGTACGTTCTACTCCCAGTATCTTACGGCG
TTGTGTGTGTCCTGGGACTTTGTCTAAACGCTGTAGCTTTGTATATCTTCTTATGCAGATTG
AAAACATGGAACGCTAGCACAACATACATGTTCCACTTGGCTGTATCAGATGCTCTTTACGC
AGCTTCACTTCCACTCTTGGTTTACTACTACGCCAGAGGTGATCATTGGCCTTTTTCAACAG
TTTTATGTAAGTTGGTGAGATTTTTGTTCTATACCAACTTGTATTGCTCTATTTTGTTTCTG -continued

| Exemplary Sequences |
|---|
| ACATGTATCTCCGTCCATAGATGTTTGGGTGTCCTCAGACCACTTAGATCACTTAGATGGG<br>GAGAGCTAGATACGCAAGACGTGTCGCTGGGGCAGTTTGGGTACTAGTTCTAGCCTGCCAAG<br>CCCCTGTTCTTTACTTCGTCACTACAAGTGCAAGAGGAGGCAGAGTTACCTGTCACGACACA<br>TCAGCGCCAGAACTATTCTCTAGATTTGTTGCATACTCCTCAGTGATGCTCGGCTTGTTGTT<br>TGCTGTTCCTTTCGCCGTCATTCTTGTCTGCTACGTACTGATGGCAAGACGTTTATTGAAAC<br>CAGCCTACGGAACTTCTGGTGGCTTACCTAGAGCAAAGAGAAAGAGTGTTAGAACCATCGCA<br>GTCGTTCTGGCAGTGTTCGCCTTATGTTTCTTACCATTTCATGTTACTAGAACACTGTACTA<br>CTCTTTCAGAAGCTTGGACTTATCATGTCATACTTTGAATGCTATCAATATGGCTTATAAGG<br>TTACAAGACCACTTGCGTCCGCAAATTCATGCTTAGACCCTGTGTTATACTTTTTAGCCGGT<br>CAAAGATTAGTGAGATTCGCTAGAGATGCCAAGCCACCAACTGGTCCTTCTCCAGCAACACC<br>AGCACGTAGACGTTTGGGGTTGAGAAGATCTGATAGAACTGATATGCAGAGAATAGAGGATG<br>TTTTAGGTTCTTCCGAAGATTCTCGTAGAACCGAATCTACTCCAGCGGGTAGTGAAAACACC<br>AAAGACATTAGACTATGA (SEQ ID NO: 12) |
| NP_002555.4: P2Y2<br>MAADLGPWNDTINGTWDGDELGYRCRFNEDFKYVLLPVSYGVVCVPGLCLNAVALYIFLCRL<br>KTWNASTTYMFHLAVSDALYAASLPLLVYYYARGDHWPFSTVLCKLVRFLFYTNLYCSILFL<br>TCISVHRCLGVLRPLRSLRWGRARYARRVAGAVWVLVLACQAPVLYFVTISARGGRVICHDT<br>SAPELFSRPVAYSSVMLGLLFAVPFAVILVCYVLMARRLLKPAYGTSGGLPRAKRKSVRTIA<br>VVLAVFALCFLPFHVIRTLYYSFRSLDLSCHTLNAINMAYKVIRPLASANSCLDPVLYFLAG<br>QRLVRFARDAKPPTGPSPATPARRRLGLRRSDRTDMQRIEDVLGSSEDSRRTESTPAGSENT<br>KDIRL (SEQ ID NO: 13) |
| pFUS1<br>AATCTCAGAGGCTGAGTCTCATTTTTCTCAAGGAAACCATGCAGAAGCTGTTGCGAAGTTGA<br>CATCCGCAGCTCAGTCGAACCCCAATGACGAGCAAATGTCAACTATTGAATCATTAATTCAA<br>AAAATCGCAGGATACGTCATGGACAACCGTAGTGGTGGTAGTGACGCCTCGCAAGATCGTGC<br>TGCTGGTGGTGGTTCATCTTTTATGAACACTTTAATGGCAGACTCTAAGGGTTCTTCCCAAA<br>CGCAACTAGGAAAACTAGCTTTGTTAGCCACAGTGATGACACACTCATCAAATAAAGGTTCT<br>TCTAACAGAGGGTTTGACGTAGGGACTGTCATGTCAATGCTAAGTGGTTCTGGCGGCGGGAG<br>CCAAAGTATGGGTGCTTCCGGCCTGGCTGCCTTGGCTTCTCAATTCTTTAAGTCAGGTAACA<br>ATTCCCAAGGTCAGGGACAAGGTCAAGGTCAAGGTCAAGGTCAAGGACAAGGTCAAGGTCAA<br>GGTTCTTTTACTGCTTTGGCGTCTTTGGCTTCATCTTTCATGAATTCCAACAACAATAATCA<br>GCAAGGTCAAAATCAAAGCTCCGGTGGTTCCTCCTTTGGAGCACTGGCTTCTATGGCAAGCT<br>CTTTTATGCATTCCAATAATAATCAGAACTCCAACAATAGTCAACAGGGCTATAACCAATCC<br>TATCAAAACGGTAACCAAAATAGTCAAGGTTACAATAATCAACAGTACCAAGGTGGCAACGG<br>TGGTTACCAACAACAACAGGGACAATCTGGTGGTGCTTTTTCCTCATTGGCCTCCATGGCTC<br>AATCTTACTTAGGTGGTGGACAAACTCAATCCAACCAACAGCAATACAATCAACAAGGCCAA<br>AACAACCAGCAGCAATACCAGCAACAAGGCCAAAACTATCAGCATCAACAACAGGGTCAGCA<br>GCAGCAACAAGGCCACTCCAGTTCATTCTCAGCTTTGGCTTCCATGGCAAGTTCCTACCTGG<br>GCAATAACTCCAATTCAAATTCGAGTTATGGGGGCCAGCAACAGGCTAATGAGTATGGTAGA<br>CCGCAACAGAATGGTCAACAGCAATCCAATGAGTACGGAAGACCGCAATACGGCGGAAACCA<br>GAACTCCAATGGACAGCAGCACGAATCCTTCAATTTTTCTGGCAACTTTTCTCAACAGAACAATA<br>ACGGCAACCAGAACCGCTACTGAACGATGATTCAGTTCGCCTTCTATCCTTTGTTTACGTAT<br>TTGTTTATATATATAACTTTATTTTTTTTATTAATTGGGCTGCAAGACAATTTTGTTGTCA<br>GTGATGCCTCAATCCTTCTTTTGCTTCCATATTTACCATGTGGACCCTTTCAAAACAGAGTT<br>GTATCTCTGCAGGATGCCCTTTTTGACGTATTGAATGGCATAATTGCACTGTCACTTTTCGC<br>GCTGTCTCATTTTGGTGCGATGATGAAACAAACATGAAACGTCTGTAATTTGAAACAAATAA<br>CGTAATTCTCGGGATTGGTTTTATTTAAATGACAATGTAAGAGTGGCTTTGTAAGGTATGTG<br>TTGCTCTTAAAATATTTGGATACGACATCCTTTATCTTTTTTCCTTTAAGAGCAGGATATAA<br>GCCATCAAGTTTCTGAAAATCAAA (SEQ ID NO: 14) |
| NM_001776.6: CD39<br>ATGGAAGATACAAAGGAGTCTAACGTGAAGACATTTTGCTCCAAGAATATCCTAGCCATCCT<br>TGGCTTCTCCTCTATCATAGCTGTGATAGCTTTGCTTGCTGTGGGGTTGACCCAGAACAAAG<br>CATTGCCAGAAAACGTTAAGTATGGGATTGTGCTGGATGCGGGTTCTTCTCACACAAGTTTA<br>TACATCTATAAGTGGCCAGCAGAAAAGGAGAATGACACAGGCGTGGTGCATCAAGTAGAAGA<br>ATGCAGGGTTAAAGGTCCTGGAATCTCAAAATTTGTTCAGAAAGTAAATGAAATAGGCATTT<br>ACCTGACTGATTGCATGGAAAGAGCTAGGGAAGTGATTCCAAGGTCCCAGCACCAAGAGACA<br>CCCGTTTACCTGGGAGCCACGGCAGGCATGCGGTTGCTCAGGATGGAAAGTGAAGAGTTGGC<br>AGACAGGGTTCTGGATGTGGTGGAGAGGAGCCTCAGCAACTACCCCTTTGACTTCCAGGGTG<br>CCAGGATCATTACTGGCCAAGAGGAAGGTGCCTATGGCTGGATTACTATCAACTATCTGCTG<br>GGCAAATTCAGTCAGAAAACAAGGTGGTTCAGCATAGTCCCATATGAAACCAATAATCAGGA<br>AACCTTTGGAGCTTTGGACCTTGGGGGAGCCTCTACACAAGTCACTTTTGTACCCCAAAACC<br>AGACTATCGAGTCCCCAGATAATGCTCTGCAATTTCGCCTCTATGGCAAGGACTACAATGTC<br>TACACACATAGCTTCTTGTGCTATGGGAAGGATCAGGCACTCTGGCAGAAACTGGCCAAGGA<br>CATTCAGGTTGCAAGTAATGAAATTCTCAGGGACCCATGCTTTCATCCTGGATATAAGAAGG<br>TAGTGAACGTAAGTGACCTTTACAAGACCCCCTGCACCAAGAGATTTGAGATGACTCTTCCA<br>TTCCAGCAGTTTGAAATCCAGGGTATTGGAAACTATCAACAATGCCATCAAAGCATCCTGGA<br>GCTCTTCAACACCAGTTACTGCCCTTACTCCCAGTGTGCCTTCAATGGGATTTTCTTGCCAC<br>CACTCCAGGGGGATTTTGGGGCATTTTCAGCTTTTTACTTTGTGATGAAGTTTTTAAACTTG<br>ACATCAGAGAAAGTCTCTCAGGAAAAGGTGACTGAGATGATGAAAAAGTTCTGTGCTCAGCC<br>TTGGGAGGAGATAAAAACATCTTACGCTGGAGTAAAGGAGAAGTACCTGAGTGAATACTGCT<br>TTTCTGGTACCTACATTCTCTCCCTCCTTCTGCAAGGCTATCATTTCACAGCTGATTCCTGG<br>GAGCACATCCATTTCATTGGCAAGATCCAGGGCAGCGACGCCGGCTGGACTTTGGGCTACAT<br>GCTGAACCTGACCAACATGATCCCAGCTGAGCAACCATTGTCCACACCTCTCTCCCACTCCA<br>CCTATGTCTTCCTCATGGTTCTATTCTCCCTGGTCCTTTTCACAGTGGCCATCATAGGCTTG |

-continued

| Exemplary Sequences |
|---|
| CTTATCTTTCACAAGCCTTCATATTTCTGGAAAGATATGGTATAG (SEQ ID NO: 15) |

```
U58597.1: RROP1
ATGTTGAACCAAAATAGTCATTTTATTTTCATAATTTTGGCAATATTTTTGGTTTTGCCCCT
AAGTTTATTATCCAAAAATGTGAATGCCCAAATTCCATTGAGAAGACATTTATTAAGTCATG
AATCAGAACATTATGCAGTAATATTTGATGCTGGAAGTACTGGAAGTAGAGTTCATGTTTTT
CGATTTGATGAAAAATTAGGACTTCTTCCTATTGGCAACAATATTGAGTATTTTATGGCGAC
AGAGCCAGGTTTAAGTTCATATGCAGAAGATCCAAAGGCTGCTGCCAATTCACTTGAGCCAC
TTTTAGATGGAGCTGAAGGAGTTGTTCCTCAAGAATTGCAATCTGAAACACCTTTAGAACTT
GGGGCAACAGCAGGTCTTAGGATGTTAAAAGGGGATGCAGCTGAAAAAATTCTACAAGCAGT
GAGAAATTTAGTGAAGAATCAAAGCACTTTCCATAGCAAAGATCAATGGGTCACTATTCTTG
ATGGAACTCAAGAAGGCTCTTATATGTGGGCTGCAATAAATTATTTATTGGGAAATTTGGGC
AAAGATTATAAAAGTACAACAGCAACAATTGATCTTGGTGGTGGTTCAGTCCAAATGGCATA
TGCTATATCAAATGAACAATTTGCAAAAGCTCCTCAAAATGAGGATGGAGAACCTTATGTTC
AACAAAAACATCTTATGTCAAAAGATTATAATCTCTATGTACATAGTTATTTAAACTATGGG
CAATTAGCAGGTCGAGCTGAGATTTTCAAGGCTTCAAGAAATGAAAGTAATCCTTGTGCTTT
GGAAGGATGTGATGGGTATTACTCATATGGAGGAGTGGACTACAAAGTAAAAGCACCAAAGA
AAGGTAGTAGTTGGAAGAGATGCAGGAGGTTAACTAGACATGCACTTAAAATAAATGCAAAA
TGCAATATTGAAGAATGCACCTTCAATGGAGTGTGGAATGGTGGTGGTGGTGATGGACAAAA
AAATATTCATGCTTCATCATTTTTTTATGATATTGGTGCTCAGGTTGGCATTGTTGACACCA
AATTTCCATCTGCTCTAGCAAAGCCAATTCAATACTTAAATGCAGCTAAAGTTGCTTGCCAA
ACAAATGTGGCAGATATAAAATCCATATTCCCAAAAACTCAAGATAGAAATATCCCATACTT
ATGTATGGACTTGATATATGAGTACACTTTGCTTGTTGATGGATTTGGACTAAATCCACACA
AAGAAATAACAGTGATACATGATGTGCAATACAAAAACTATCTAGTTGGAGCAGCATGGCCA
TTGGGATGTGCCATTGACTTGGTTTCTTCAACTACAAACAAAATTAGAGTTGCATCATCTTA
A (SEQ ID NO: 16)

KD039156.1: TUAP1
ATGGCTCACCTGGTGGGCATGATGGCGCTTCTCCTCCTCCTCCTCGCCTCGTCAGCTGAGAT
AGCCCAGGCGCGCGCGGCAGCGGTGCCGCCGGTGGGGAAGTACGCCGTGATCTTGGACGCCG
GCAGCACGGGGACCCGTATGCACGTCTTCCGGTTTGACAAGCGGATGGATCTCGTCAAGATC
GGCGACGACATCGAGGTCTTCGCCAAGGTGAATCCTGGTCTGAGTTCATACTCTGGACGGCC
CAAGGAGGCTACCGAGTCCATATTACCACTGCTTCAAAAGGCCAACAGCGTCGTGCCTCAGA
GGCTTATGAAAACGACTCCTGTTAAACTCGGGGCGACGGCCGGACTCAGGCTCATCGGAGAT
AAGCAAGCAAAGCAGATACTTGACGCGGTCAGGGGCGCTGTCCACACTAACACCAAGTTTCA
GTACAATCCCAAGTGGATCAATGTTCTCGAGGGATCTCAGGAAGGATCCTACCTATGGGTTG
CTCTGAATTACCTGCTGGATAACTTGGGTGGGGACTACTCGAAAACGGTAGGTGTGATTGAT
CTTGGAGGTGGGTCCGTGCAAATGGCATATGCCATTTCTCCGGCCACCGTTGTTGCCGCTCC
AGGAGTGCCTCACGGCAAGGATCCTTATGTTACAAAAGAGTATCTCAAGGGAAGAGATTACA
ACATTTATGTTCACAGCTACTTACGCTACGGCGCCTTAGCTTCTCGCGTAGAGATCTTCAAG
GCTAAGGAAGGACCATTTAGCTACTGCATGCTTCGTGGCTTCAGTGGCAAATACACCTACAA
CGGTGAGGAGTACAATGCTACCGCGTCAACGGGAGGTGCACAATACGGGAAGTGCAGAGGTG
ATGTAATGAAGGCACTCAAACTTGATGCTCCTTGCCAAGCCAAGAAGTGCACCTTCGACGGC
GTGTGGAACGGCGGGGGCGGCCCCGGCCAGGCCAACCTCTATGTCGCATCTAGCTTCTACTA
CATGGCCTCGCAGGTTGGCCTCATCGACAGTGATGCACCAAGCGGGACGTCCACCCCAATGG
CTTTCAGAGCCGTTGCCCAGAAGATATGTAGAATGAGCTTGAAAGAAGTGAAGGCTAAGTAC
CCCAAGGTCCGCGACATACCCTACATTTGCATGGACCTCGTCTATCAATACTCCTTGCTCGT
CGATGGGTTTGGTTTGGAACCCACCAAGAATATTACACTCGTGGAGAAGGTGAAGCATGGGG
AGTACTTCATTGAAGCGGCATGGCCTCTCGGAGAAGCTATTGAGGCCGTGGCACCCAAAAAG
GGGACTTGA (SEQ ID NO: 17)
```

Example 1. Directed Evolution of the Human P2Y2 Receptor

Figure 1C:
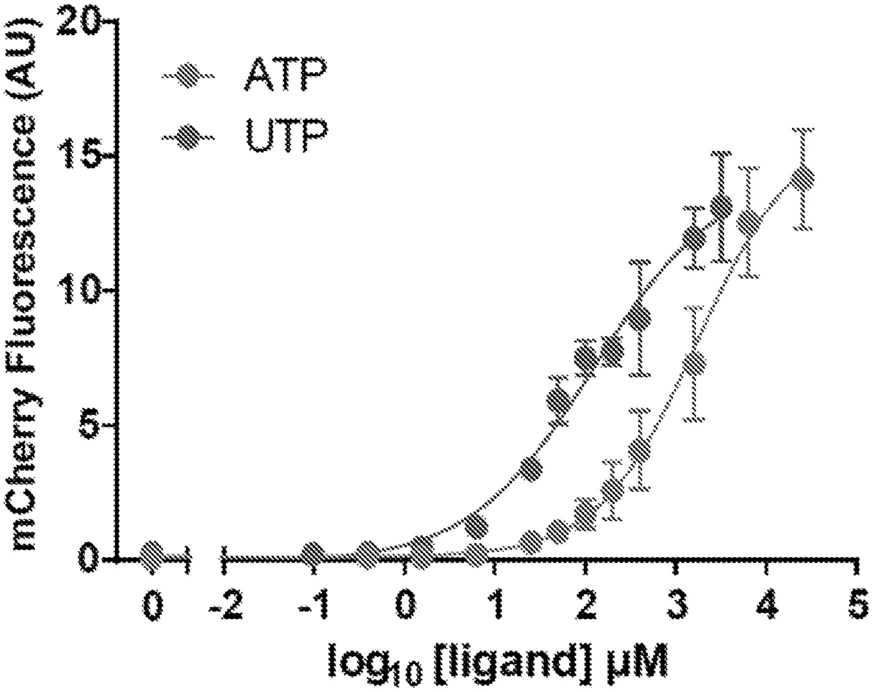

The P2Y2 receptor is a G protein-coupled receptor (GPCR) that senses eATP and also extracellular uridine triphosphate (eUTP) (29). We first engineered the human P2Y2 receptor to increase its sensitivity to eATP when expressed in yeast. To establish a platform amenable to directed evolution, we coupled the human P2Y2 receptor to the yeast mating pathway via a chimeric yeast Gpa1-human $G\alpha_{i3}$ protein and monitored pathway activation using a fluorescent mCherry reporter controlled by the mating-responsive FUS1 promoter (pFUS1) (FIG. 1A,B, Table 1, and FIG. 7A-B). The Gpa1-Gai pFUS1-mCherry strain transformed with a plasmid constitutively expressing human P2Y2, showed a dose-dependent response to its agonists eATP and eUTP, with a log EC50 of 3.27 and 2.09 μM, respectively (FIG. 1C).

Figure 1D:
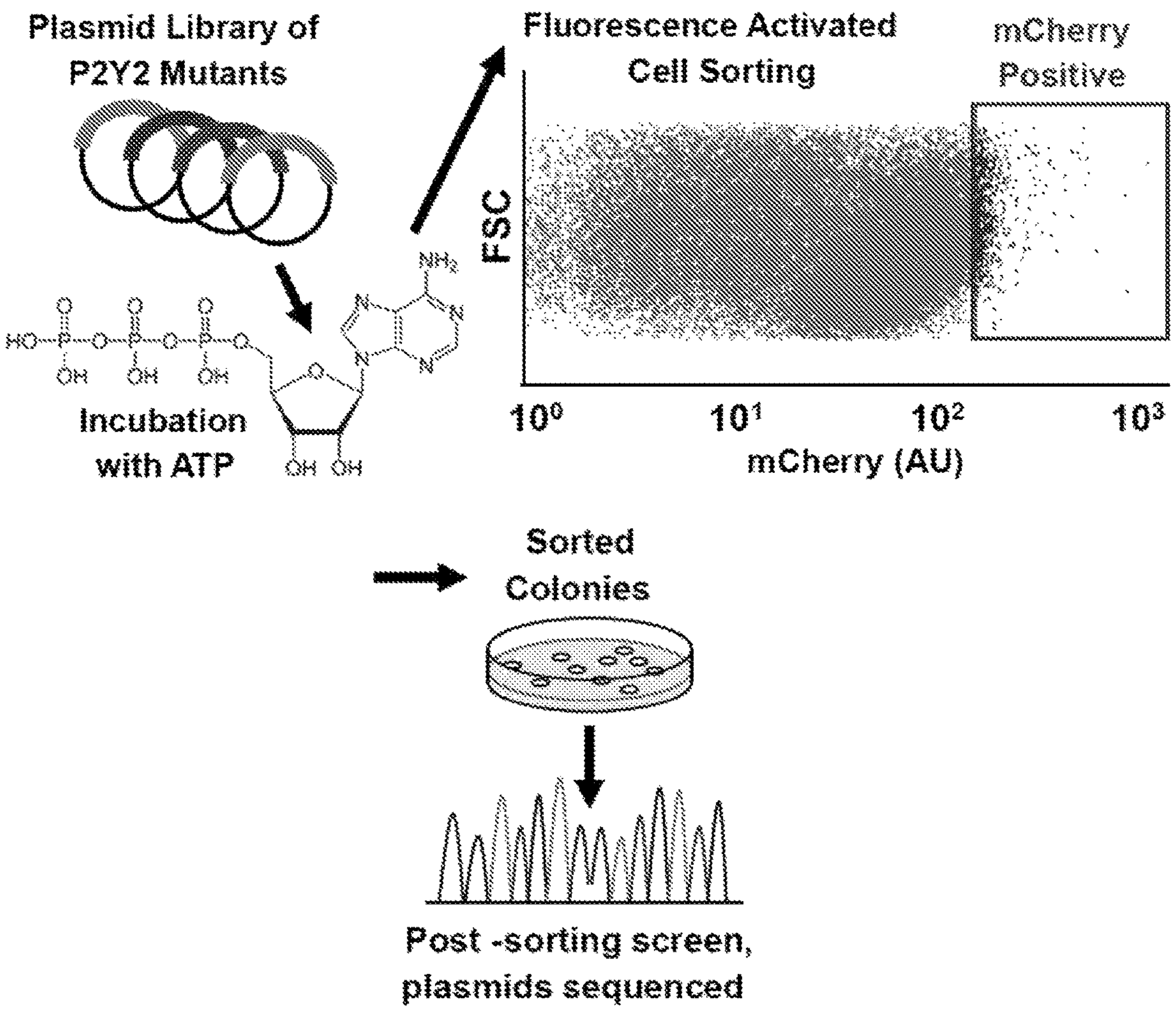

Physiological eATP levels associated to inflammation have been detected in the 100 μM to high mM range (35). However, yeast expressing wild-type (WT) P2Y2 show a weak response to 100 μM eATP as determined by the analysis of mCherry expression by flow cytometry (FIG. 1C). Thus, we applied directed evolution to generate yeast-expressed human P2Y2 receptor mutants that show increased sensitivity to eATP. To achieve this goal, we first generated a plasmid library of human P2Y2 receptor mutants using error-prone PCR (Table 2) and isolated by fluorescence-activated cell sorting (FACS) yeasts expressing the highest (top 1%) pFUS1-driven mCherry fluorescence after treatment with 100 μM eATP (FIG. 1D).

Figure 2A:
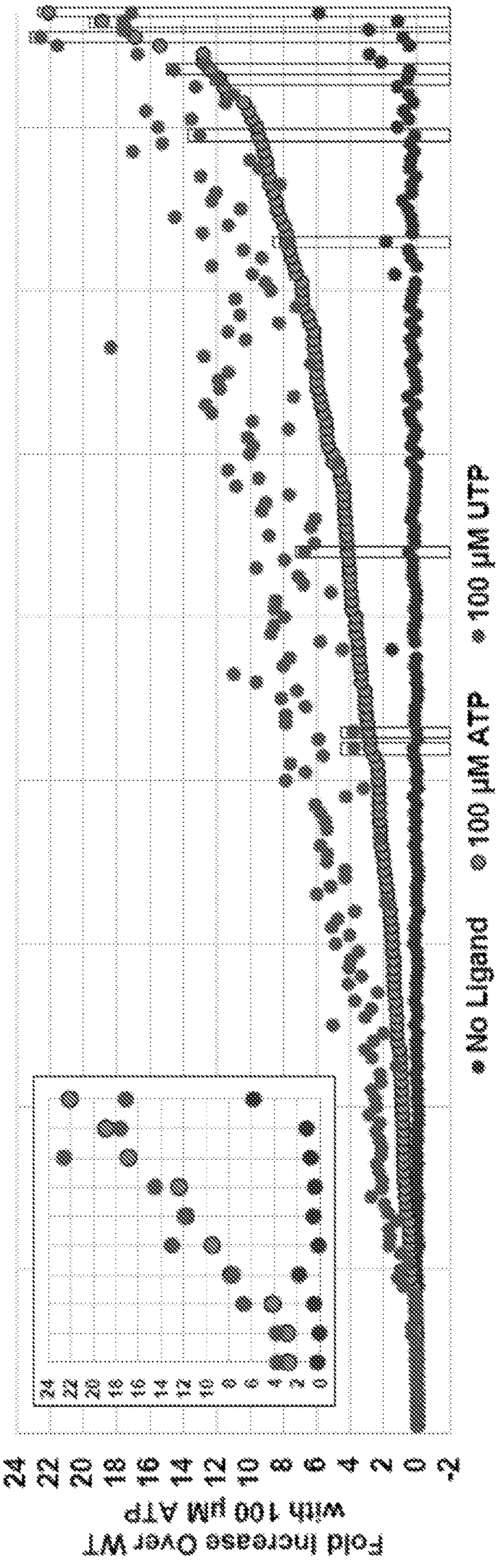
FIGS. 2A-B: Increased responsiveness to eATP of human P2Y2 receptor mutants generated by directed evolution. (A) Randomly selected yeast colonies were incubated with the indicated ligand for 6 hours and mCherry fluorescence was quantified. Responses normalized to WT human P2Y2 receptor activated with 100 μM ATP, so that the y-axis represents the fold-increase above the WT response. Ten yeast colonies were selected for detailed characterization (purple boxes), their responses to 100 μM ATP and 100 μM UTP are shown in the FIG. inset. (B) Multiple mutations in the human P2Y2 receptor increased the sensitivity and maximum response to eATP and eUTP. mCherry fluorescence is represented as a percentage of the maximum WT response to eATP. Mutants are grouped based on the location of mutant residues. Data points represent the mean of six colonies for eATP, three colonies for eUTP, each transformed with a plasmid encoding the indicated human P2Y2 receptor mutant. Error bars represent the SEM.

We performed multiple iterative rounds of FACS-based selection (36) to isolate mutants displaying the desired increase in eATP sensitivity (FIG. 8). Finally, in a post-sorting screening step, we further assessed the function of the engineered human P2Y2 receptor mutants by treating the selected yeast colonies with 100 μM eUTP, 100 μM eATP or vehicle (FIG. 2A). Of the 174 yeast colonies selected after multiple rounds of FACS-selection, 128 colonies exhibited a response to eATP stronger than the one detected using the WT human P2Y2 receptor; 163 colonies showed a stronger response to eUTP. For most (but not all) of the analyzed colonies, an increased response to eATP was concomitant with an increased response to eUTP.

We focused on human P2Y2 receptor mutants that showed an enhanced response to eATP, and a high eATP/eUTP response ratio concomitant with no constitutive expression of mCherry. The sequencing of these human P2Y2 receptor mutants revealed a diverse range of genotypes, with up to three non-synonymous mutations (Table 3). Eight of the 19 human P2Y2 mutants harbored a mutation at site $F58^{1.57}$, as defined by the Ballesteros-Weinstein convention in which the first number is the transmembrane helix, followed by a conserved position across all family A GPCRs (37). We also detected mutations at nearby residues $L59^{1.58}$ and $C60^{1.59}$, and at $Q165^{4.57}$ and $F307^{7.54}$.

Figure 2B:
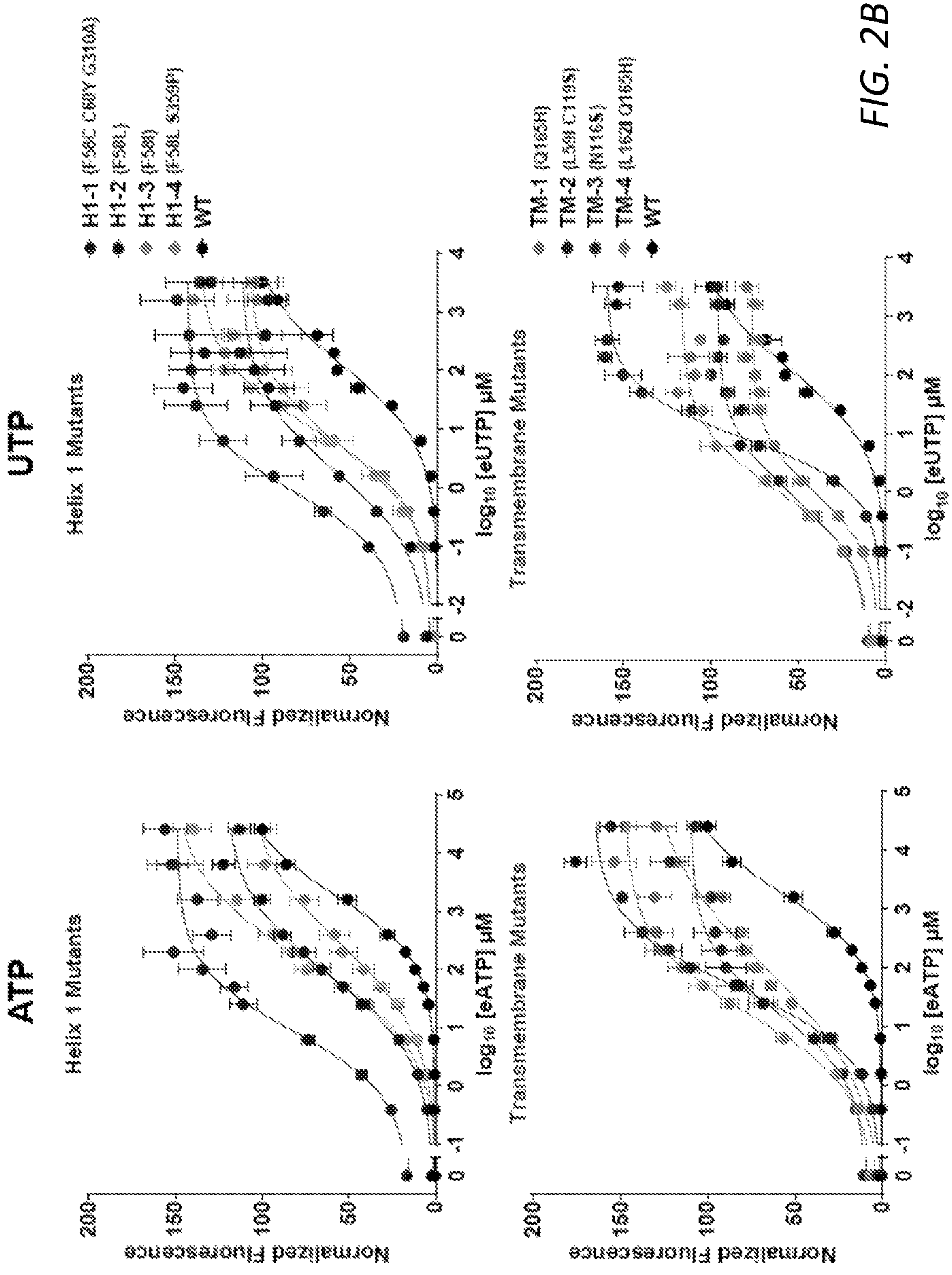

We selected 10 P2Y2 mutants for detailed characterization, each mutant was named using a unique identifier based on the location of the mutated residue(s) (Table 4). In dose-response studies, the engineered P2Y2 receptors were more responsive to both eATP and eUTP (FIG. 2B). When compared to the WT human P2Y2 receptor, the selected mutants showed a 10-1000 fold decrease in the eATP EC50, and up to a 1.8-fold increase in the maximum mating pathway response. This increased sensitivity was also detected in response to eUTP stimulation, except for strains harboring the Q165H4.57 mutation (TM-1, TM-4), in which the maximum mating pathway response was 1.4- to 2-fold higher for eATP than for eUTP. Thus, the application of directed evolution resulted in the generation of human P2Y2 receptor mutants with increased responsiveness to eATP.

TABLE 1

Yeast Strain Genotypes

| Name | Genotype | Reference |
|---|---|---|
| CB008 | W303 MATa his3Δ trp1Δ leu2Δ ura3Δ far1Δ | (98) |
| BS004 | CB008 mfa2::KanMX-pFUS1 mCherry | (99) |
| BS010 | BS004 sst2::HygB | (99) |
| BS011 | BS010 ste2::TRP1 | (99) |
| BS016 | BS011 gpa1::Gpa1-Gαi3-LEU2 | This study |
| BS019 | BS011 gpa1::Gpa1-Gα14-LEU2 | This study |
| BS020 | BS011 gpa1::Gpa1-Gαq-LEU2 | This study |
| BS021 | BS016 mfa2::HIS3-pFUS1 mCherry | This study |
| P4 Strain | BS021 sst2::pTDH3 P2Y2 | This study |
| H1-1 Strain | BS021 sst2::pTDH3 P2Y2 H1-1 (F58C C60Y G310A) | This study |

TABLE 1-continued

Yeast Strain Genotypes

| Name | Genotype | Reference |
|---|---|---|
| H1-3 Strain | BS021 sst2::pTDH3 P2Y2 H1-3 (F58I) | This study |
| TM-1 Strain | BS021 sst2::pTDH3 P2Y2 TM-1 (Q165H) | This study |
| TM-2 Strain | BS021 sst2::pTDH3 P2Y2 TM-2 (L59I C119S) | This study |
| TM-3 Strain | BS021 sst2::pTDH3 P2Y2 TM-3 (N116S) | This study |
| H7-1 Strain | BS021 sst2::pTDH3 P2Y2 H7-1 (K240N F307S) | This study |
| H7-2 Strain | BS021 sst2::pTDH3 P2Y2 H7-2 (A76T A229V F307S) | This study |
| BS029 | CB008 mfa2::HIS3-pTDH3 RROP1 | This study |
| BS030 | CB008 mfa2::HIS3-pTDH3 TUAP1 | This study |
| AP-P4 | P4 Strain mfa2::HIS3-pFUS1 RROP1 | This study |
| APH1-1 | H1-1 Strain mfa2::HIS3-pFUS1 RROP1 | This study |
| APH1-3 | H1-3 Strain mfa2::HIS3-pFUS1 RROP1 | This study |
| APTM-1 | TM-1 Strain mfa2::HIS3-pFUS1 RROP1 | This study |
| APTM-2 | TM-2 Strain mfa2::HIS3-pFUS1 RROP1 | This study |
| APTM-3 | TM-3 Strain mfa2::HIS3-pFUS1 RROP1 | This study |
| APH7-1 | H7-1 Strain mfa2::HIS3-pFUS1 RROP1 | This study |
| CB008 KG | CB008 HO::pTDH3 sfGFP-KanMX | This study |
| APTM-3 KG | APTM-3 HO::pTDH3 sfGFP-KanMX | This study |
| BS029 KG | BS029 HO::pTDH3 sfGFP-KanMX | This study |
| P4 KG | P4 Strain HO::pTDH3 sfGFP-KanMX | This study |
| TM-3 KG | TM-3 Strain HO::pTDH3 sfGFP-KanMX | This study |
| BS035 | CB008 mfa2::HIS3-pTDH3 mCherry | This study |
| BS035 KG | BS035 HO::pTDH3 sfGFP-KanMX | This study |

TABLE 2

DNA mutation rates of the P2Y2 gene

| Library Number | 1 | 2 | 3 | 4 | 5 | 6 |
|---|---|---|---|---|---|---|
| Template DNA (ng) | 100 | 150 | 250 | 500 | 150 | 250 |
| Number of cycles | 20 | 20 | 20 | 20 | 30 | 30 |
| Sequences analysed | 18 | 18 | 12 | 12 | 12 | 12 |
| Mean substitution rate | 1.83 | 1.65 | 2.08 | 1.25 | 3.25 | 2.25 |
| Mean insertion rate | 0 | 0 | 0 | 0 | 0 | 0 |
| Mean deletion rate | 0.22 | 0 | 0.08 | 0 | 0.08 | 0.17 |
| Mean mutation rate | 2.05 | 1.65 | 2.17 | 1.25 | 3.33 | 2.42 |

Selected "Library 5" for yeast transformation and FACS based on the desired mutation rate of 5 ~3 mutations per P2Y2 sequence (~2.9 mutations/kb)

TABLE 3

Extended List of P2Y2 Mutants Following Directed Evolution

| Mutant | Numbered Name | Amino Acid Mutation | Residue Location | Follow-up Test Results | F58 mutation |
|---|---|---|---|---|---|
| H1-1 | 18R1-7 | F58C | TM1 | Selected for detailed characterization | * |
| | | C60Y | TM1 | | |
| | | L150L | IL2 | | |
| | | L215L | TM5 | | |
| | | G310A | C-term | | |
| H1-2 | 18R2-10 | F58L | TM1 | Selected for detailed characterization | * |
| | | H74H | TM2 | | |
| | | L206L | TM5 | | |
| H1-3 | 18R2-11 | F58I | TM1 | Selected for detailed characterization | * |
| H1-4 | 62R1-11 | F58L | TM1 | Selected for detailed characterization | * |
| | | S359P | C-term | | |
| TM-1 | 18R2-89 | L88L | TM2 | Selected for detailed characterization | |
| | | Y149Y | TM4 | | |
| | | Q165H | TM4 | | |
| TM-2 | 18R2-106 | V53V | TM1 | Selected for detailed characterization | |
| | | L59I | TM1 | | |
| | | C119S | TM3 | | |

TABLE 3-continued

Extended List of P2Y2 Mutants Following Directed Evolution

| Mutant | Numbered Name | Amino Acid Mutation | Residue Location | Follow-up Test Results | F58 mutation |
|---|---|---|---|---|---|
| TM-3 | 62R1-8 | N116S | TM3 | Selected for detailed characterization | |
| TM-4 | 18R2-103 | L162I | TM4 | Selected for detailed characterization | |
| | | Q165H | TM4 | | |
| H7-1 | 18R1-2 | K240N | TM6 | Selected for detailed characterization | |
| | | F307S | TM7 | | |
| H7-2 | 18R2-66 | A76T | TM2 | Selected for detailed characterization | |
| | | A229V | IL3 | | |
| | | F307S | TM7 | | |
| | 18R2-1 | F58L | TM1 | Same as 18R2-10, not tested | * |
| | | L160L | TM4 | | |
| | 18R2-2 | L112S | TM3 | No different than WT, not selected for detailed characterization | |
| | | A176V | EL2 | | |
| | 18R2-8 | F58L | TM1 | Same as 18R2-10, not tested | * |
| | | L160L | TM4 | | |
| | 18R2-9 | F58I | TM1 | Same as 18R2-11, not tested | * |
| | 18R2-18 | W16R | N-term | Approx. 100-fold lower ATP EC50, but inconsistent results | |
| | | V90A | TM2 | | |
| | | L267L | TM6 | | |
| | | A295V | TM7 | | |
| | 18R2-23 | S78S | TM2 | No different than WT, not selected for detailed characterization | |
| | | V250A | TM6 | | |
| | | D275D | EL3 | | |
| | 18R2-31 | F58I | TM1 | Same as 18R2-11, not tested | * |
| | 18R2-40 | Q165H | TM4 | Same as 18R2-89, not tested | |
| | | L191L | EL2 | | |
| | 6R1-2 | L30L | N-term | No different than WT, not selected for detailed characterization | |
| | | C164C | TM4 | | |
| | | I214T | TM5 | | |
| | | D275D | EL3 | | |

Only unique mutants that consistently improved upon WT response/sensitivity to ATP were selected for detailed characterization.

TABLE 4

Response to eATP and eUTP of engineered human P2Y2 receptor mutants.

| | | ATP | | | | UTP | | | |
|---|---|---|---|---|---|---|---|---|---|
| Mutant Name | Amino Acid Mutations | logEC50 (±SE) μM | Max Response (±SE) | Dynamic Range | Linear Range μM | logEC50 (±SE) μM | Max Response (±SE) | Dynamic Range | Linear Range μM |
| WT | — | 3.27 (±0.09) | 100 (±6.8) | 8 | 113-25,600 | 2.09 (±0.15) | 98 (±8.6) | 9 | 4-1,374 |
| H1-1 | F58C C60Y G310A | 0.94 (±0.15) | 149 (±5.6) | 5 | 0.5-184 | −0.09 (±0.22) | 128 (±5.7) | 4 | 0.05-12 |
| H1-2 | F58L | 1.91 (±0.09) | 122 (±4.6) | 9 | 4-4,966 | 0.28 (±0.34) | 101 (±8.6) | 6 | 0.05-22 |
| H1-3 | F58I | 2.15 (±0.13) | 152 (±9.3) | 10 | 4-3,945 | 0.99 (±0.07) | 122 (±3.1) | 8 | 0.4-550 |
| H1-4 | F58L S359P | 2.43 (±0.20) | 110 (±11) | 9 | 5-3,882 | 2.43 (±0.20) | 96 (±7.1) | 7 | 0.2-61 |
| TM-1 | Q165H | 1.20 (±0.13) | 147 (±5.8) | 7 | 0.6-585 | 0.04 (±0.13) | 105 (±2.9) | 6 | 0.06-40 |
| TM-2 | L59I C119S | 1.67 (±0.06) | 165 (±4.2) | 9 | 3-2,243 | 0.92 (±0.07) | 143 (±3.5) | 8 | 0.9-169 |
| TM-3 | N116S | 1.22 (±0.17) | 110 (±5.5) | 5 | 0.9-284 | −0.06 (±0.08) | 86 (±1.5) | 5 | 0.04-63 |
| TM-4 | L162I Q165H | 2.00 (±0.17) | 137 (±9.3) | 10 | 0.5-8,950 | −0.02 (±0.10) | 69 (±1.6) | 7 | 0.07-31 |
| H7-1 | K240N F307S | 0.26 (±0.14) | 181 (±4.5) | 3 | 0.3-18 | −0.78 (±0.15) | 199 (±4.7) | 3 | 0.02-3.1 |
| H7-2 | A76T A229V F307S | 0.42 (±0.17) | 90 (±2.8) | 2 | 0.3-23 | −0.57 (±0.28) | 84 (±3.6) | 3 | 0.01-6 |

Maximum response values were normalized to the maximum mating pathway activation provided by the WT human P2Y2 receptor incubated with eATP. Dynamic range was the ratio of the highest fluorescence obtained in the presence of the indicated ligand versus 10% signal saturation. Linear range was the series of ligand concentrations for which a change in signal can be detected. The minimum limit of the linear range was estimated as the ligand concentration corresponding to 10% signal saturation. Data represents the mean of six colonies for eATP, three colonies for eUTP.

Figure 3A:
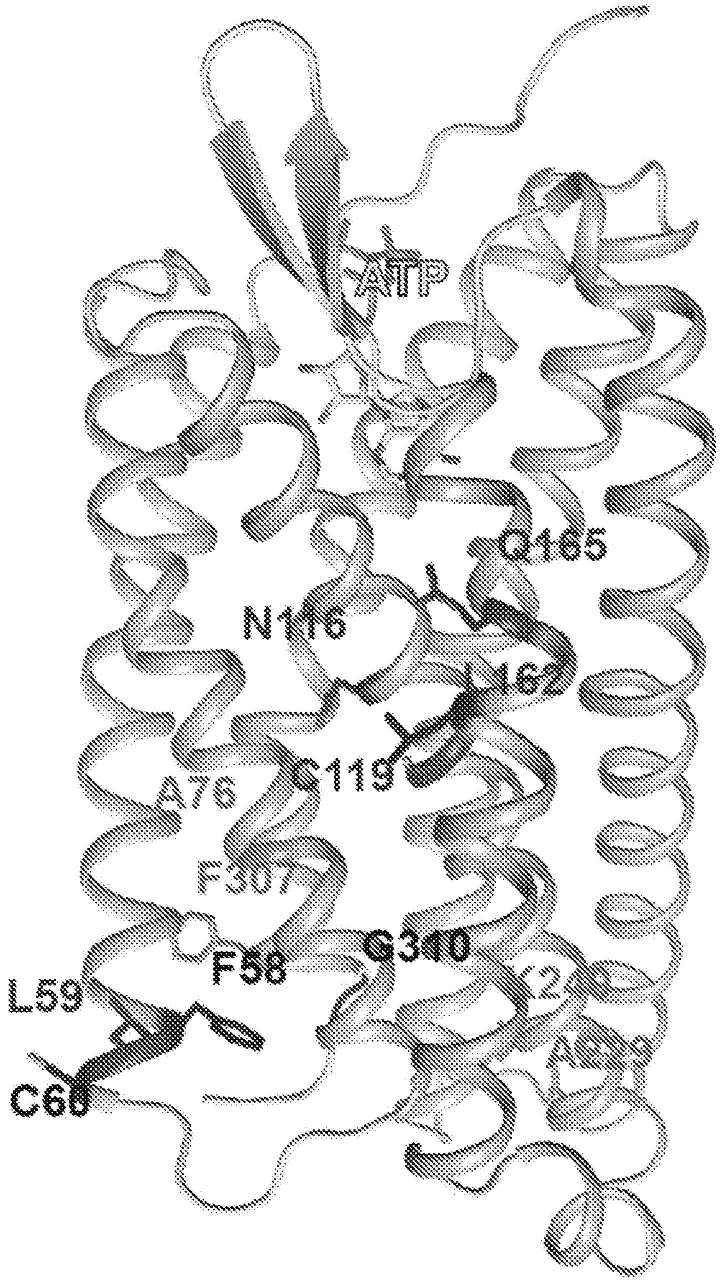
FIGS. 3A-H: Characterization of human P2Y2 receptor mutants. (A) Residues mutated in human P2Y2 receptor following directed evolution. The top ten mutant human P2Y2 receptors with enhanced ATP sensitivity were grouped based on the location of mutant residues: Helix 1, Helix 7, and the Transmembrane Region. ATP docked in the putative binding pocket is indicated in light grey. Residues F58, Q165, and F307 were mutated in eight of the top ten mutants. Generated using MODELLER 9.18 based on the structure of the P2Y1 receptor (4XNW.pdb). (B) The expression of C-terminal GFP tagged human P2Y2 receptor mutants in yeast was quantified by flow cytometry. Mean GFP values were normalized to WT P2Y2 expression. Data is the mean of at least three colonies, error bars represent the standard deviation. *P<0.05 vs WT (C) Representative images of GFP tagged endogenous yeast STE2 GPCR and human P2Y2 receptor mutants examined by confocal microscopy. Scale bars represent 5 μM. (D-G) The combination of human P2Y2 receptor mutations generated by directed evolution reveals novel GPCR features. (D) The combination of the N116S mutation with either F58I or F307S resulted in a maximally active human P2Y2 receptor. The F307S mutation conferred constitutive activity, improved sensitivity and improved response to eATP. (E) Non-additive effects contribute to the increased activity of human P2Y2 receptor TM-2 mutants. The L59I and C119S mutations alone conferred a moderate increase in sensitivity to ATP. The combined effect is less than the one detected in the TM-2 mutant, indicating a non-additive change. (F) By analyzing each mutation in the H1-1 mutant separately, F58C was identified as the primary mutation influencing activity. K240N did not contribute to the increased activity detected. (G) The TM-1 mutant harbors silent mutations, in addition to the Q165H mutation. The silent mutations contribute to increased ATP sensitivity, including when they are combined with the F58I mutation. mCherry fluorescence is represented as a percentage of the maximum wild-type response to ATP. Data points represent the mean of at least three colonies, each transformed with a plasmid encoding the indicated P2Y2 mutant. Error bars represent the SEM. (H) P2Y2 residue F58 was mutated to all other amino acids, and the dose-response to eATP was evaluated using the Gpa1-Gai3 mCherry reporter strain. mCherry fluorescence is represented as a percentage of the maximum wild-type response to ATP. Data points represent the mean of at least three colonies, each transformed with a plasmid encoding the indicated P2Y2 mutant. Error bars represent the SEM.

Example 2. Characterization of Human P2Y2 Receptor Mutants with Increased Sensitivity to eATP Key residues that participate in the binding of nucleotides and the activation of human P2Y2 receptor have been identified (38, 39), but the mutations detected in the ten human P2Y2 receptor mutants that we analyzed did not involve previously identified key residues. Instead, the novel human P2Y2 receptor mutants we identified involved residues peripheral to the ligand binding pocket (A76$^{2.47}$, N116$^{3.35}$, C119$^{3.38}$, L162$^{4.54}$, Q165$^{4.57}$), or residues located in the intracellular facing side of the receptor (F58$^{1.57}$, L59$^{1.58}$, C60$^{1.59}$, A229$^{ICL3}$, K240$^{6.31}$, F307$^{7.54}$, G310$^{C\text{-}term}$) (FIG. 3A).

Figure 3B:
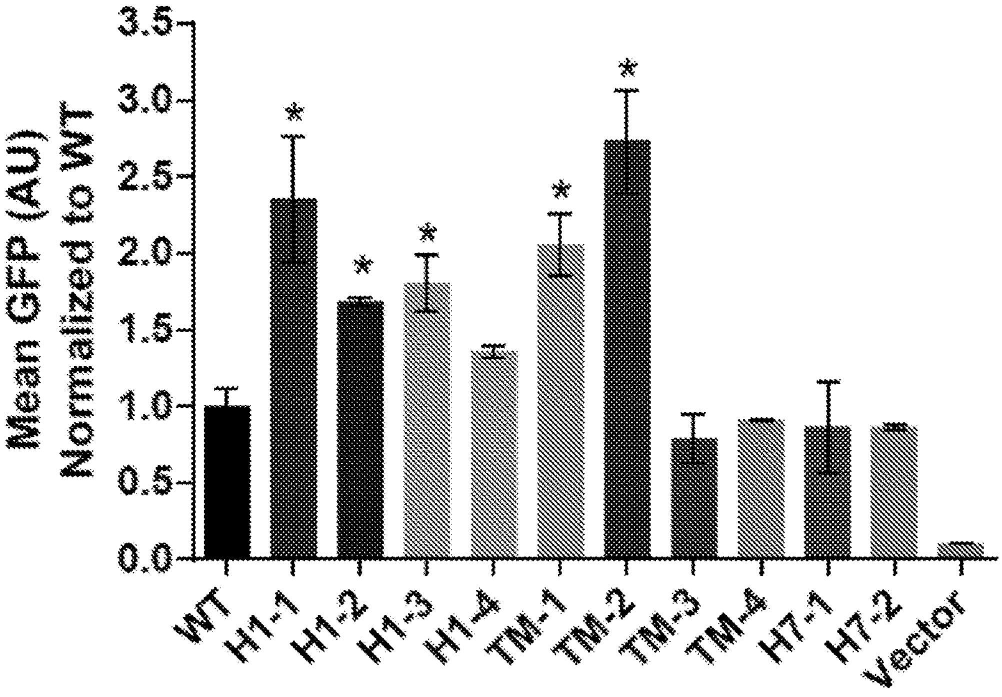
Figure 3C:
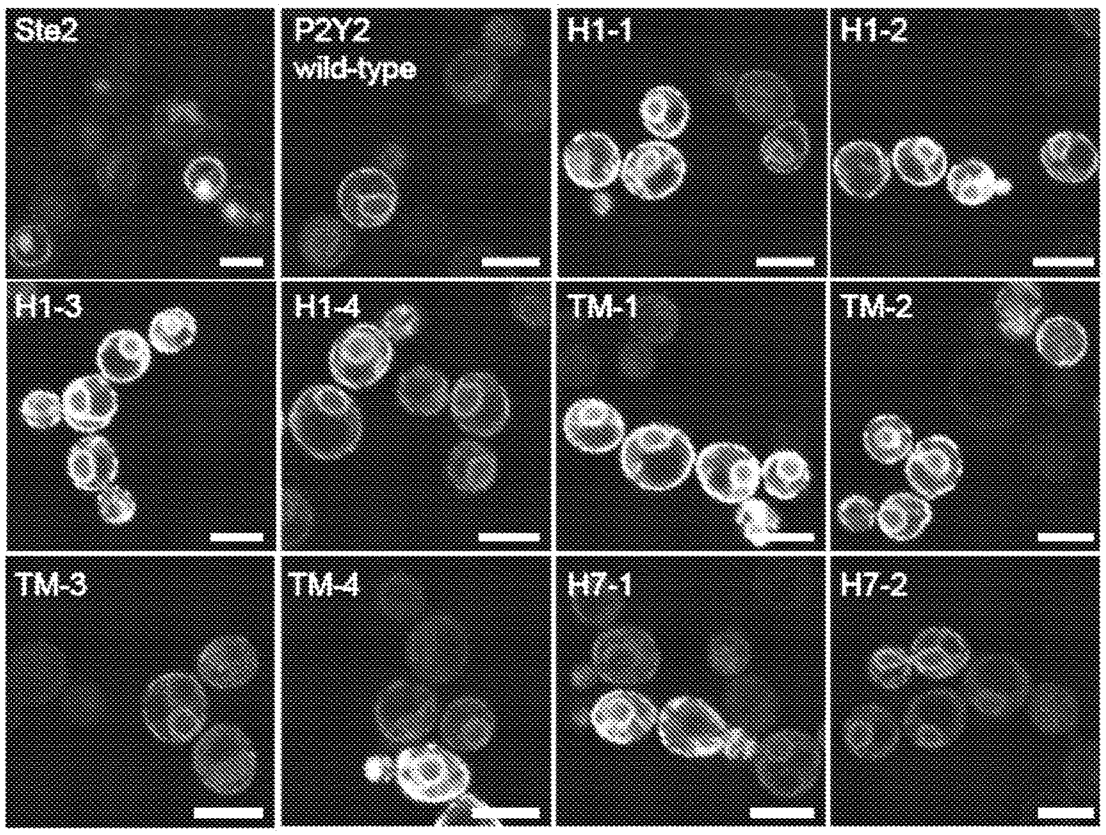

To determine the molecular mechanisms responsible for the increased sensitivity of the selected human P2Y2 receptor mutants generated by directed evolution, we first analyzed their expression levels by microscopy and flow cytometry using receptor mutants tagged with C-terminal GFP. Human P2Y2 receptor expression in yeast was increased when F58$^{1.57}$ was mutated to a smaller hydrophobic residue (C/I/L, "H1" mutants), and also in TM-1 and TM-2 mutants (FIGS. 3B,C and Table 3). Mutations in human GPCR sequences have been previously shown to improve expression in yeast (40), but these previously described mutations did not involve residues homologous to the ones we identified in human P2Y2 receptor mutants generated by directed evolution. Improved GPCR expression often results from increased stability, such as the S90A3.38 mutation in the human adenosine A2A receptor (41) which is similar to the P2Y2 C119S3.38 mutation reported in our work. Mutations in transmembrane helix 1 of other GPCRs also increase stability (42), but these mutations have been found at intramembrane residues, and not at intracellular facing residues such as F58$^{1.57}$, L59$^{1.58}$, C60$^{1.59}$. Thus, our findings identify a novel role for transmembrane helix 1 intracellular-facing residues in the regulation of human P2Y2 expression and potentially, stability.

Figure 3D:
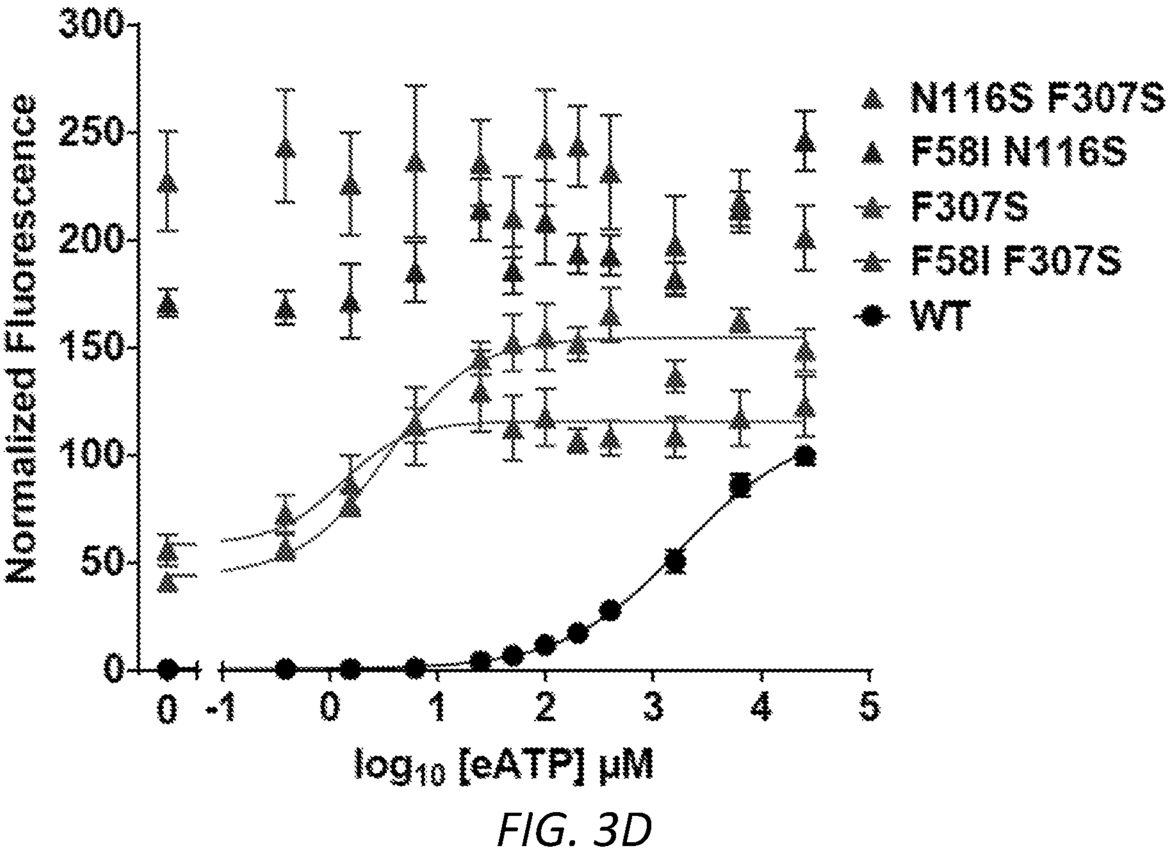

We detected increased responsiveness and signaling in the absence of agonist (constitutive activity) in P2Y2 mutants harboring the N116S$^{3.35}$ and F307S$^{7.54}$ mutations (TM-3, H7-1, H7-2 mutants) (FIGS. 2B and 3D). Interestingly, these mutants showed expression levels similar to those of WT P2Y2 receptor. Mutations at the N3.35 residue in other family A GPCRs are reported to disrupt a hydrogen bonding network with TM2 and TM7 residues and confer constitutive activity (43). In the engineered human P2Y2 receptor described herein, the N116S mutation likely disrupts a similar network with D79$^{2.50}$ and N298$^{7.45}$, and the lack of these stabilizing interhelical interactions leads to increased signaling in the absence of agonist.

The F7.54 residue is located immediately after the highly conserved D/NPxxY (SEQ ID NO: 18) motif required for G protein activation (44). Indeed, mutations at F7.54 in the P2Y12 receptor result in constitutive activity (45). The human P2Y2 receptor lacks the conserved F8.50 residue in helix 8, which in other GPCRs interacts with Y7.53 to stabilize the inactive conformation (46). In the human P2Y2 receptor, F307$^{7.54}$ may instead form this interaction with Y7.53, in addition to conserved contacts with helix 8 in the inactive state (47). Taken together, our findings suggest that the F307S7.54 mutation facilitates the rotation of Y7.53 into the active conformation, resulting in constitutive activity and increased eATP sensitivity.

Figure 3E:
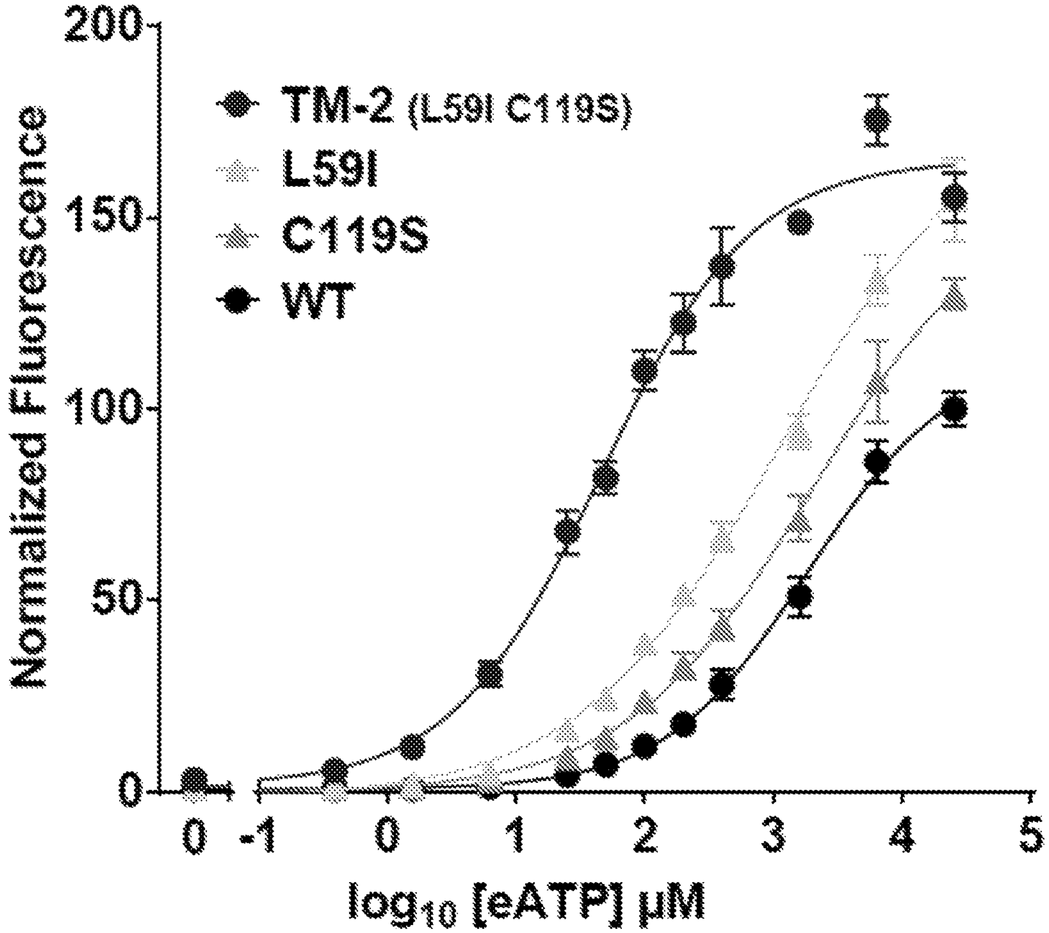
Figure 3F:
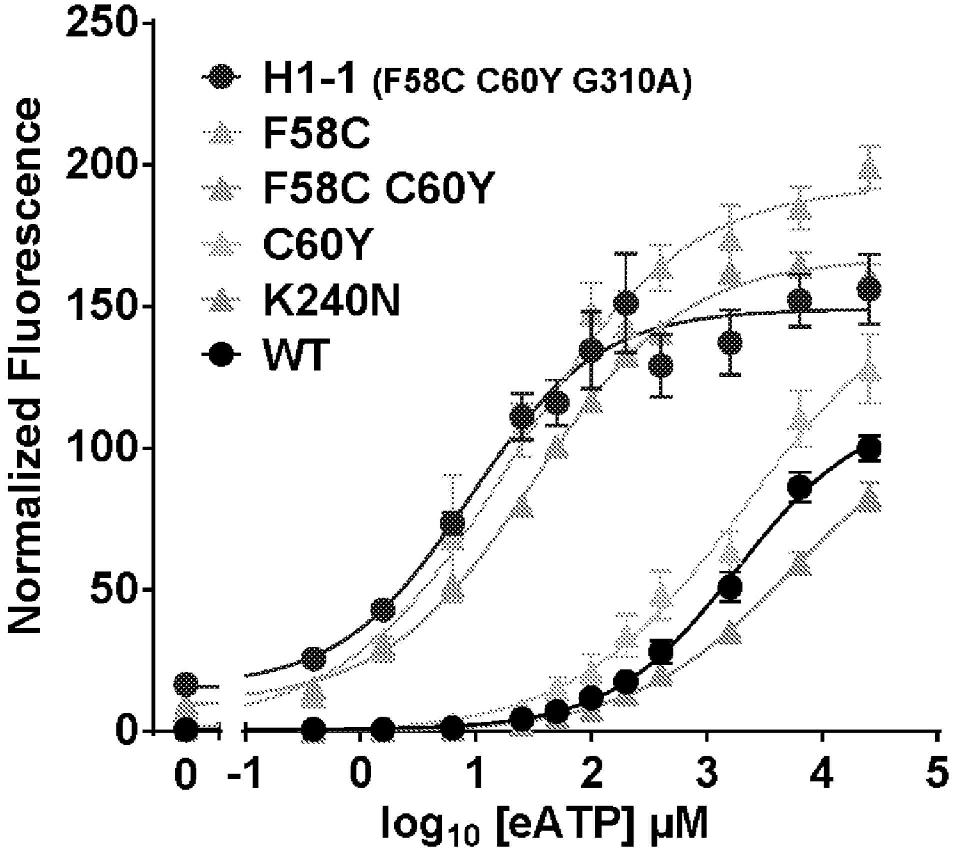
Figure 3G:
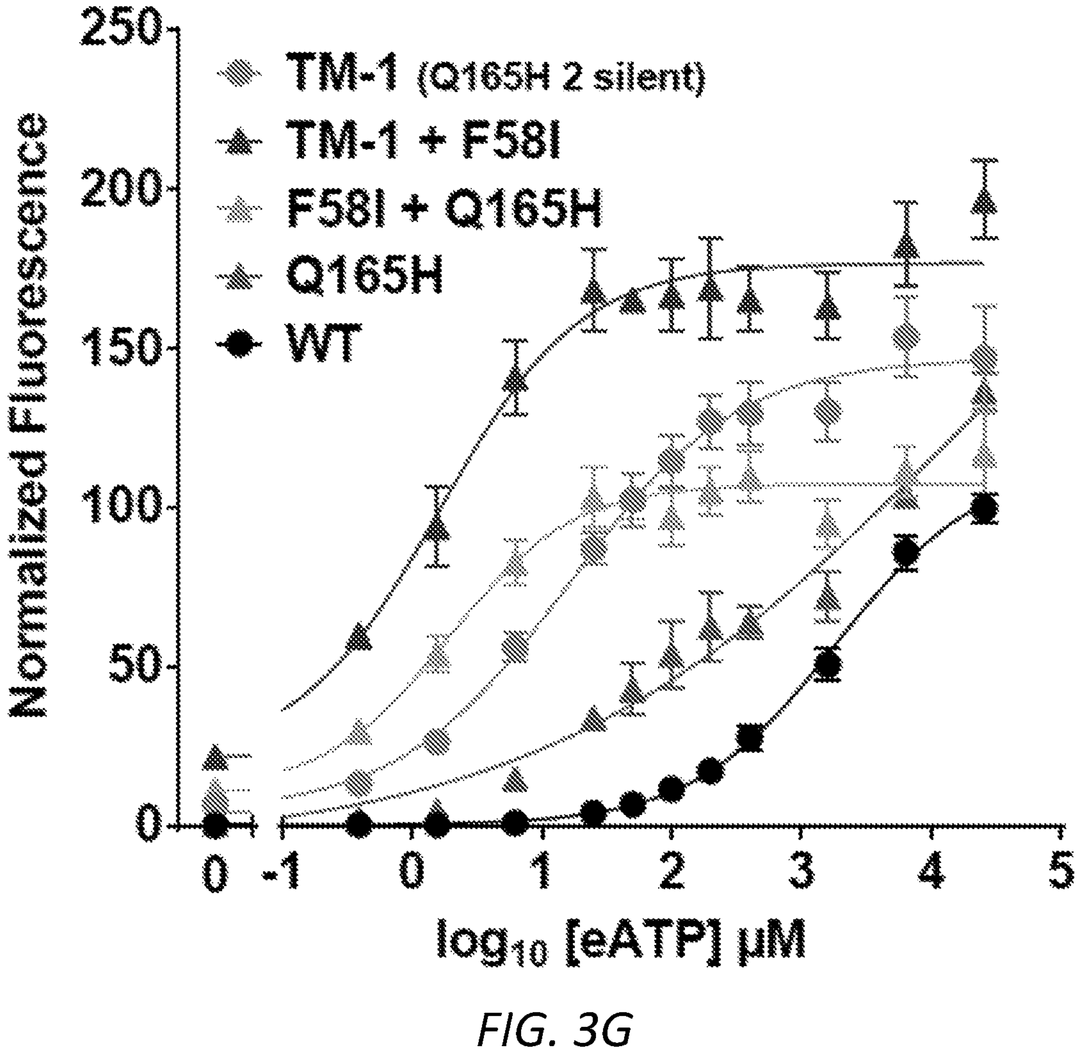

To further investigate the mechanisms responsible for the differential activity of human P2Y2 receptor mutants, we evaluated the effects of each mutation alone or in combination with other mutations in P2Y2 receptor activation by eATP. Certain mutations (C60Y, K240N, G310A) did not cooperate to further increase P2Y2 receptor responsiveness to eATP, while others showed deleterious effects (A76T/A229V, L1621, S359P) or exhibited positive epistasis when combined (N116S with F58I or F307S, L59I/C119S) (FIG. 3D-F). Synonymous mutations in the TM-1 mutant sequence increased P2Y2 receptor sensitivity towards eATP, which could be further increased by incorporating the F58I mutation (FIG. 3G). In the human P2Y2 receptor homology model docked with ATP, Q165$^{4.57}$ is oriented towards the adenine ring of ATP. These findings suggest that the Q165H mutation favors receptor interactions with ATP that result in increased downstream signaling. These effects of the Q165H mutation are further amplified by the increased expression of the human P2Y2 receptor driven by F58I or synonymous mutations.

Figure 3H:
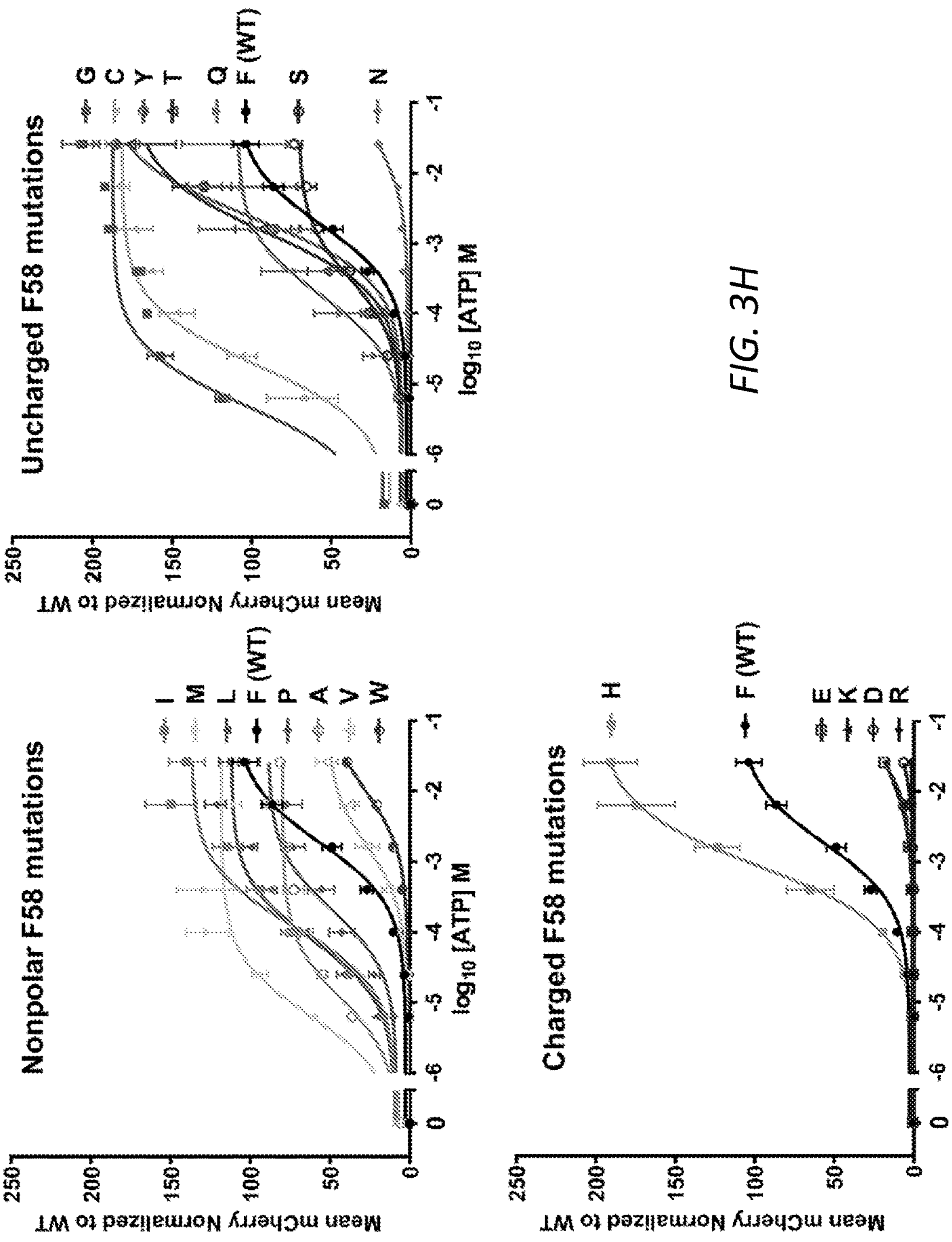

In summary, none of the tested combinations of mutations was superior to the original set of 10 selected human P2Y2 receptor mutants, which provided a range of improved sensitivity to physiological concentrations of eATP associated to inflammation. Mutations at F58$^{1.57}$, N116$^{3.35}$, F307$^{7.54}$ and Q165$^{4.57}$ contributed the most to the increased sensitivity to eATP of the human P2Y2 receptor via independent mechanisms involving increased receptor expression (F58$^{1.57}$), stabilization of the active receptor conformation (N116$^{3.35}$ and F307$^{7.54}$) and improved interactions with ATP (Q165$^{4.57}$). All 20 amino acids were later tested at residue F58$^{1.57}$, which revealed a diversity of eATP-induced signaling phenotypes (FIG. 3H). Collectively, these findings shed new light on the molecular mechanisms that control human P2Y2 receptor activity, while they illustrate the potential of applying directed evolution for the functional characterization of GPCRs.

Figure 4A:
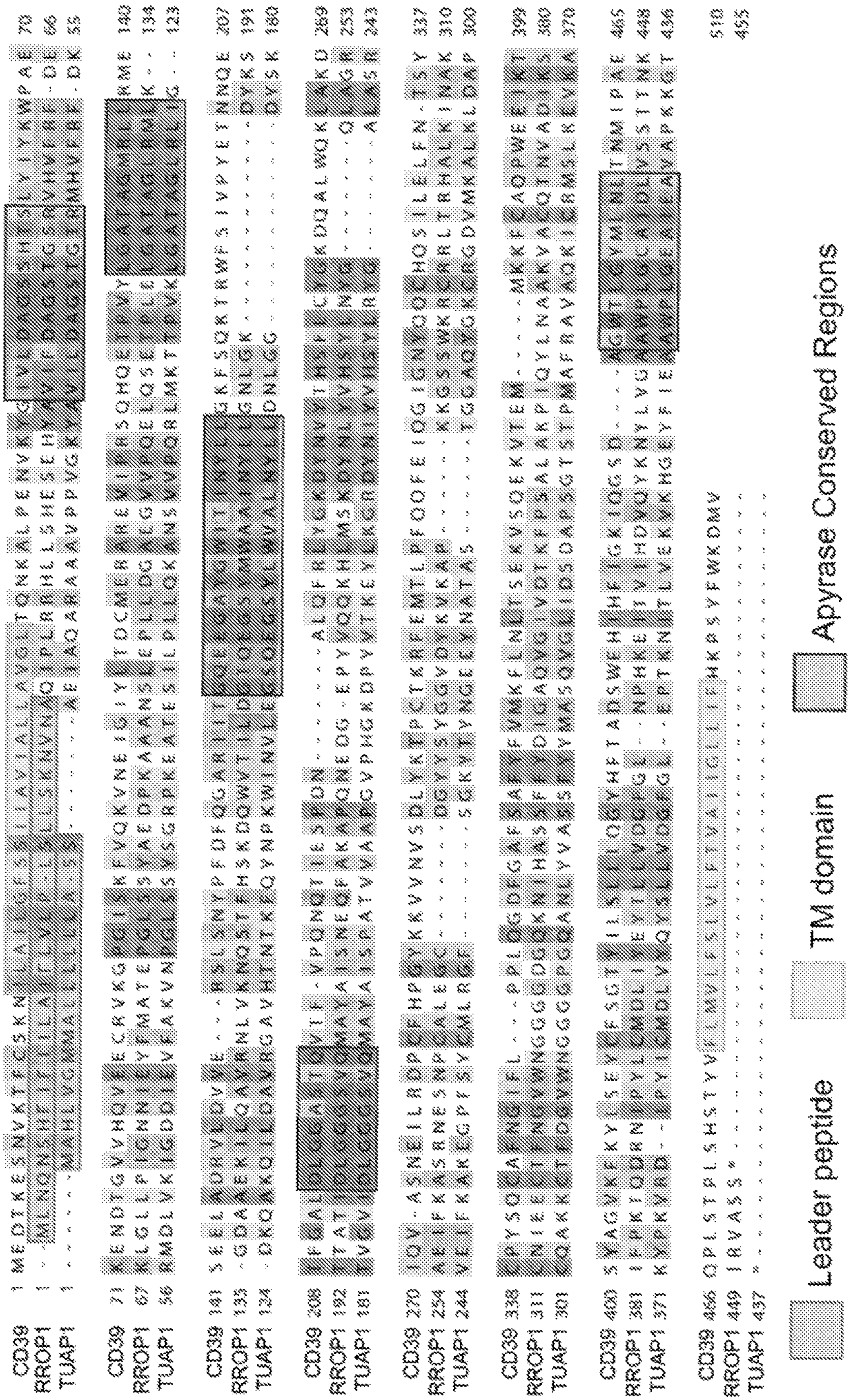
FIGS. 4A-F: eATP-responsive secretion of ATPase by engineered yeast. (A) Sequence Alignment of Apyrase Genes. Human ENTPD1 (CD39; SED ID NO: 19), potato apyrase (RROP1; SED ID NO: 20) and wheat apyrase (TUAP1; SED ID NO: 21) were aligned using MUSCLE, in the MEGA6 alignment explorer. (B) Therapeutic Response Elements. Shown are SEQ ID NOs: 23-27. (C) Cell lysates from yeast strains constitutively expressing potato apyrase (RROP1) or wheat apyrase (TUAP1), or not expressing any apyrase (Vector). Bands correspond to the C-terminal HA-tag on apyrase, RROP1 was expected at 48 kDa without the N-terminal alpha-factor signal peptide, or 57 kDa with the signal peptide. TUAP1 was expected at 46 kDa without the signal peptide, 55 kDA with the signal peptide. Arrow indicates the cytoplasmic protein Pgk1 used as a loading control. (D) 5 μL of supernatant from strains constitutively secreting potato apyrase (RROP1) or wheat apyrase (TUAP1) were incubated for 30 minutes with ATP 50 μM in a 50 μL total reaction volume, and residual ATP was quantified; the yeast parent strain that does not express apyrase was used as a negative control (CB008). Representative of three biological replicates each, error bars represent the standard deviation, *P <0.001. (E) Engineered human P2Y2 receptor activation was functionally coupled to the expression of RROP1 Apyrase, utilizing the mating-responsive promoter pFUS1. Upon activation of the receptor by eATP, Apyrase is expressed and secreted thank to the signal peptide to facilitate secretion by the yeast. Secreted apyrase dephosphorylates extracellular ATP, into ADP and AMP, in turn shutting off the gene circuit. (F) Engineered yeast strains harboring a P2Y2/RROP1 gene circuit were incubated for 16 hours with the indicated concentration of ATP. ATPase activity was quantified by incubating 5 μL culture supernatant with 50 μM ATP for 30 minutes in a 50 μL reaction, then measuring residual ATP. ATPase Unit=1 μmol of ATP to ADP per minute. Left to right are AP-P4 (WT); APTM-3 (N116S); APH1-1 (F58C C60Y G310A); APH1-3 ($F58^1$); APTM-2 (L59I C119S); APTM-1 (Q165H); APH7-1 (K240N F307S); Constitutive apyrase (BS029). "Constitutive" indicates yeast strains that express RROP1 under the control of the strong constitutive pTDH3 promoter. Data is the mean of 3 biological replicates performed on separate days, error bars represent the standard deviation. *P<0.05 vs WT response at the same ATP concentration.
Figure 4B:
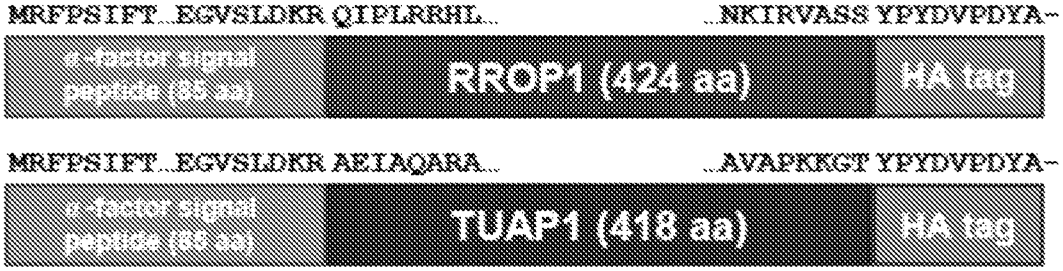

Example 3. EATP-Driven Dose-Dependent Induction of Secreted ATPase Activity in Synthetic Yeasts We next incorporated a therapeutic response element in the yeast synthetic gene circuit responsive to eATP. We focused on apyrases, which hydrolyze pro-inflammatory eATP and participate in its conversion into immunosuppressive adenosine (26). We selected the apyrase encoded by RROP1 in potato (*Solanum tuberosum*) (FIG. 4A), which has potent ATPase activity and reduces inflammation in a mouse model of IBD when delivered interperitoneally (48). Apyrase has also been identified in wheat (49), thus we selected apyrase from *Triticum urartu* (referred to TUAP1 here) based on its sequence homology to RROP1 in apyrase conserved regions (FIG. 4A). To enable secretion by yeast, we replaced the endogenous apyrase N-terminal signal peptide by the MFal signal peptide, and added a C-terminal HA tag to monitor expression (FIG. 4B).

Figure 4C:
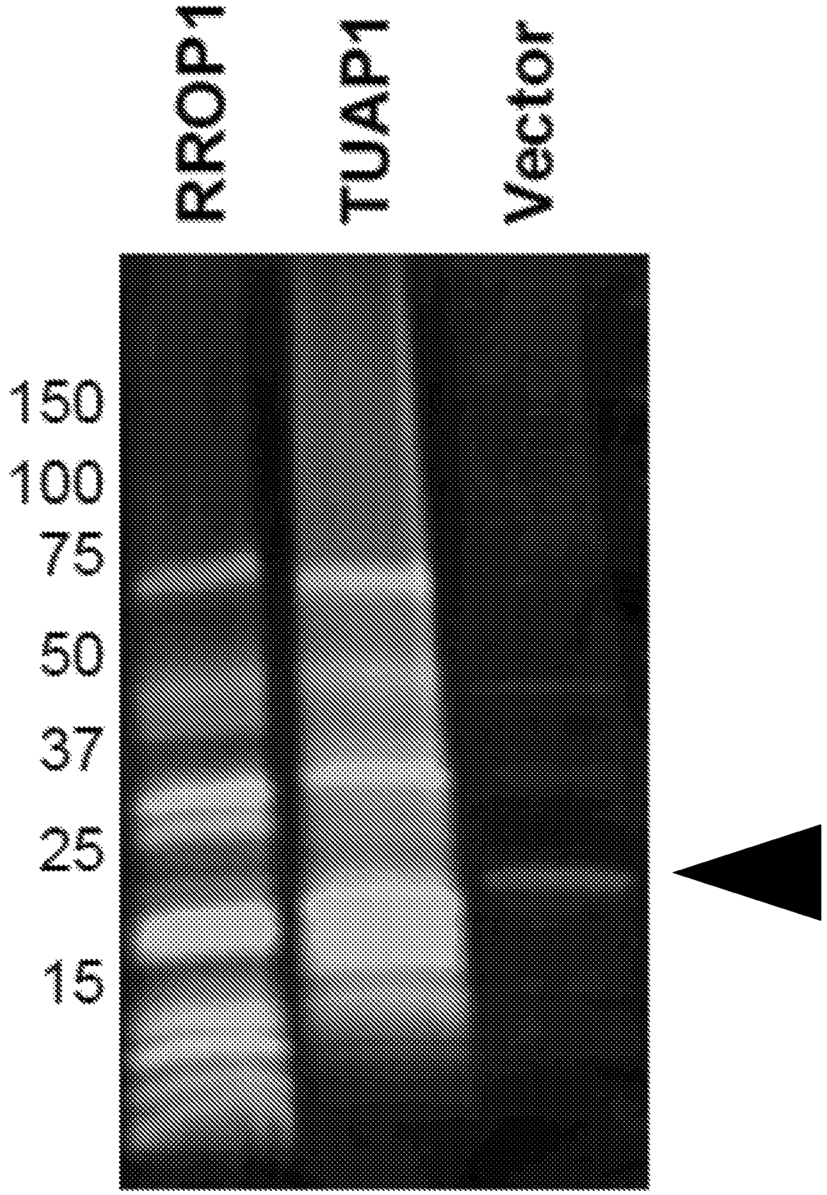

We first incorporated each modified apyrase gene under the control of a strong constitutive promoter into the yeast genome. The analysis of protein expression detected multiple protein bands, suggesting that the apyrases are partially degraded when expressed in yeast (FIG. 4C). However, commercially available potato apyrase displays bands at 15 and 25 kDa, and apyrases expressed in yeast are glycosylated, resulting in multiple protein bands (50).

Figure 4D:
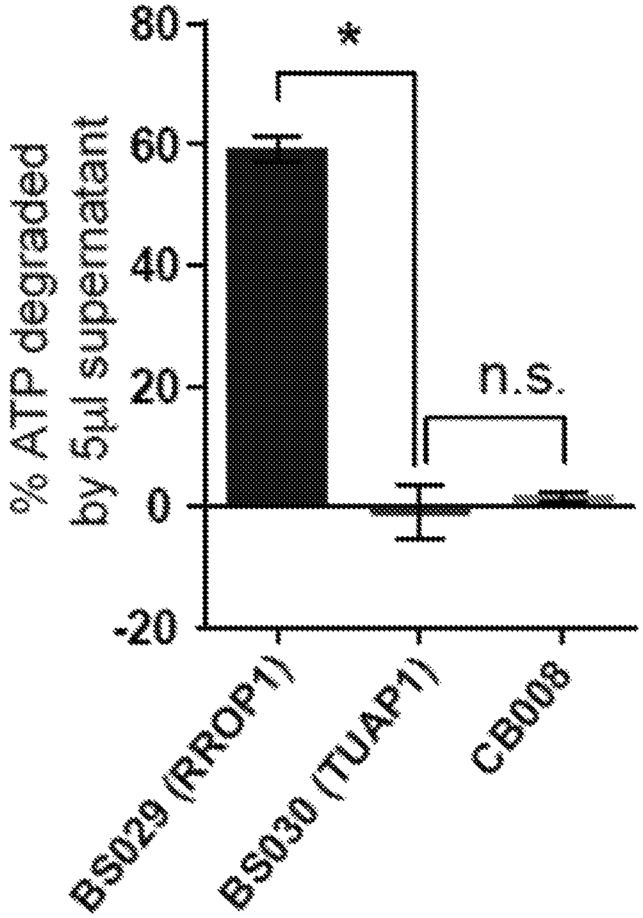

Culture supernatants from yeasts expressing RROP1 (BS029) showed higher ATPase activity than those of TUAP1-expressing yeasts (BS030) (FIG. 4D). When compared to commercial apyrase, culture supernatants from RROP1-expressing yeasts showed a relative ATPase activity equivalent to ~280 μM commercial apyrase/μL raw supernatant, while those of TUAP1-expressing yeasts showed an ATPase activity equivalent to <62.5 μM commercial apyrase/μL raw supernatant (FIGS. 9A-B). Thus, we chose RROP1 as a therapeutic response element for subsequent studies.

Figure 4E:
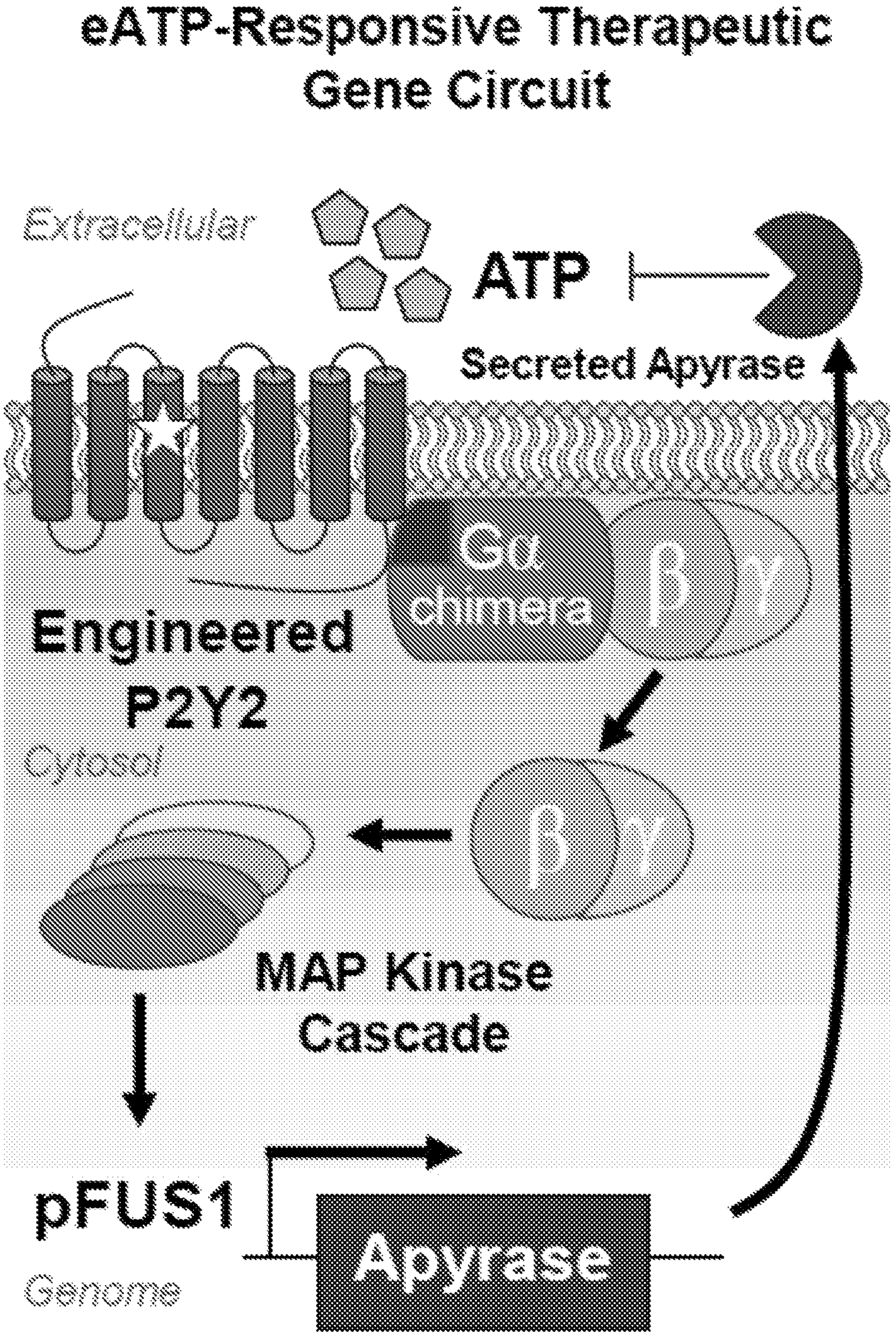
Figure 4F:
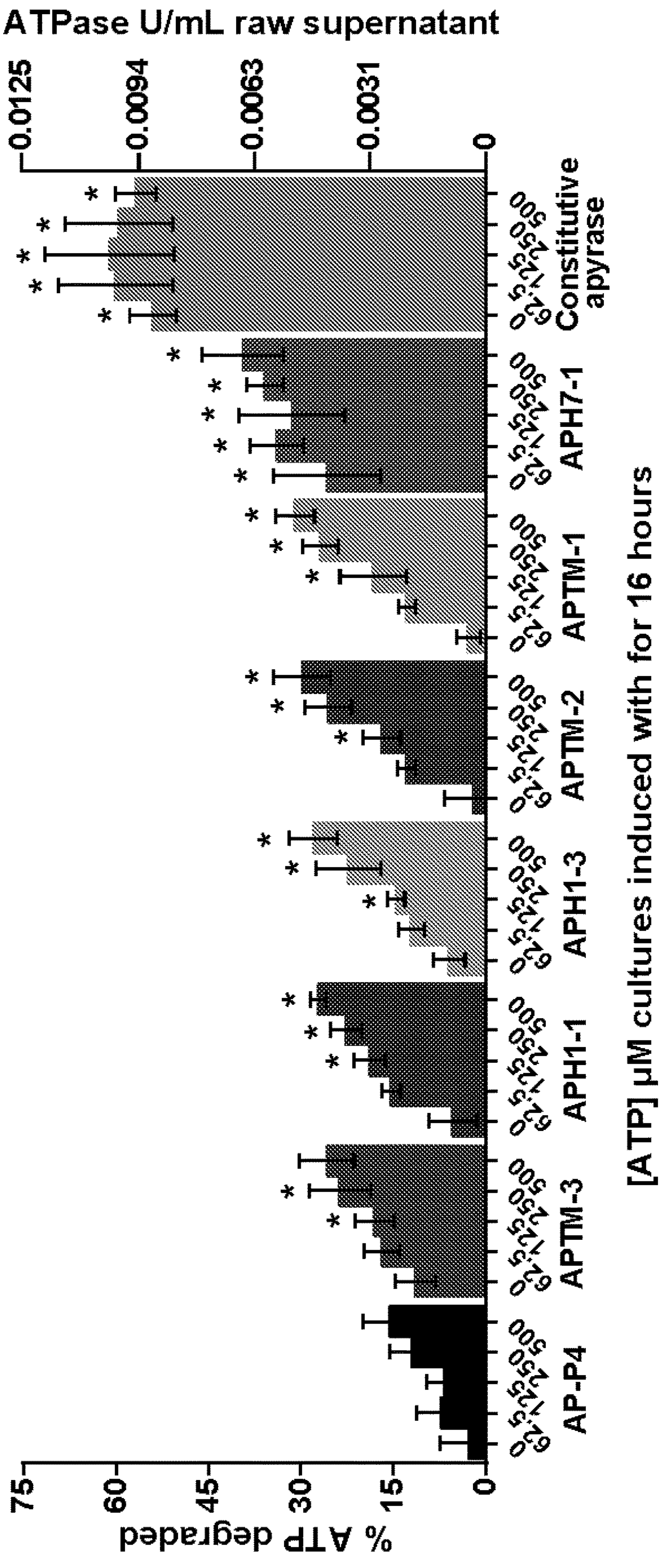

We then co-introduced sensing (P2Y2) and responding (RROP1) elements into the genome of the same yeast strains using a CRISPR/Cas9-based approach. We selected 6 human P2Y2 receptor mutants for integration into the yeast genome based on their low EC50, high dynamic range, and high maximum activation. We also removed the HygB selection marker from the yeast genome, to ensure that the final strain would not contain an antibiotic resistance gene while retaining uracil auxotrophy, an important consideration for the biocontainment and safety of an engineered microbe.

eATP induced, in a dose-dependent manner, ATPase enzymatic activity in culture supernatants from yeast strains containing the P2Y2-RROP1 gene circuit (FIG. 4E,F). Moreover, the ATPase activity was higher in yeast strains expressing human P2Y2 receptors engineered by directed evolution than in the strain expressing the human WT P2Y2 receptor. For example, at 125 μM ATP, we detected a 2.2- to 4.7-fold increase in ATPase activity in yeast strains harboring engineered human P2Y2 receptors while at the maximum eATP concentration investigated a 1.7- to 2.5-fold increase was detected (Table 5).

We used a yeast strain constitutively overexpressing RROP1 (strain BS029) to estimate the theoretical maximum of secreted ATPase. At 500 μM ATP, strains harboring engineered human P2Y2 receptor mutants showed 45%-69% of the ATPase activity detected with the BS029 constitutively secreting strain; yeast strains harboring the human WT P2Y2 receptor showed only 27% ATPase activity. Collectively, these findings show that through the combination of directed evolution and gene-circuit engineering we generated yeast strains that secrete functional ATPase in response to physiological levels of eATP.

TABLE 5

| Apyrase Secretion Relative to WT P2Y2 Strain | | | | | | |
|---|---|---|---|---|---|---|
| μM ATP | APTM-3 | APH1-1 | APH1-3 | APTM-2 | APTM-1 | APH7-1 |
| 0 | 4.1 | 1.9 | 2.1 | 0.7 | 1.0 | 9.2 |
| 62.5 | 2.3 | 2.1 | 1.7 | 1.8 | 1.8 | 4.7 |
| 125 | 2.7 | 2.8 | 2.2 | 2.6 | 2.8 | 4.7 |
| 250 | 2.0 | 1.9 | 1.9 | 2.1 | 2.2 | 3.0 |
| 500 | 1.7 | 1.7 | 1.8 | 1.9 | 2.0 | 2.5 |

Represented as fold-differences versus strain AP-P4. Apyrase data measured as % ATP degraded (ATPase activity), with data from FIG. 4.

Example 4. EATP-Responsive Synthetic Yeast Probiotics Ameliorate Intestinal Inflammation We then evaluated the anti-inflammatory activity of the engineered yeast probiotics using a murine experimental model of IBD. Specifically, we tested the APTM-3 engineered yeast strain that expresses apyrase in an eATP-dependent manner. We selected this yeast strain because it secretes low levels of apyrase when not stimulated, and because the increased responsiveness to eATP can be directly connected to a single mutation in P2Y2 with a known mechanism of action (N116S3.35). Moreover, when APTM-3 was stimulated with eATP the ATPase activity detected was greater than or similar to the one detected in other engineered P2Y2-RROP1 strains.

Figure 10A:
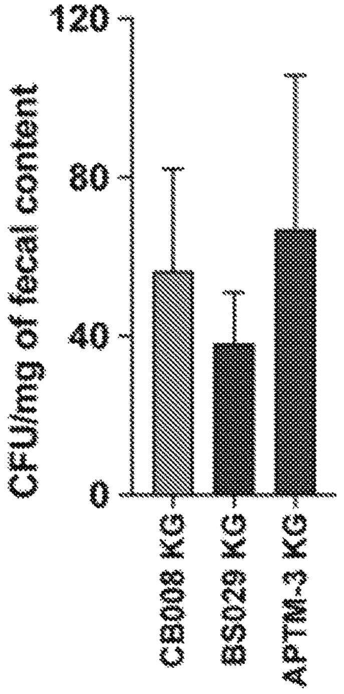
FIGS. 10A-D: Synthetic yeasts probiotics are viable in the mouse gut. (A) Colony forming units per mg of stool collected after the 6 hours after oral gavage to the mice with either CB008 KG, BS029 KG or APTM-3 KG yeast strains. (B) ATP relative levels in the specified portions of the gut of Naïve and TNBS induced mice. (C) mCherry positive yeasts (% of total GFP yeast) measured by flow cytometry in the fecal content of the specified portion of the gut after 2 hours from oral gavage to naïve mice with ATP induced TM3 strain TM-3 KG (right). ATP levels were measured in the same portions of the gut. (D) mCherry positive yeasts (% of total GFP yeast) quantified by flow cytometry in the fecal content of the specified portion of the gut 2 hours after oral gavage with TM-3 KG or P4 KG (WT) yeast strains.

We first evaluated the viability of the engineered yeasts in the murine digestive tract. To address this point, we incorporated an antibiotic resistance cassette to the CB008, BS029 and APTM-3 engineered yeast strains, to generate kanamycin-resistant CB008 KG, BS029 KG and APTM-3 KG strains which can be easily quantified in fecal cultures. Six hours after the administration of CB008 KG, BS029 KG or APTM-3 KG yeasts by gavage (of $2\times10^8$ cfu) we detected viable antibiotic-resistant yeasts in feces (FIG. 10A).

Figure 5B:
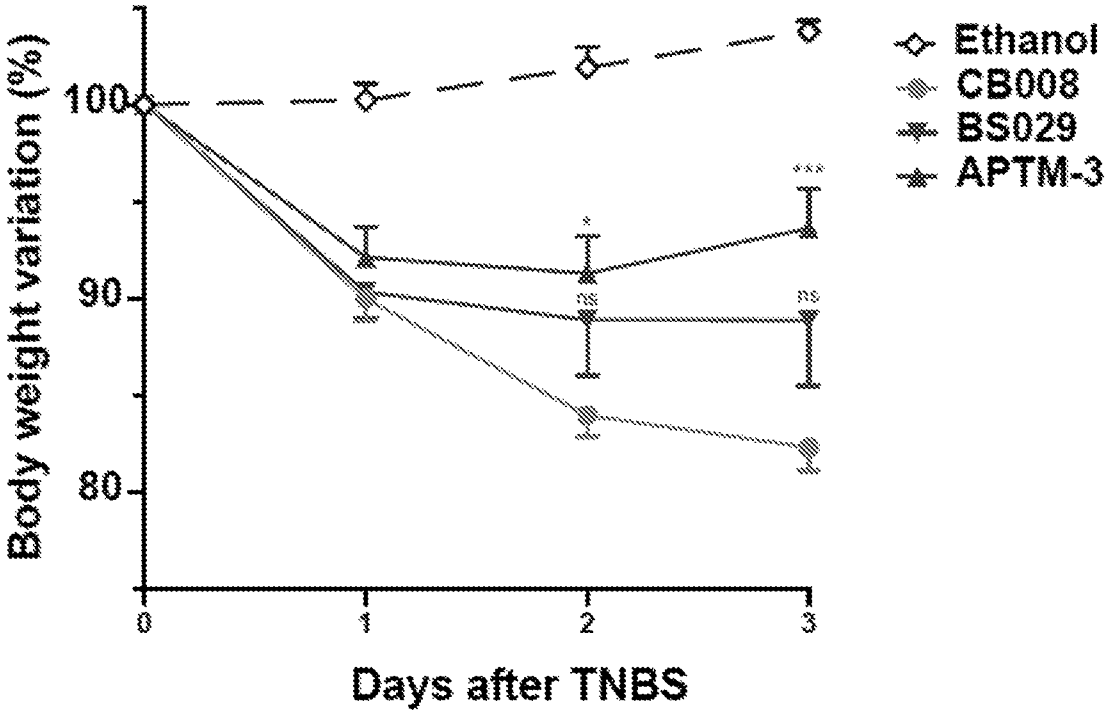
Figure 5C:
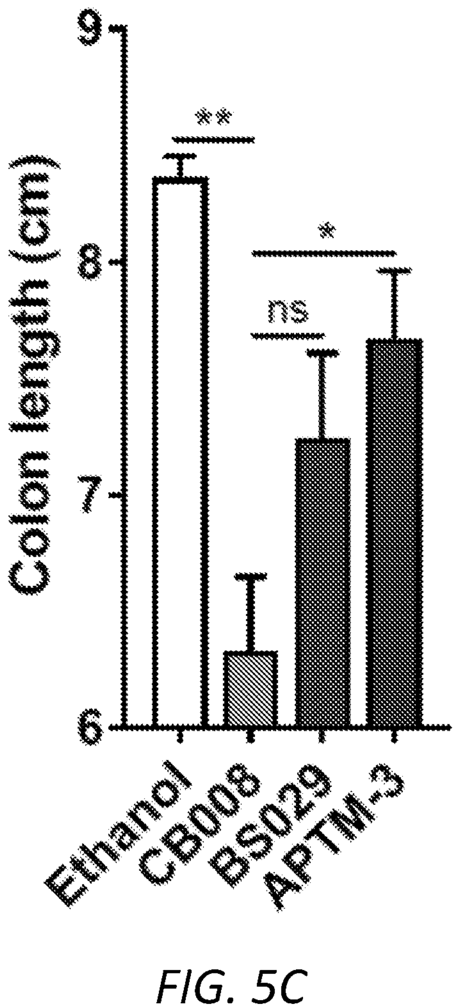
Figure 5D:
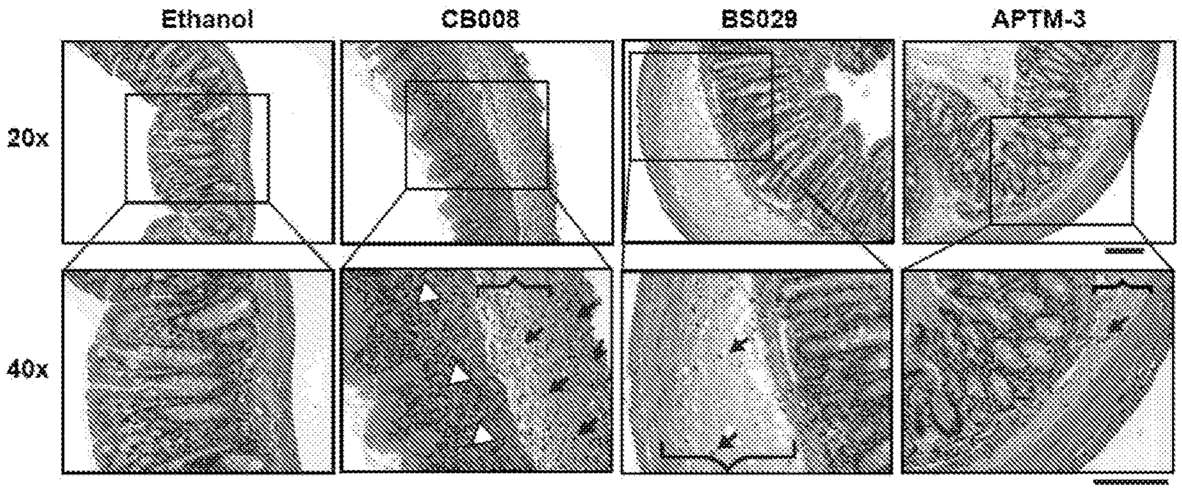
Figure 5E:
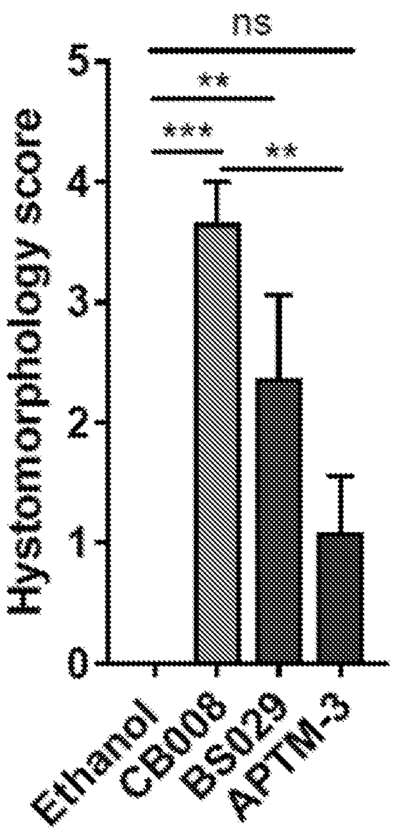
Figure 10B:
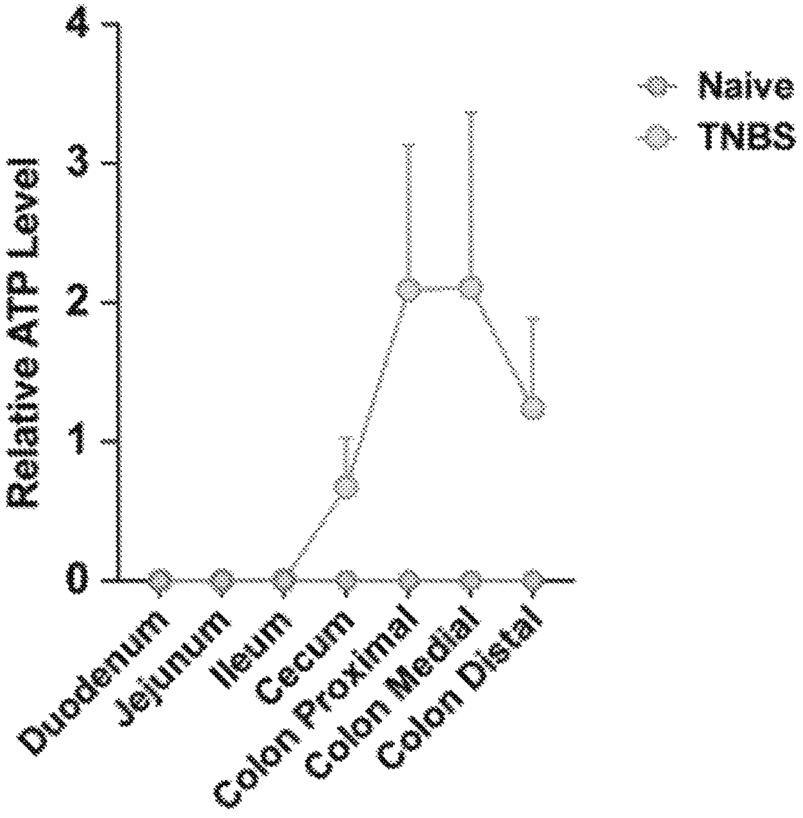
Figure 10C:
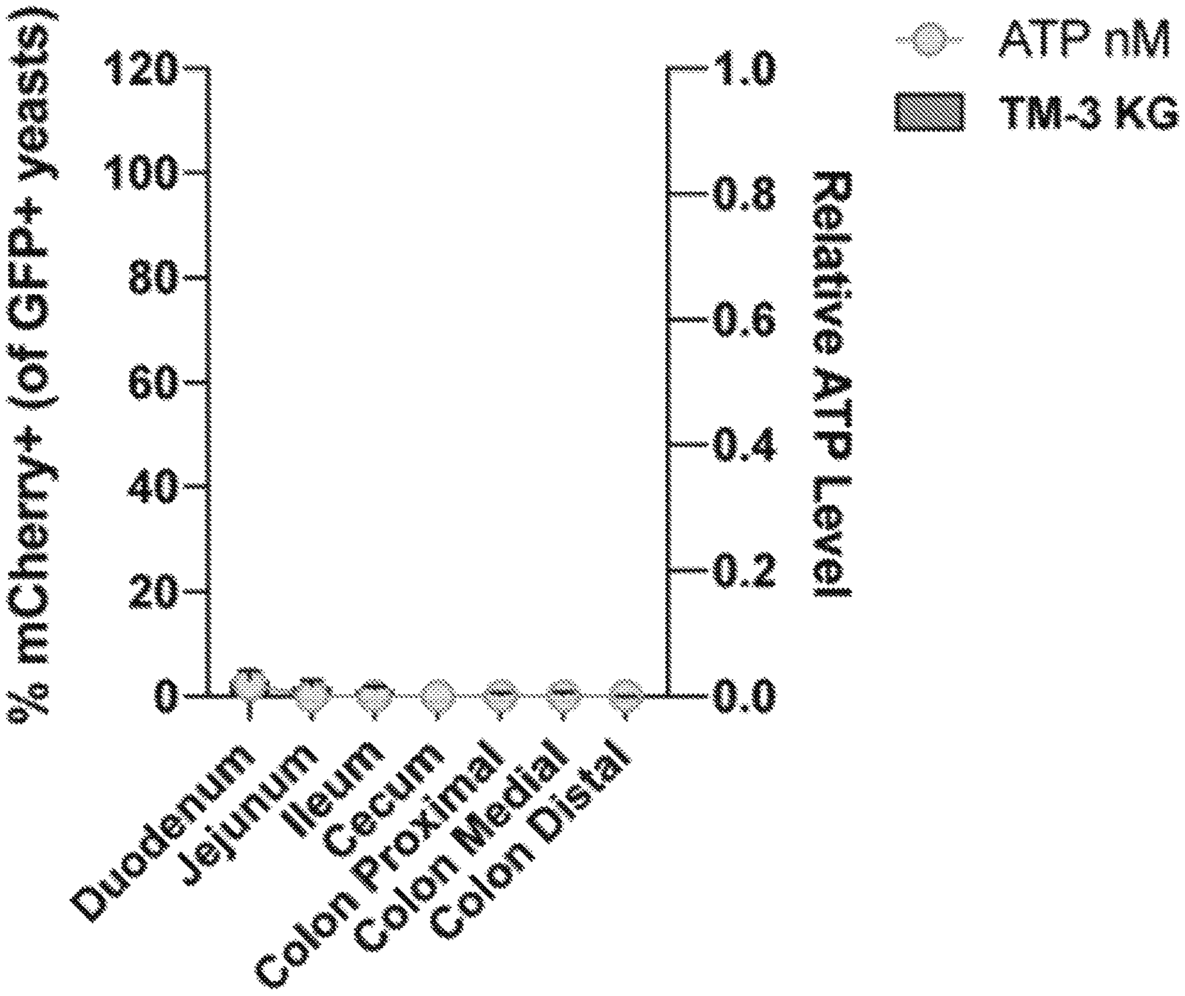
Figure 10D:
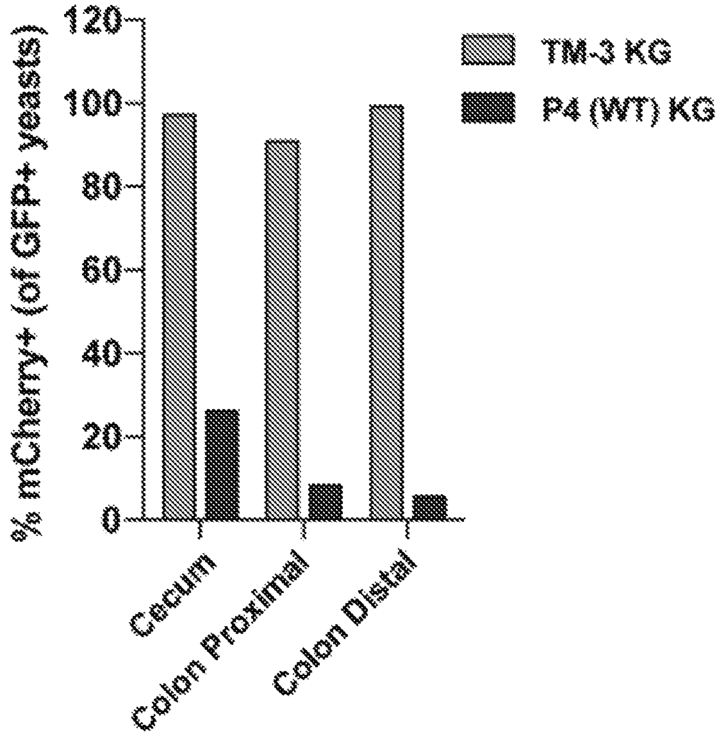

Increased local eATP levels are associated to intestinal inflammation (24, 25) (FIG. 10B). Thus, to analyze the activation of P2Y2 signaling in engineered yeasts during experimental colitis, we used the TM-3 yeast strain in which the activation of mutant TM-3 P2Y2 receptor by eATP induces mCherry expression; as a control we used the BS035 strain which constitutively expresses mCherry (FIG. 1C). For these experiments we also incorporated an additional cassette driving constitutive GFP expression, to detect the administered yeasts irrespectively of their eATP-driven mCherry expression. We detected mCherry expression in the TM-3 engineered yeasts in the cecum, proximal and medial colon concomitant with increased local eATP levels in TNBS mice (FIG. 5A). Of note, mCherry expression was not induced in TM-3 engineered yeasts administered to naive mice in which eATP levels were not locally increased (FIG. 10C). Conversely, mCherry expression was detected throughout the gastrointestinal tract of mice that received the BS035 yeast strain, regardless of eATP levels (FIG. 5A). Moreover, when we compared mCherry expression under the control of WT or mutant TM-3 P2Y2 in vivo, we detected higher mCherry expression in yeast expressing the mutant TM-3 P2Y2, highlighting the importance of P2Y2 in vitro evolution to enable the detection of eATP levels associated to intestinal inflammation (FIG. 10D). Taken together, these data indicate that the engineered yeast are viable in the digestive tract, and that the TM-3 P2Y2 mutant responds to eATP levels associated to intestinal inflammation.

We first evaluated the therapeutic value of the engineered yeasts in the experimental model of TNBS-induced colitis, in which C57BL/6J mice are pre-sensitized and colitis is induced by rectal injection of TNBS 7 days later. We administered the APTM-3 engineered yeast strain in which apyrase is induced following the activation of mutant TM-3 P2Y2 by eATP daily by gavage ($2\times10^8$ cfu) starting on the day of topical sensitization with TNBS; the parent CB008 yeast strain and the BS029 engineered yeast strain that expresses apyrase constitutively were used as controls. APTM-3 administration ameliorated TNBS-induced colitis, as indicated by the evaluation of weight loss, colon shortening and the histological analysis of intestinal pathology (FIGS. 5B-E).

Figure 5F:
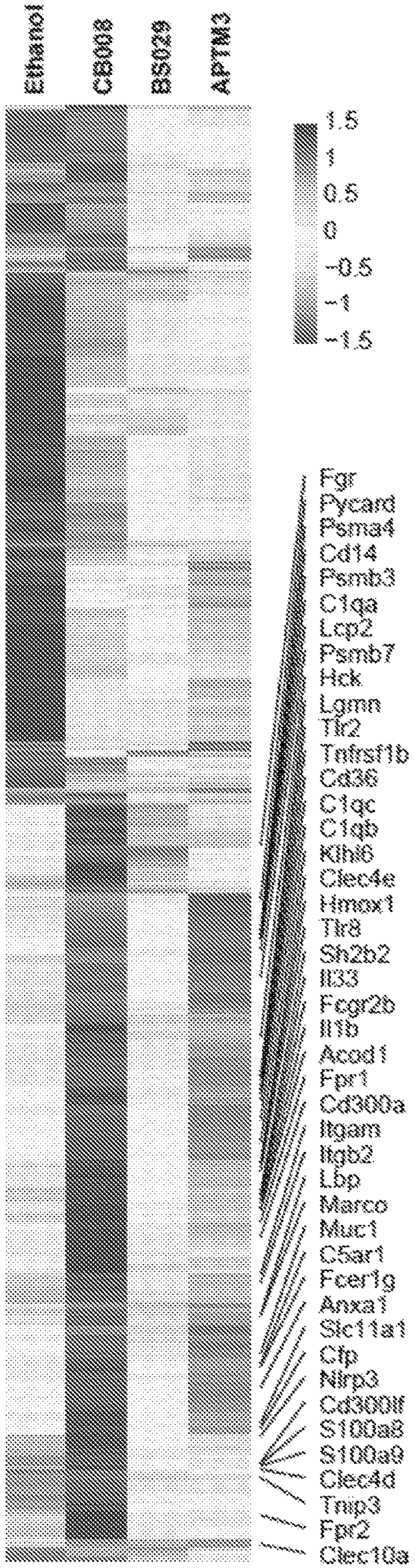
Figure 5G:
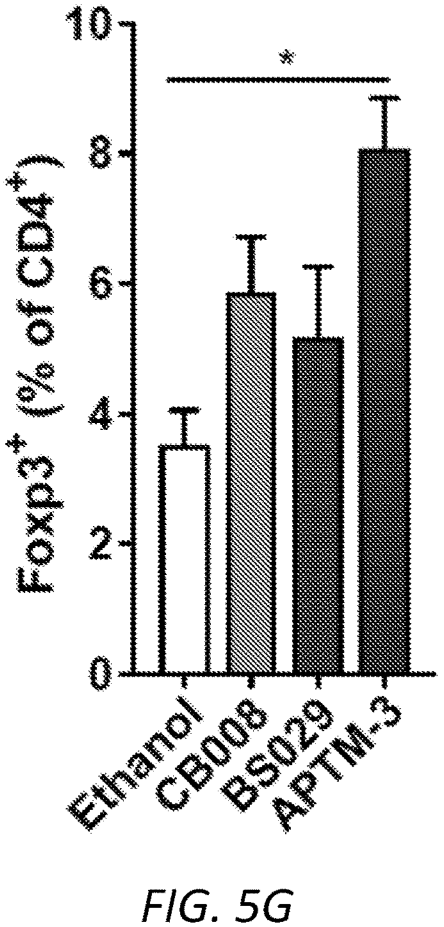
Figure 5H:
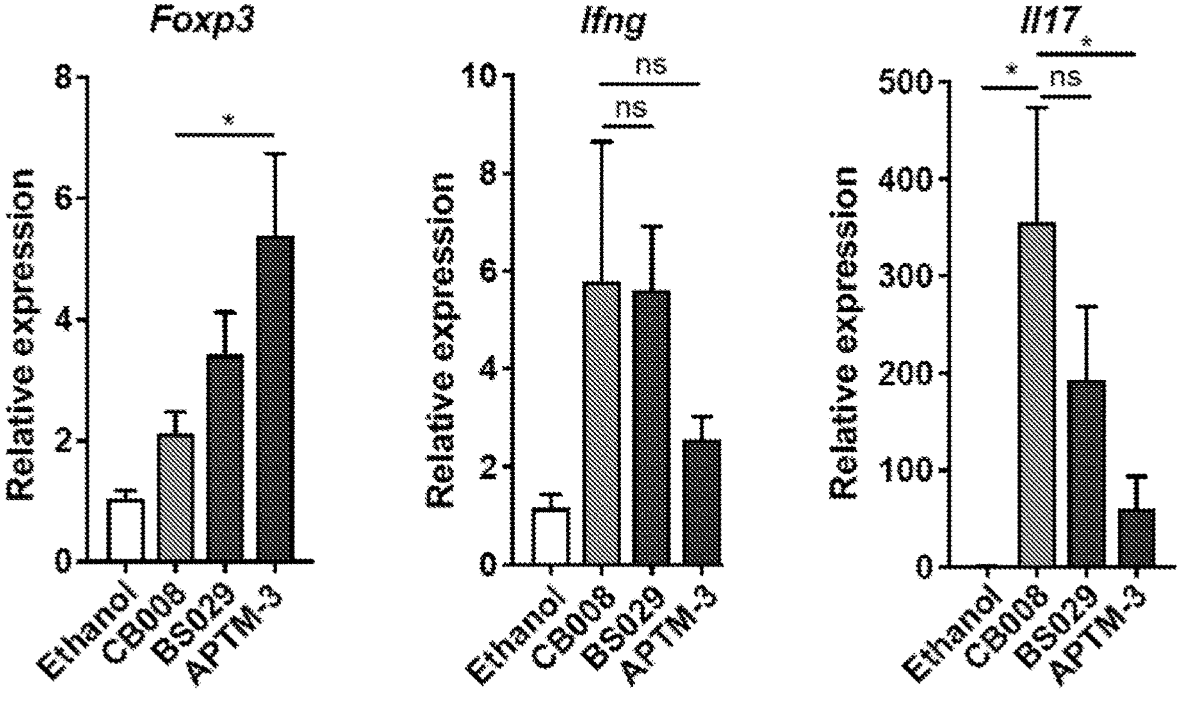

The analysis of colon samples by RNA-Seq detected decreased expression of pro-inflammatory genes in mice treated with apyrase-producing yeast strains BS029 and APTM-3; these effects were more pronounced in the APTM-3 group (FIG. 5F). Indeed, treatment with the ATPM-3 strain, but not with BS029, led to the up-regulation of FoxP3+ Tregs in mesenteric lymph nodes, concomitant with a reduced expression of the pro-inflammatory IFNg and IL-17 cytokines associated to intestinal inflammation (51, 52) (FIGS. 5G-H).

Figure 5I:
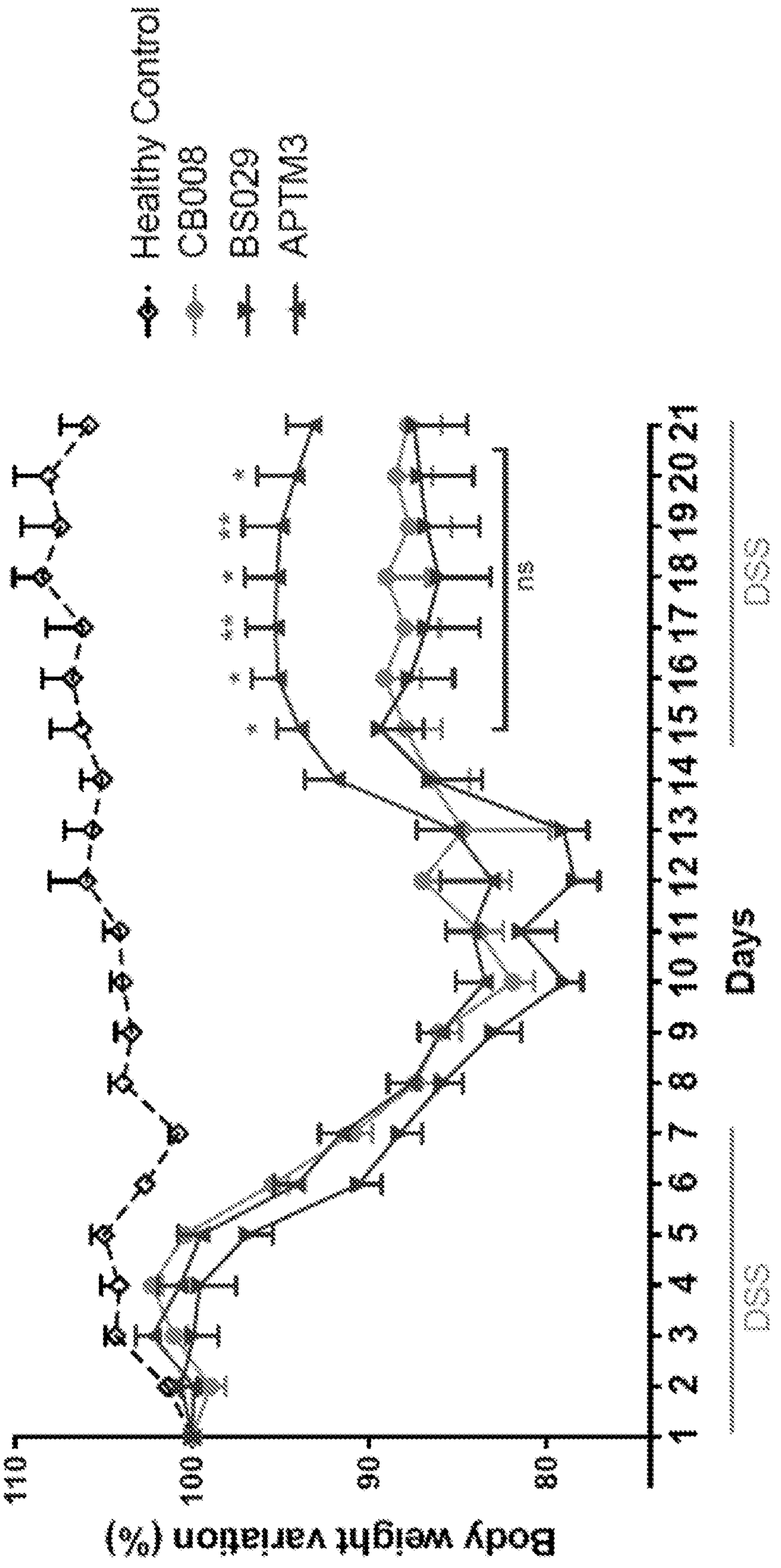
Figure 5J:
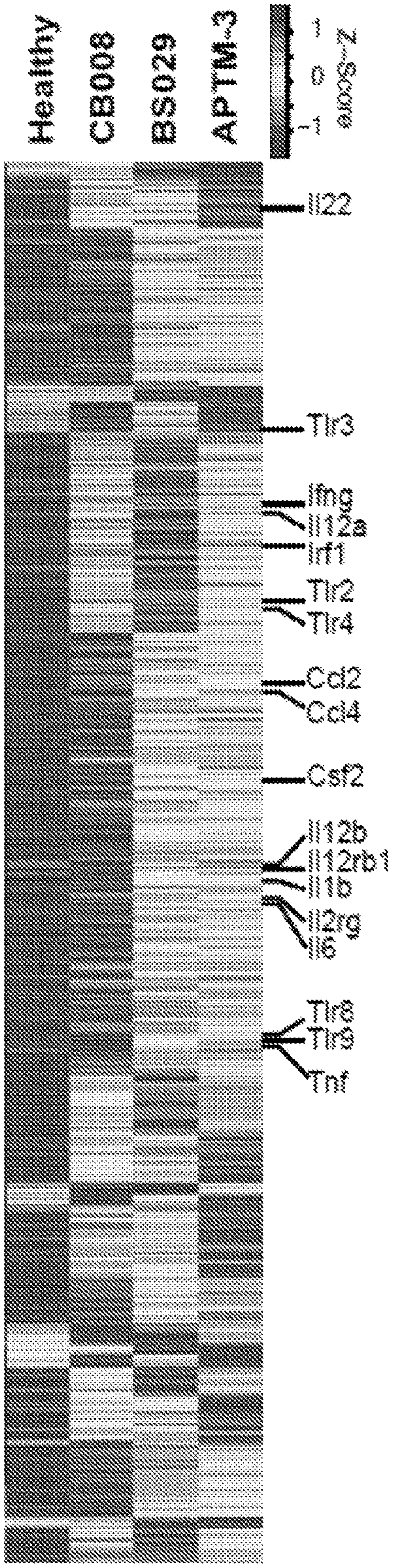
Figure 5K:
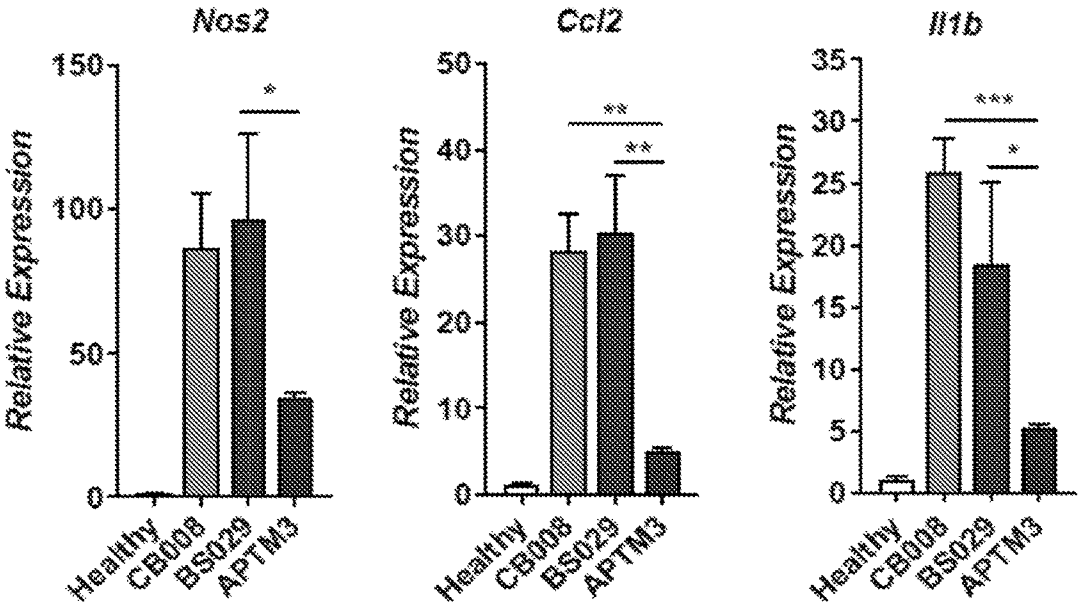

To further evaluate the therapeutic potential of engineered apyrase-expressing yeasts we used the model of colitis induced with two rounds, seven days apart, of dextran sodium sulfate (DSS) administered in drinking water (53). We administered yeast orally starting on the day in which DSS administration was initiated. Treatment with APTM-3, but not with BS029, interfered with the weight loss associated to DSS-induced colitis (FIG. 5I). Moreover, the transcriptional analysis of colon samples by qPCR and Nanostring revealed that APTM-3 treatment resulted in the decreased expression of genes associated to IBD and intestinal inflammation (51, 52, 54, 55) (FIGS. 5J,K). Taken together, these findings demonstrate that eATP-responsive yeasts harboring a synthetic P2Y2-RROP1 gene circuit ameliorate intestinal inflammation.

Figure 6A:
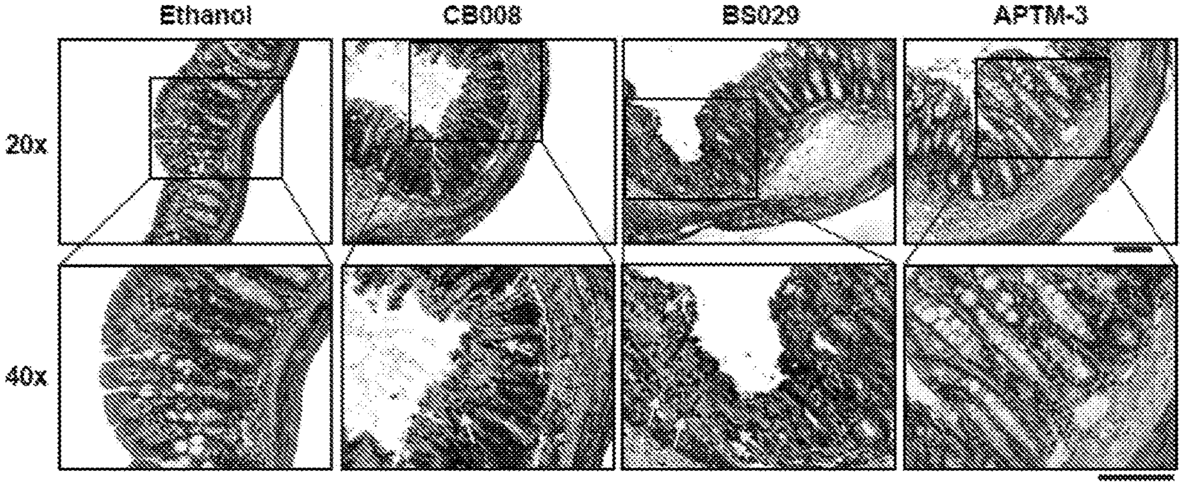
FIGS. 6A-H: eATP-responsive synthetic yeast probiotics limit fibrosis and dysbiosis. (A) Masson Trichrome staining for fibrosis, 20× (top) and 40× (bottom) magnification. Fibrotic regions are stained and highlighted with white arrows. Scale bars=100 μm. (B) Histology fibrosis score of mice from groups from (L) (n=4). (C—H) High-throughput gene-sequencing analysis of the microbial 16S rRNA gene performed by MiSeq on fecal samples. (C) Alpha-diversity of fecal microbiome. Shannon's Index, which compares differences in apha-diversity, was calculated at the highest sequence depth (4000 pb). *P<0.05; ns=not significant as determined by Kruskal-Wallis non parametric ANOVA test. (D-E) Beta-diversity. (D) Principal-coordinate analysis (PCoA) based on unweighted UniFrac metrics. (E) Unweighted UniFrac distances to Ethanol control group. *P<0.05 Permanova analysis. (F) Relative abundance of bacteria classified at a family-level taxonomy. (G) Relative abundance of Lachnospiraceae family and one of its genus *Roseburia*. (H) LEfSe p<0.05 for the APTM-3 vs CB008 comparison. Each cladogram represents all taxa detected at >0.1%, shown at the Kingdom phylogenetic level through the genus level. Light grey circles depict taxa present, but not enriched. Dark grey circles are enriched in APTM-3, and striped circles show enriched in CB008. **P<0.01; *P<0.05; ns=not significant as determined by one-way ANOVA followed by post-hoc tests Tukey's test.
Figure 6B:
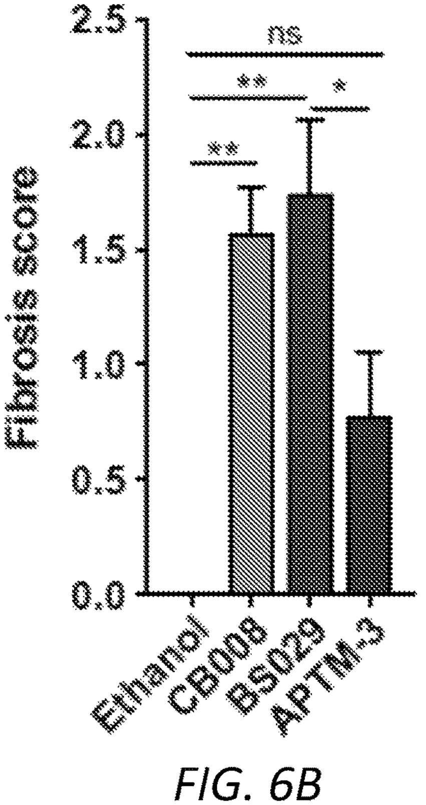

Example 6. eATP-Responsive Synthetic Yeast Probiotics Limit Colitis-Associated Fibrosis and Dysbiosis Fibrosis contributes to the pathogenesis of IBD (56-58). Although adenosine produced by the metabolism of eATP dampens inflammation, chronic activation of purinergic signaling driven by adenosine can promote fibrosis (26, 29). Thus, although yeast strains constitutively expressing apyrase show anti-inflammatory effects, they may also promote additional pathogenic responses avoidable by the use of yeast strains that produce apyrase in response local eATP levels. Indeed, we detected fibrotic lesions in the colon of mice treated with control CB008 and also with the constitutive apyrase-expressing BS029 yeast strains. However, we detected a significant reduction in fibrosis in mice treated with the eATP-inducible APTM3 engineered yeast strain (FIGS. 6A,B). These findings suggest that the controlled modulation of purinergic signaling is needed to manage intestinal inflammation and avoid unwanted deleterious side effects.

Figure 6C:
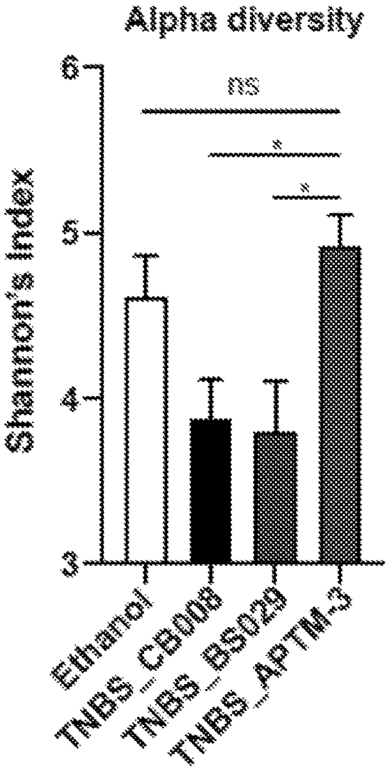

The microbiome plays an important role in intestinal physiology in health and disease (5). Moreover, purinergic signaling participates in gut microbiota-host communication (28, 30). Thus, probiotics engineered to act on an inducible and localized manner are likely to minimize disturbances on the gut microbiome. To investigate whether constitutive versus inducible apyrase production by engineered yeast strains differ on their effects on the gut microbiome, we performed 16S rRNA sequencing in fecal samples. In agreement with previous reports (59), the induction of colitis with TNBS reduced microbiome diversity within each sample as indicated by the analysis of the Shannon entropy index of alpha-diversity (FIG. 6C). A similar reduction in microbiome diversity was detected when we analyzed the effect of treatment with the BS029 yeast strain which produces apyrase constitutively. However, treatment with the APTM-3 engineered yeast strain expressing inducible apyrase resulted in microbiome diversity levels similar to those detected in naive mice (FIG. 6C).

Figure 6D:
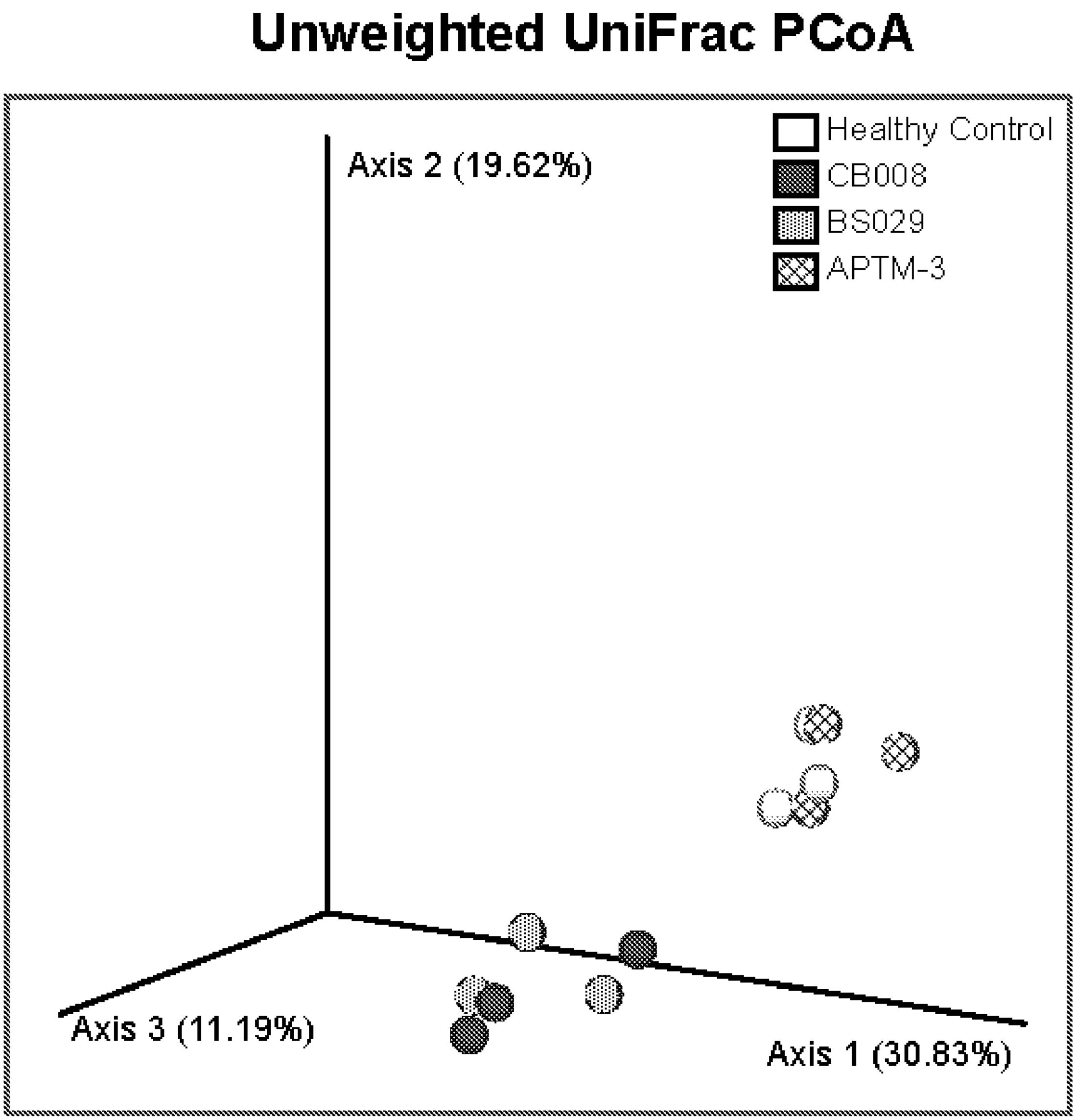
Figure 6E:
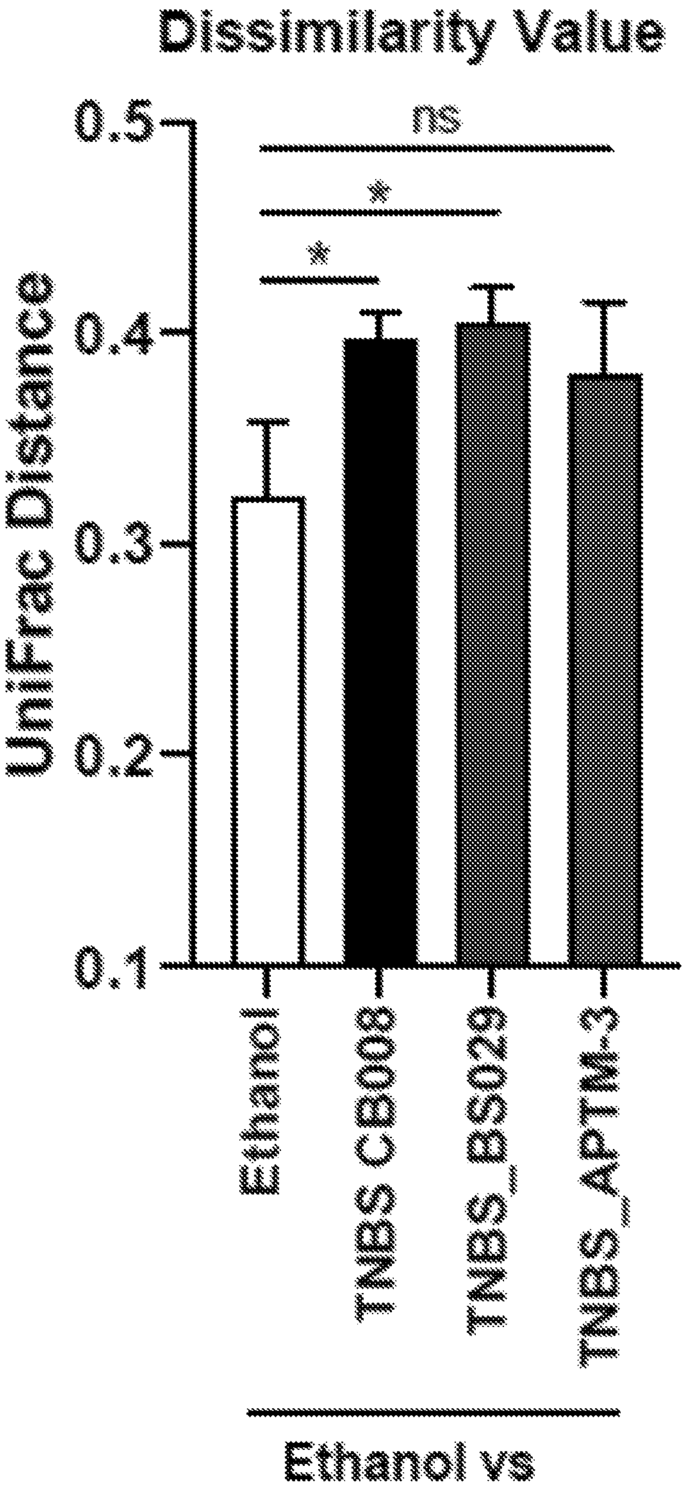

We then analyzed beta-diversity, which measures the differences in microbiome composition between samples, using the unweighted UniFrac distance metric that evaluates qualitative differences on microbial taxa, taking into account their phylogenetic relationship. Principal coordinate analysis (PCoA) visualization of permanova testing (FIG. 6D) and pair-wise UniFrac distances (FIG. 6E) revealed significant differences between the control group and TNBS mice treated with the CB008 control or the constitutive apyrase BS029 yeast strains. Strikingly, the analysis of beta-diversity revealed that TNBS mice treated with the APTM-3 engineered strain harbored a microbiome similar to that of mice in which TNBS colitis had not been induced, suggesting that the engineered yeast strain in which apyrase expression is induced by eATP re-establishes a healthy microbiome (FIGS. 6D-E).

Figure 6F:
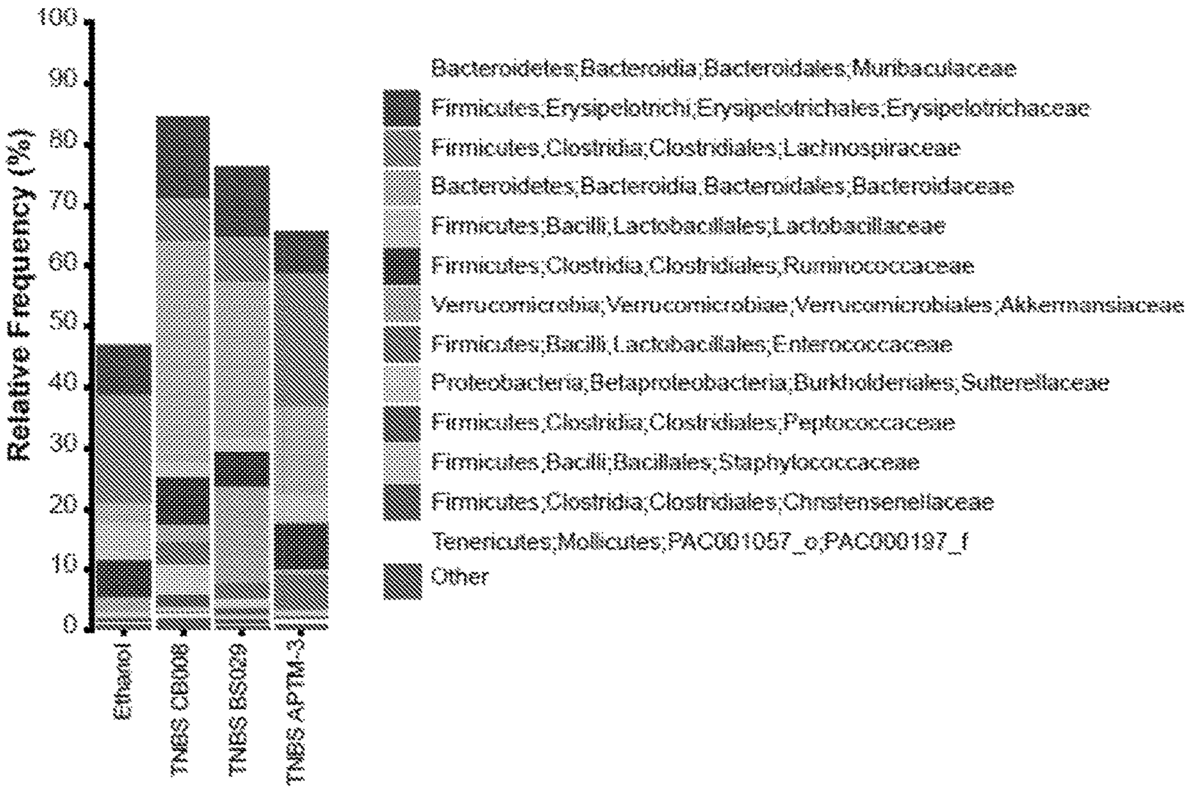
Figure 6G:
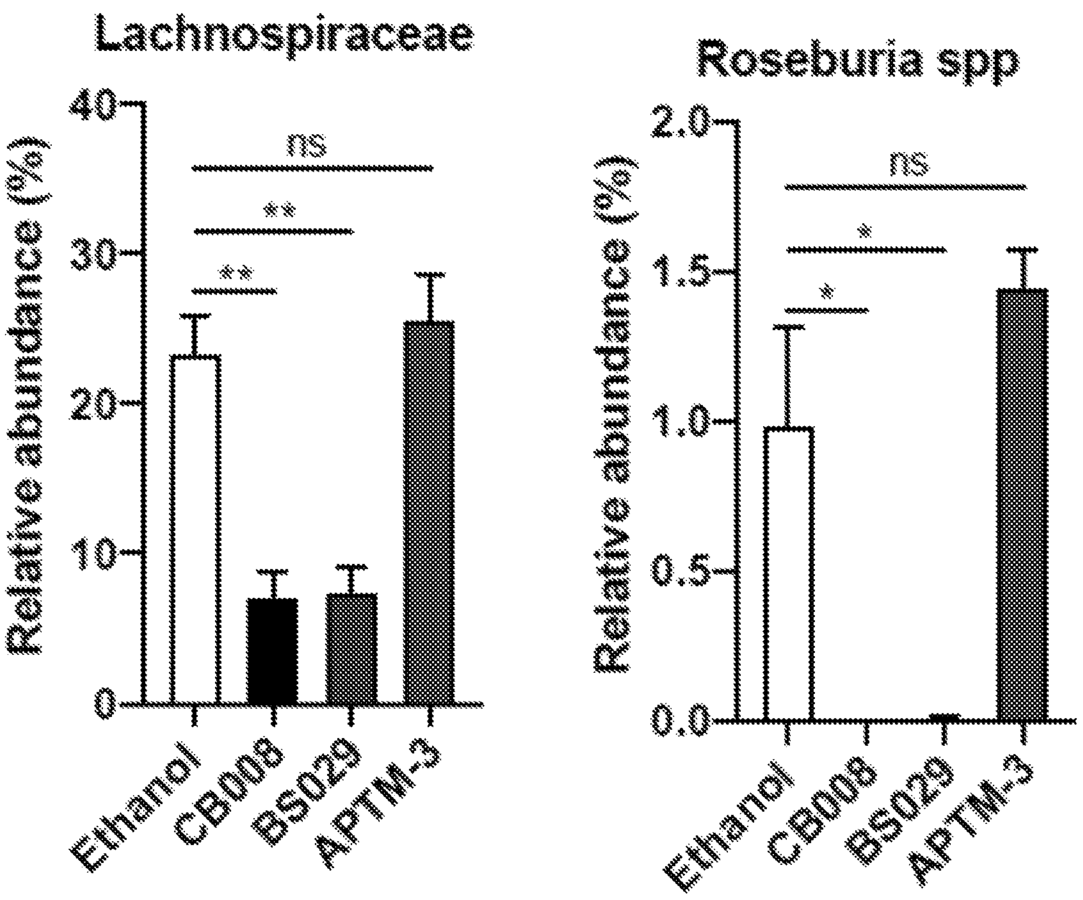
Figure 6H:
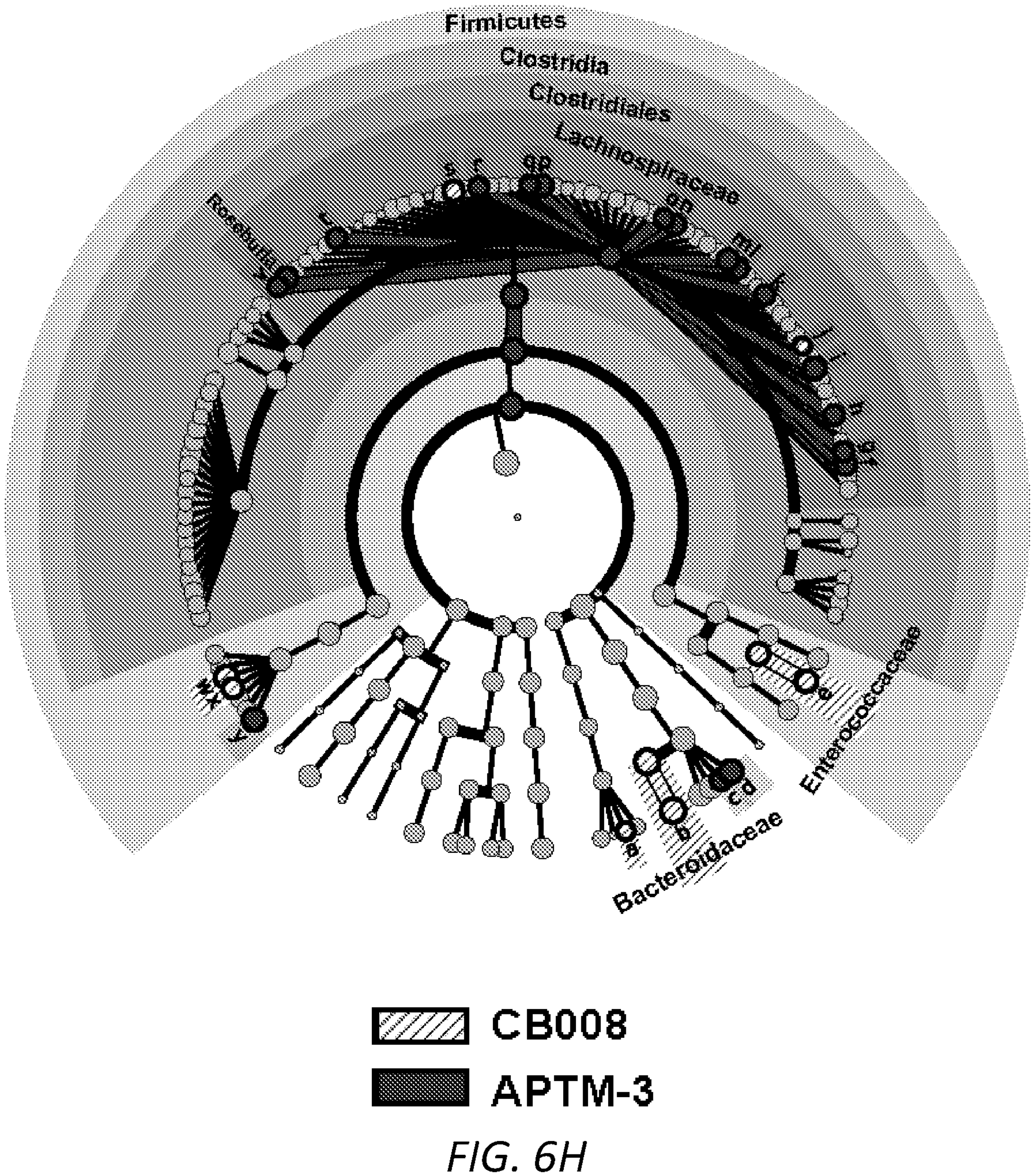

Finally, we analyzed the taxonomic composition of the microbiome in the different treatment groups. Several taxa of commensal bacteria have been shown to be decreased in IBD and ameliorate intestinal inflammation (4, 5, 60, 61). For example, Clostrodium cluster XIVa, associated with the induction of regulatory T cells (Tregs), is consistently depleted in people with IBD and acute colitis (62-64). We found that the Lachnospiraceae family, which is part of *Clostridium* cluster XIVa, was significantly reduced in TNBS mice treated with the CB008 and BS029 yeast strains, but not in TNBS mice treated with the APTM-3 strain expressing inducible apyrase (FIGS. 6F-H). Moreover, within the Lachnospiraceae family, the *Roseburia* genus was decreased in the CB008 and BS029 yeast strains, but not in APTM-3 treated TNBS mice. Of note, the *Roseburia* spp. has been shown to promote Treg development through a butyrate-dependent mechanism (65, 66). Taken together, these findings suggest that the inducible production of apyrase by the APTM-3 engineered yeast strain enables the anti-inflammatory effects of eATP depletion and adenosine production, without unwanted pathogenic side effects associated to fibrosis and microbiome dysregulation.

REFERENCES

1. H. Huang et al., Fine-mapping inflammatory bowel disease loci to single-variant resolution. Nature 547, 173-178 (2017).
2. M. F. Neurath, Targeting immune cell circuits and trafficking in inflammatory bowel disease. Nature immunology, (2019).
3. L. Jostins et al., Host-microbe interactions have shaped the genetic architecture of inflammatory bowel disease. Nature 491, 119-124 (2012).
4. J. Lloyd-Price et al., Multi-omics of the gut microbial ecosystem in inflammatory bowel diseases. Nature 569, 655-662 (2019).
5. J. M. Blander, R. S. Longman, I. D. Iliev, G. F. Sonnenberg, D. Artis, Regulation of inflammation by microbiota interactions with the host. Nature immunology 18, 851-860 (2017).
6. B. Lamas et al., CARD9 impacts colitis by altering gut microbiota metabolism of tryptophan into aryl hydrocarbon receptor ligands. Nat Med 22, 598-605 (2016).
7. H. Chu et al., Gene-microbiota interactions contribute to the pathogenesis of inflammatory bowel disease. Science (New York, N.Y.) 352, 1116-1120 (2016).
8. L. Cervantes-Barragan et al., *Lactobacillus reuteri* induces gut intraepithelial CD4(+)CD8alphaalpha(+) T cells. Science (New York, N.Y.) 357, 806-810 (2017).
9. W. S. Garrett, J. I. Gordon, L. H. Glimcher, Homeostasis and inflammation in the intestine. Cell 140, 859-870 (2010).
10. J. Suez, N. Zmora, E. Segal, E. Elinav, The pros, cons, and many unknowns of probiotics. Nat Med 25, 716-729 (2019).
11. T. S. Moon, C. Lou, A. Tamsir, B. C. Stanton, C. A. Voigt, Genetic programs constructed from layered logic gates in single cells. Nature 491, 249-253 (2012).

12. P. Siuti, J. Yazbek, T. K. Lu, Synthetic circuits integrating logic and memory in living cells. Nature biotechnology 31, 448-452 (2013).
13. J. Hasty, D. McMillen, J. J. Collins, Engineered gene circuits. Nature 420, 224-230 (2002).
14. A. A. Nielsen et al., Genetic circuit design automation. Science (New York, N.Y.) 352, aac7341 (2016).
15. C. J. Bashor et al., Complex signal processing in synthetic gene circuits using cooperative regulatory assemblies. Science (New York, N.Y.) 364, 593-597 (2019).
16. Y. Higashikuni, W. C. Chen, T. K. Lu, Advancing therapeutic applications of synthetic gene circuits. Current opinion in biotechnology 47, 133-141 (2017).
17. M. Mimee, A. C. Tucker, C. A. Voigt, T. K. Lu, Programming a Human Commensal Bacterium, *Bacteroides* thetaiotaomicron, to Sense and Respond to Stimuli in the Murine Gut Microbiota. Cell systems 1, 62-71 (2015).
18. B. Chen et al., Synthetic biology toolkits and applications in *Saccharomyces cerevisiae*. Biotechnology advances 36, 1870-1881 (2018).
19. B. P. Landry, J. J. Tabor, Engineering Diagnostic and Therapeutic Gut Bacteria. Microbiology spectrum 5, (2017).
20. N. Mao, A. Cubillos-Ruiz, D. E. Cameron, J. J. Collins, Probiotic strains detect and suppress cholera in mice. Science translational medicine 10, (2018).
21. D. T. Riglar et al., Engineered bacteria can function in the mammalian gut long-term as live diagnostics of inflammation. Nature biotechnology 35, 653-658 (2017).
22. P. F. Xia, H. Ling, J. L. Foo, M. W. Chang, Synthetic genetic circuits for programmable biological functionalities. Biotechnology advances, (2019).
23. K. Atarashi et al., ATP drives lamina propria T (H) 17 cell differentiation. Nature 455, 808-812 (2008).
24. B. D. Gulbransen et al., Activation of neuronal P2X7 receptor-pannexin-1 mediates death of enteric neurons during colitis. Nat Med 18, 600-604 (2012).
25. M. Idzko, D. Ferrari, H. K. Eltzschig, Nucleotide signalling during inflammation. Nature 509, 310-317 (2014).
26. M. C. Takenaka, S. Robson, F. J. *Quintana*, Regulation of the T Cell Response by CD39. Trends Immunol 37, 427-439 (2016).
27. I. D. Mascanfroni et al., Metabolic control of type 1 regulatory T cell differentiation by AHR and HIF1-alpha. Nat Med 21, 638-646 (2015).
28. M. Vuerich, S. C. Robson, M. S. Longhi, Ectonucleotidases in Intestinal and Hepatic Inflammation. Frontiers in immunology 10, 507 (2019).
29. C. Cekic, J. Linden, Purinergic regulation of the immune system. Nat Rev Immunol 16, 177-192 (2016).
30. A. Inami, H. Kiyono, Y. Kurashima, ATP as a Pathophysiologic Mediator of Bacteria-Host Crosstalk in the Gastrointestinal Tract. Int J Mol Sci 19, (2018).
31. S. G. Peisajovich, J. E. Garbarino, P. Wei, W. A. Lim, Rapid diversification of cell signaling phenotypes by modular domain recombination. Science (New York, N.Y.) 328, 368-372 (2010).
32. W. M. Shaw et al., Engineering a Model Cell for Rational Tuning of GPCR Signaling. Cell 177, 782-796.e727 (2019).
33. S. G. Peisajovich, D. S. Tawfik, Protein engineers turned evolutionists. Nature methods 4, 991-994 (2007).
34. C. J. Bashor, A. A. Horwitz, S. G. Peisajovich, W. A. Lim, Rewiring cells: synthetic biology as a tool to interrogate the organizational principles of living systems. Annual review of biophysics 39, 515-537 (2010).
35. F. Di Virgilio, P. Pinton, S. Falzoni, Assessing Extracellular ATP as Danger Signal In Vivo: The pmeLuc System. Methods Mol Biol 1417, 115-129 (2016).
36. R. B. Di Roberto, B. Chang, A. Trusina, S. G. Peisajovich, Evolution of a G protein-coupled receptor response by mutations in regulatory network interactions. Nature communications 7, 12344 (2016).
37. J. A. Ballesteros, H. Weinstein, in Methods in Neurosciences, C. S. Stuart, Ed. (Academic Press, 1995), vol. Volume 25, pp. 366-428.
38. M. Rafehi et al., Molecular Recognition of Agonists and Antagonists by the Nucleotide-Activated G Protein-Coupled P2Y2 Receptor. J Med Chem 60, 8425-8440 (2017).
39. P. Hillmann et al., Key determinants of nucleotide-activated G protein-coupled P2Y (2) receptor function revealed by chemical and pharmacological experiments, mutagenesis and homology modeling. J Med Chem 52, 2762-2775 (2009).
40. M. Schutz et al., Directed evolution of G protein-coupled receptors in yeast for higher functional production in eukaryotic expression hosts. Sci Rep 6, 21508 (2016).
41. F. Magnani, Y. Shibata, M. J. Serrano-Vega, C. G. Tate, Co-evolving stability and conformational homogeneity of the human adenosine A2a receptor. Proc Natl Acad Sci USA 105, 10744-10749 (2008).
42. F. M. Heydenreich, Z. Vuckovic, M. Matkovic, D. B. Veprintsev, Stabilization of G protein-coupled receptors by point mutations. Front Pharmacol 6, 82 (2015).
43. S. Montaner, I. Kufareva, R. Abagyan, J. S. Gutkind, Molecular mechanisms deployed by virally encoded G protein-coupled receptors in human diseases. Annu Rev Pharmacol Toxicol 53, 331-354 (2013).
44. B. G. Tehan, A. Bortolato, F. E. Blaney, M. P. Weir, J. S. Mason, Unifying family A GPCR theories of activation. Pharmacol Ther 143, 51-60 (2014).
45. P. Schmidt et al., Identification of determinants required for agonistic and inverse agonistic ligand properties at the ADP receptor P2Y12. Mol Pharmacol 83, 256-266 (2013).
46. R. Nygaard, T. M. Frimurer, B. Holst, M. M. Rosenkilde, T. W. Schwartz, Ligand binding and micro-switches in 7™ receptor structures. Trends Pharmacol Sci 30, 249-259 (2009).
47. A. J. Venkatakrishnan et al., Diverse activation pathways in class A GPCRs converge near the G-protein-coupling region. Nature 536, 484-487 (2016).
48. P. Wan et al., Extracellular ATP mediates inflammatory responses in colitis via P2×7 receptor signaling. Sci Rep 6, 19108 (2016).
49. M. A. Komoszynski, Comparative studies on animal and plant apyrases (ATP diphosphohydrolase EC 3.6.1.5) with application of immunological techniques and various ATPase inhibitors. Comp Biochem Physiol B Biochem Mol Biol 113, 581-591 (1996).
50. N. Nourizad, M. Ehn, B. Gharizadeh, S. Hober, P. Nyren, Methylotrophic yeast *Pichia pastoris* as a host for production of ATP-diphosphohydrolase (apyrase) from potato tubers (*Solanum tuberosum*). Protein expression and purification 27, 229-237 (2003).
51. J. A. Goettel et al., AHR Activation Is Protective against Colitis Driven by T Cells in Humanized Mice. Cell reports 17, 1318-1329 (2016).
52. R. Nowarski, R. Jackson, R. A. Flavell, The Stromal Intervention: Regulation of Immunity and Inflammation at the Epithelial-Mesenchymal Barrier. Cell 168, 362-375 (2017).

53. P. P. Trivedi, G. B. Jena, Dextran sulfate sodium-induced ulcerative colitis leads to increased hematopoiesis and induces both local as well as systemic genotoxicity in mice. Mutat Res 744, 172-183 (2012).
54. G. F. Sonnenberg, L. A. Fouser, D. Artis, Border patrol: regulation of immunity, inflammation and tissue homeostasis at barrier surfaces by IL-22. Nature immunology 12, 383-390 (2011).
55. A. Yeste et al., IL-21 induces IL-22 production in CD4+ T cells. Nature communications 5, 3753 (2014).
56. S. Fichtner-Feigl et al., Induction of IL-13 triggers TGF-beta1-dependent tissue fibrosis in chronic 2,4,6-trinitrobenzene sulfonic acid colitis. J Immunol 178, 5859-5870 (2007).
57. I. C. Lawrance et al., A murine model of chronic inflammation-induced intestinal fibrosis down-regulated by antisense NF-kappa B. Gastroenterology 125, 1750-1761 (2003).
58. S. Speca, I. Giusti, F. Rieder, G. Latella, Cellular and molecular mechanisms of intestinal fibrosis. World J Gastroenterol 18, 3635-3661 (2012).
59. Q. He et al., Dysbiosis of the fecal microbiota in the TNBS-induced Crohn's disease mouse model. Appl Microbiol Biotechnol 100, 4485-4494 (2016).
60. I. Lagkouvardos et al., The Mouse Intestinal Bacterial Collection (miBC) provides host-specific insight into cultured diversity and functional potential of the gut microbiota. Nat Microbiol 1, 16131 (2016).
61. A. R. Rogala, A. Oka, R. B. Sartor, Strategies to Dissect Host-Microbial Immune Interactions That Determine Mucosal Homeostasis vs. Intestinal Inflammation in Gnotobiotic Mice. Frontiers in immunology 11, 214 (2020).
62. D. N. Frank et al., Molecular-phylogenetic characterization of microbial community imbalances in human inflammatory bowel diseases. Proc Natl Acad Sci USA 104, 13780-13785 (2007).
63. D. Gevers et al., The treatment-naive microbiome in new-onset Crohn's disease. Cell Host Microbe 15, 382-392 (2014).
64. A. E. Reeves, M. J. Koenigsknecht, I. L. Bergin, V. B. Young, Suppression of *Clostridium difficile* in the gastrointestinal tracts of germfree mice inoculated with a murine isolate from the family Lachnospiraceae. Infect Immun 80, 3786-3794 (2012).
65. K. Machiels et al., A decrease of the butyrate-producing species *Roseburia hominis* and *Faecalibacterium prausnitzii* defines dysbiosis in patients with ulcerative colitis. Gut 63, 1275-1283 (2014).
66. C. Zhu et al., *Roseburia intestinalis* inhibits interleukin17 excretion and promotes regulatory T cells differentiation in colitis. Mol Med Rep 17, 7567-7574 (2018).
67. L. M. Proctor et al., The Integrative Human Microbiome Project. Nature 569, 641-648 (2019).
68 D. J. Friedman et al., From the Cover: CD39 deletion exacerbates experimental murine colitis and human polymorphisms increase susceptibility to inflammatory bowel disease. Proc Natl Acad Sci USA 106, 16788-16793 (2009).
69. S. Deaglio et al., Adenosine generation catalyzed by CD39 and CD73 expressed on regulatory T cells mediates immune suppression. The Journal of experimental medicine 204, 1257-1265 (2007).
70. D. J. Gibson et al., Heightened Expression of CD39 by Regulatory T Lymphocytes Is Associated with Therapeutic Remission in Inflammatory Bowel Disease. Inflamm Bowel Dis 21, 2806-2814 (2015).
71. I. D. Mascanfroni et al., IL-27 acts on DCs to suppress the T cell response and autoimmunity by inducing expression of the immunoregulatory molecule CD39. Nature immunology 14, 1054-1063 (2013).
72. W. G. Junger, Immune cell regulation by autocrine purinergic signalling. Nat Rev Immunol 11, 201-212 (2011).
73. U. Schenk et al., ATP inhibits the generation and function of regulatory T cells through the activation of purinergic P2X receptors. Science signaling 4, ra12 (2011).
74. M. Proietti et al., ATP released by intestinal bacteria limits the generation of protective IgA against enteropathogens. Nature communications 10, 250 (2019).
75. G. P. Donaldson et al., Gut microbiota utilize immunoglobulin A for mucosal colonization. Science (New York, N.Y.) 360, 795-800 (2018).
76. J. Grootjans et al., Epithelial endoplasmic reticulum stress orchestrates a protective IgA response. Science (New York, N.Y.) 363, 993-998 (2019).
77. M. C. Takenaka et al., Control of tumor-associated macrophages and T cells in glioblastoma via AHR and CD39. Nature neuroscience 22, 729-740 (2019).
78. P. M. Sato, K. Yoganathan, J. H. Jung, S. G. Peisajovich, The robustness of a signaling complex to domain rearrangements facilitates network evolution. PLOS biology 12, e1002012 (2014).
79. P. Wei et al., Bacterial virulence proteins as tools to rewire kinase pathways in yeast and immune cells. Nature 488, 384-388 (2012).
80. H. Braat et al., A phase I trial with transgenic bacteria expressing interleukin-10 in Crohn's disease. Clin Gastroenterol Hepatol 4, 754-759 (2006).
81. R. Mckay et al., A platform of genetically engineered bacteria as vehicles for localized delivery of therapeutics: Toward applications for Crohn's disease. Bioeng Transl Med 3, 209-221 (2018).
82. A. K. Nash et al., The gut mycobiome of the Human Microbiome Project healthy cohort. Microbiome 5, 153 (2017).
83. H. Sokol et al., Fungal microbiota dysbiosis in IBD. Gut 66, 1039-1048 (2017).
84. F. Strati et al., Age and Gender Affect the Composition of Fungal Population of the Human Gastrointestinal Tract. Front Microbiol 7, 1227 (2016).
85. R. Enaud et al., The Mycobiome: A Neglected Component in the Microbiota-Gut-Brain Axis. Microorganisms 6, (2018).
86. F. S. Martins et al., Oral treatment with *Saccharomyces cerevisiae* strain
UFMG 905 modulates immune responses and interferes with signal pathways involved in the activation of inflammation in a murine model of typhoid fever. Int J Med Microbiol 301, 359-364 (2011).
87. L. Rizzetto et al., Fungal Chitin Induces Trained Immunity in Human Monocytes during Cross-talk of the Host with *Saccharomyces cerevisiae*. J Biol Chem 291, 7961-7972 (2016).
88. G. Zanello et al., *Saccharomyces cerevisiae* modulates immune gene expressions and inhibits ETEC-mediated ERK1/2 and p38 signaling pathways in intestinal epithelial cells. PLOS One 6, e18573 (2011).
89. M. L. Palma et al., Probiotic *Saccharomyces cerevisiae* strains as biotherapeutic tools: is there room for improvement? Appl Microbiol Biotechnol 99, 6563-6570 (2015).

90. S. Sen, T. J. Mansell, Yeasts as probiotics: Mechanisms, outcomes, and future potential. Fungal Genet Biol 137, 103333 (2020).
91. D. Durmusoglu, I. Al'Abri, S. P. Collins, C. Beisel, N. Crook, Establishing Probiotic <em>*Saccharomyces boulardii*</em> as a Model Organism for Synthesis and Delivery of Biomolecules. bioRxiv, 2020.2001.2022.915389 (2020).
92. L. E. Hudson et al., Functional heterologous protein expression by genetically engineered probiotic yeast *Saccharomyces boulardii*. PLOS One 9, e112660 (2014).
93. N. Takemura et al., Eosinophil depletion suppresses radiation-induced small intestinal fibrosis. Science translational medicine 10, (2018).
94. K. Wilhelm et al., Graft-versus-host disease is enhanced by extracellular ATP activating P2X7R. Nat Med 16, 1434-1438 (2010).
95. K. Berer et al., Commensal microbiota and myelin autoantigen cooperate to trigger autoimmune demyelination. Nature 479, 538-541 (2011).
96. V. Rothhammer et al., Microglial control of astrocytes in response to microbial metabolites. Nature 557, 724-728 (2018).
97. V. Rothhammer et al., Type I interferons and microbial metabolites of tryptophan modulate astrocyte activity and central nervous system inflammation via the aryl hydrocarbon receptor. Nat Med 22, 586-597 (2016).
98. C. J. Bashor, N. C. Helman, S. Yan, W. A. Lim, Using engineered scaffold interactions to reshape MAP kinase pathway signaling dynamics. Science 319, 1539-1543 (2008).
99. B. M. Scott et al., Coupling of Human Rhodopsin to a Yeast Signaling Pathway Enables Characterization of Mutations Associated with Retinal Disease. Genetics 211, 597-615 (2019).
100. S. Keppler-Ross, C. Noffz, N. Dean, A new purple fluorescent color marker for genetic studies in *Saccharomyces cerevisiae* and *Candida albicans*. Genetics 179, 705-710 (2008).
101. M. E. Lee, W. C. DeLoache, B. Cervantes, J. E. Dueber, A Highly Characterized Yeast Toolkit for Modular, Multipart Assembly. ACS Synth Biol 4, 975-986 (2015).
102. W. M. Shaw et al., Engineering a Model Cell for Rational Tuning of GPCR Signaling. Cell 177, 782-796.e727 (2019).
103. F. Moser, A. Horwitz, J. Chen, W. Lim, C. A. Voigt, Genetic sensor for strong methylating compounds. ACS Synth Biol 2, 614-624 (2013).
104. R. B. Di Roberto, B. M. Scott, S. G. Peisajovich, Directed Evolution Methods to Rewire Signaling Networks. Methods Mol Biol 1596, 321-337 (2017).
105. S. Dong, S. C. Rogan, B. L. Roth, Directed molecular evolution of DREADDs: a generic approach to creating next-generation RASSLs. Nature protocols 5, 561-573 (2010).
106. R. B. Di Roberto, B. Chang, A. Trusina, S. G. Peisajovich, Evolution of a G protein-coupled receptor response by mutations in regulatory network interactions. Nature communications 7, 12344 (2016).
107. M. Rafehi et al., Molecular Recognition of Agonists and Antagonists by the Nucleotide-Activated G Protein-Coupled P2Y2 Receptor. J Med Chem 60, 8425-8440 (2017).
108. B. Webb, A. Sali, Comparative Protein Structure Modeling Using MODELLER. Curr Protoc Bioinformatics 47, 5 6 1-32 (2014).
109. M. Wiederstein, M. J. Sippl, ProSA-web: interactive web service for the recognition of errors in three-dimensional structures of proteins. Nucleic Acids Res 35, W407-410 (2007).
110. S. C. Lovell et al., Structure validation by Calpha geometry: phi,psi and Cbeta deviation. Proteins 50, 437-450 (2003).
111. G. R. Lee, C. Seok, Galaxy7TM: flexible GPCR-ligand docking by structure refinement. Nucleic Acids Res 44, W502-506 (2016).
112. O. W. Ryan et al., Selection of chromosomal DNA libraries using a multiplex CRISPR system. Elife 3, (2014).
113. S. V. Prykhozhij, V. Rajan, D. Gaston, J. N. Berman, CRISPR multitargeter: a web tool to find common and unique CRISPR single guide RNA targets in a set of similar sequences. PLOS One 10, e0119372 (2015).
114. V. Pliatsika, I. Rigoutsos, "Off-Spotter": very fast and exhaustive enumeration of genomic lookalikes for designing CRISPR/Cas guide RNAs. Biol Direct 10, 4 (2015).
115. A. F. Knowles, The GDA1_CD39 superfamily: NTPDases with diverse functions. Purinergic signalling 7, 21-45 (2011).
116. R. K. Schott, D. Gow, B. S. Chang, BlastPhyMe: A toolkit for rapid generation and analysis of protein-coding sequence datasets. bioRxiv, (2016).
117. M. A. Komoszynski, Comparative studies on animal and plant apyrases (ATP diphosphohydrolase EC 3.6.1.5) with application of immunological techniques and various ATPase inhibitors. Comp Biochem Physiol B Biochem Mol Biol 113, 581-591 (1996).
118. J. R. Veloria, A. K. Devkota, E. J. Cho, K. N. Dalby, Optimization of a Luminescence-Based High-Throughput Screening Assay for Detecting Apyrase Activity. SLAS Discov 22, 94-101 (2017).
119. L. M. Cox et al., Calorie restriction slows age-related microbiota changes in an Alzheimer's disease model in female mice. Sci Rep 9, 17904 (2019).
120. J. G. Caporaso et al., QIIME allows analysis of high-throughput community sequencing data. Nature methods 7, 335-336 (2010).
121. C. Lozupone, M. E. Lladser, D. Knights, J. Stombaugh, R. Knight, UniFrac: an effective distance metric for microbial community comparison. ISME J 5, 169-172 (2011).
122. N. Segata et al., Metagenomic biomarker discovery and explanation. Genome Biol 12, R60 (2011).
123. S. Babicki et al., Heatmapper: web-enabled heat mapping for all. Nucleic Acids Res 44, W147-153 (2016).
124. M. V. Kuleshov et al., Enrichr: a comprehensive gene set enrichment analysis web server 2016 update. Nucleic Acids Res 44, W90-97 (2016).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated *Saccharomyces* cell, that has been engineered to express:

(i) a mammalian P2Y purinoceptor 2 (P2Y2) protein;

(ii) a mutant Gpa1 protein comprising at least 5 C-terminal residues from a mammalian G alpha, wherein the mutant Gpa1 protein couples the P2Y2 protein to the yeast mating pathway; and (iii) an anti-inflammatory protein, wherein the anti-inflammatory protein is expressed under the control of a promoter activated downstream of P2Y2 activation, the isolated *Saccharomyces* cell secretes the anti-inflammatory protein in the presence of extracellular adenosine triphosphate (eATP), and the anti-inflammatory protein comprises apyrase, interleukin 10 (IL-10), IL-2, IL-27, IL-22, or IFN-beta, and wherein the P2Y2 comprises one or more mutations relative to SEQ ID NO: 13 that increase expression of the anti-inflammatory protein, wherein the mutations are: in residues peripheral to a ligand binding pocket, wherein the mutations are in $A76^{2.47}$, $N116^{3.35}$, $C119^{3.38}$, $L162^{4.54}$, and/or $Q165^{4.57}$; and/or in residues in the intracellular facing side of the receptor, wherein the mutations are in $F58^{1.57}$, $L59^{1.58}$, $C60^{1.59}$, $A229^{ICL3}$, $K240^{6.31}$, $F307^{7.54}$, and/or $G310^{C\text{-}term}$.

2. The isolated *Saccharomyces* cell of claim 1, which has been engineered to reduce or remove expression of one or more endogenous proteins selected from the group consisting of:

(i) yeast GPCR alpha-factor pheromone receptor STE2;

(ii) negative regulator of pathway function GTPase-activating protein SST2;

(iii) cell cycle regulator cyclin-dependent protein serine/threonine kinase inhibiting protein FAR1; and (iv) yeast G alpha protein guanine nucleotide-binding protein subunit alpha GPA1.

3. The isolated *Saccharomyces* cell of claim 1, wherein the anti-inflammatory protein comprises a yeast-derived leader peptide that directs the protein to be secreted.

4. The isolated *Saccharomyces* cell of claim 3, wherein the yeast-derived leader peptide lacks any signal or leader sequence endogenous to the anti-inflammatory protein.

5. The isolated *Saccharomyces* cell of claim 1, wherein at least one of the P2Y2 protein, mutant Gpa1, or anti-inflammatory protein are expressed from sequences codon-optimized for expression in the *Saccharomyces* cell.

6. The isolated *Saccharomyces* cell of claim 1, wherein the one or more mutations relative to SEQ ID NO:13 comprise F58C, Q165H, F307S, and/or N116S.

7. The isolated *Saccharomyces* cell of claim 1, wherein the one or more mutations relative to SEQ ID NO: 13 comprise N116S.

8. The isolated *Saccharomyces* cell of claim 7, wherein the mutations relative to SEQ ID NO: 13 comprise mutations N116S in combination with mutations F58I or F307S.

9. The isolated *Saccharomyces* cell of claim 1, wherein the P2Y2 comprises mutations relative to SEQ ID NO: 13 at L59 and/or C119.

10. The isolated *Saccharomyces* cell of claim 9, wherein the mutations relative to SEQ ID NO: 13 are L591 and/or C119S.

11. The isolated *Saccharomyces* cell of claim 1, wherein the promoter activated downstream of P2Y2 activation is a mating-responsive promoter.

12. The isolated *Saccharomyces* cell of claim 11, wherein the mating-responsive promoter is pFUS1 or pFIG1.

13. The isolated *Saccharomyces* cell of claim 1, wherein the expression of the anti-inflammatory protein is driven by a synthetic transcription factor comprising a pheromone responsive domain and a DNA binding domain, binding to non-yeast DNA operator sequences upstream of the sequence encoding the anti-inflammatory protein.

14. A composition comprising the isolated *Saccharomyces* cell of claim 1, and a physiologically-acceptable carrier.

15. The composition of claim 14, which is a solid or liquid form for oral administration.

16. The composition of claim 15, wherein the solid or liquid form for oral administration comprises tablets, pills, capsules, soft gelatin capsules, sugarcoated pills, orodispersing tablets, effervescent tablets, or a drinkable solution.

17. The composition of claim 14, wherein the composition is a nutritional composition.

18. The composition of claim 17, wherein the nutritional composition is selected from beverages, breakfast cereal, spreads, meal replacements, confectionary, chocolate, gels, ice creams, cereal, fruit, chocolate bars, energy bars, snack bars, food bars, sauces, dips, and sports supplements including dairy and non-dairy based sports supplements.

19. The composition of claim 18, wherein the beverages comprise smoothies or cultured beverages, flavored beverages, yogurt, drinking yogurt, set yogurt, fruit and/or vegetable juices or concentrates thereof, fruit and vegetable juice powders, reconstituted fruit products, powders, malt or soy or cereal based beverages.

20. The composition of claim 18, wherein the breakfast cereal is muesli flakes.

21. The isolated *Saccharomyces* cell of claim 1, wherein the *Saccharomyces* cell is *S. cerevisiae* or *S. boulardii.*

22. The isolated *Saccharomyces* cell of claim 1, wherein the P2Y2 protein is human P2Y2.

23. The isolated *Saccharomyces* cell of claim 1, wherein the mammalian G alpha is $G\alpha_{i3}$.

24. The isolated *Saccharomyces* cell of claim 1, wherein the anti-inflammatory protein is a mammalian anti-inflammatory protein.

25. The isolated *Saccharomyces* cell of claim 24, wherein the anti-inflammatory protein is a human anti-inflammatory protein.

26. An engineered mammalian P2Y purinoceptor 2 (P2Y2) protein comprising one or more mutations relative to SEQ ID NO:13, wherein the mutations are:

in residues peripheral to a ligand binding pocket, wherein the mutations are in $A76^{2.47}$, $N116^{3.35}$, $C119^{3.38}$, $L162^{4.54}$, $Q165^{4.57}$, or a combination thereof; and/or in residues in the intracellular facing side of the receptor (optionally, wherein the mutations are in $F58^{1.57}$, $L59^{1.58}$, $C60^{1.59}$, $A229^{ICL3}$, $K240^{6.31}$, $F307^{7.54}$, $G310^{C\text{-}term}$, or a combination thereof.

27. The engineered mammalian P2Y2 of claim 26, wherein the one or more mutations relative to SEQ ID NO:13 comprise F58C, Q165H, F307S, and/or N116S.

28. An isolated nucleic acid sequence encoding the engineered mammalian P2Y2 of claim 26.

29. A host cell comprising the isolated nucleic acid sequence of claim 28, and expressing the engineered mammalian P2Y2.

30. The host cell of claim 29, wherein the cell is a *Saccharomyces* cell, and the isolated nucleic acid sequence is codon-optimized for expression in the *Saccharomyces* cell.

* * * * *

SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence
<220> FEATURE:
<223> OTHER INFORMATION: HygB g1143 gRNA

<400> SEQUENCE: 1
acaaatcgcc cgcagaagcg 20

<210> SEQ ID NO 2
<211> LENGTH: 30
<212> TYPE: DNA
<213> ORGANISM: Artificial Sequence
<220> FEATURE:
<223> OTHER INFORMATION: HygB g1143 target

<400> SEQUENCE: 2
gtacacaaat cgcccgcaga agcgcggccg 30

<210> SEQ ID NO 3
<211> LENGTH: 20
<212> TYPE: DNA
<213> ORGANISM: Artificial Sequence
<220> FEATURE:
<223> OTHER INFORMATION: mCherry g664 gRNA

<400> SEQUENCE: 3
gctgaaggta gacattcaac 20

<210> SEQ ID NO 4
<211> LENGTH: 30
<212> TYPE: DNA
<213> ORGANISM: Artificial Sequence
<220> FEATURE:
<223> OTHER INFORMATION: mCherry g664 target

<400> SEQUENCE: 4
aagagctgaa ggtagacatt caactggtgg 30

<210> SEQ ID NO 5
<211> LENGTH: 1557
<212> TYPE: DNA
<213> ORGANISM: Artificial Sequence
<220> FEATURE:
<223> OTHER INFORMATION: RROP1: codon optimized with secretion signal and HA tag

<400> SEQUENCE: 5
atgagattcc catcaatctt caccgcagtt cttttcgcag cctcttccgc actcgcagcc 60
cctgtgaata caacaacaga agatgaaact gctcaaatcc cagctgaagc agtcattggc 120
tacttagatt tggaggggga tttcgatgtt gcagttctac ctttctcaaa ttcaacaaac 180
aatggattgc tgttcataaa cactaccatc gctagcattg cagctaagga ggagggtgtg 240
tcattagata agagacaaat tccattacgt cgacatctgt taagtcatga atctgaacac 300
tacgcggtta tcttcgatgc agggtctaca ggttcaagag tacatgtttt tcgtttcgac 360
gaaaagttag gcttacttcc tattggaaat aacatagaat acttcatggc cacagagcca 420
ggtttaagta gctacgccga agatccaaaa gctgcagcta actctttaga accattattg 480
gatggtgcgg aaggagttgt gccacaggaa ctacaatcag agacaccatt ggaacttggc 540

```
gctacagccg gtttgagaat gctaaaaggg gacgccgctg agaagattct ccaggcagtg    600

agaaacttag tgaaaaacca atcaacattc cattccaagg atcaatgggt gacaatctta    660

gatggtacac aagagggctc ttacatgtgg gcagcaatta actatctatt gggcaatctt    720

gggaaagatt acaagtctac cacagctaca atcgacctag gcggaggttc cgtacaaatg    780

gcttacgcta ttagtaacga acaatttgcg aaggcaccac aaaacgagga cggagagcca    840

tacgttcaac aaaagcactt gatgtctaag gattacaact tatacgtcca ttcatacttg    900

aactatggtc aactggctgg gagagcagaa atctttaaag catctagaaa cgaaagtaac    960

ccttgtgctt tggaaggttg tgacggttat tactcatacg gtggcgtcga ttacaaggtt   1020

aaggctccta aaaagggttc atcttggaag agatgtagaa gattgactag acacgctcta   1080

aagatcaatg caaaatgcaa tattgaggaa tgcactttca atggcgtttg gaatggtggg   1140

ggtggagatg gacagaaaaa cattcacgca tcctctttct tttacgatat tggtgctcag   1200

gtcggtattg ttgatacaaa gtttccatca gctctagcaa agccaattca atacttaaat   1260

gccgcaaagg tcgcctgcca aactaacgta gcggacatta agagcatatt ccctaaaact   1320

caagatagaa atatcccata tttgtgtatg gacctcattt acgaatacac ccttcttgta   1380

gatggtttcg gcctaaaccc tcataaggaa ataactgtta tccatgacgt tcagtacaaa   1440

aactacttgg tcggagctgc ctggccactg ggttgtgcta tagatctcgt gtcctctact   1500

acaaacaaga tacgcgttgc atcttcttac ccttacgatg tcccagatta cgcctga      1557
```

<210> SEQ ID NO 6
<211> LENGTH: 518
<212> TYPE: PRT
<213> ORGANISM: Artificial Sequence
<220> FEATURE:
<223> OTHER INFORMATION: RROP1: codon optimized with secretion signal and HAtag

<400> SEQUENCE: 6

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Gln Ile Pro Leu Arg Arg His Leu Leu Ser His
                85                  90                  95

Glu Ser Glu His Tyr Ala Val Ile Phe Asp Ala Gly Ser Thr Gly Ser
            100                 105                 110

Arg Val His Val Phe Arg Phe Asp Glu Lys Leu Gly Leu Leu Pro Ile
        115                 120                 125

Gly Asn Asn Ile Glu Tyr Phe Met Ala Thr Glu Pro Gly Leu Ser Ser
    130                 135                 140

Tyr Ala Glu Asp Pro Lys Ala Ala Ala Asn Ser Leu Glu Pro Leu Leu
145                 150                 155                 160

Asp Gly Ala Glu Gly Val Val Pro Gln Glu Leu Gln Ser Glu Thr Pro
                165                 170                 175

Leu Glu Leu Gly Ala Thr Ala Gly Leu Arg Met Leu Lys Gly Asp Ala
```

```
        180                 185                 190

Ala Glu Lys Ile Leu Gln Ala Val Arg Asn Leu Val Lys Asn Gln Ser
        195                 200                 205

Thr Phe His Ser Lys Asp Gln Trp Val Thr Ile Leu Asp Gly Thr Gln
    210                 215                 220

Glu Gly Ser Tyr Met Trp Ala Ala Ile Asn Tyr Leu Leu Gly Asn Leu
225                 230                 235                 240

Gly Lys Asp Tyr Lys Ser Thr Thr Ala Thr Ile Asp Leu Gly Gly Gly
                245                 250                 255

Ser Val Gln Met Ala Tyr Ala Ile Ser Asn Glu Gln Phe Ala Lys Ala
            260                 265                 270

Pro Gln Asn Glu Asp Gly Glu Pro Tyr Val Gln Gln Lys His Leu Met
        275                 280                 285

Ser Lys Asp Tyr Asn Leu Tyr Val His Ser Tyr Leu Asn Tyr Gly Gln
    290                 295                 300

Leu Ala Gly Arg Ala Glu Ile Phe Lys Ala Ser Arg Asn Glu Ser Asn
305                 310                 315                 320

Pro Cys Ala Leu Glu Gly Cys Asp Gly Tyr Tyr Ser Tyr Gly Gly Val
                325                 330                 335

Asp Tyr Lys Val Lys Ala Pro Lys Lys Gly Ser Ser Trp Lys Arg Cys
            340                 345                 350

Arg Arg Leu Thr Arg His Ala Leu Lys Ile Asn Ala Lys Cys Asn Ile
        355                 360                 365

Glu Glu Cys Thr Phe Asn Gly Val Trp Asn Gly Gly Gly Gly Asp Gly
    370                 375                 380

Gln Lys Asn Ile His Ala Ser Ser Phe Phe Tyr Asp Ile Gly Ala Gln
385                 390                 395                 400

Val Gly Ile Val Asp Thr Lys Phe Pro Ser Ala Leu Ala Lys Pro Ile
                405                 410                 415

Gln Tyr Leu Asn Ala Ala Lys Val Ala Cys Gln Thr Asn Val Ala Asp
            420                 425                 430

Ile Lys Ser Ile Phe Pro Lys Thr Gln Asp Arg Asn Ile Pro Tyr Leu
        435                 440                 445

Cys Met Asp Leu Ile Tyr Glu Tyr Thr Leu Leu Val Asp Gly Phe Gly
    450                 455                 460

Leu Asn Pro His Lys Glu Ile Thr Val Ile His Asp Val Gln Tyr Lys
465                 470                 475                 480

Asn Tyr Leu Val Gly Ala Ala Trp Pro Leu Gly Cys Ala Ile Asp Leu
                485                 490                 495

Val Ser Ser Thr Thr Asn Lys Ile Arg Val Ala Ser Ser Tyr Pro Tyr
            500                 505                 510

Asp Val Pro Asp Tyr Ala
        515


<210> SEQ ID NO 7
<211> LENGTH: 1539
<212> TYPE: DNA
<213> ORGANISM: Artificial Sequence
<220> FEATURE:
<223> OTHER INFORMATION: TUAP1: codon optimized with secretion signal
      and HAtag

<400> SEQUENCE: 7

atgagattcc catcaatctt caccgcagtt cttttcgcag cctcttccgc actcgcagcc      60

cctgtgaata caacaacaga agatgaaact gctcaaatcc cagctgaagc agtcattggc     120
```

```
tacttagatt tggaggggga tttcgatgtt gcagttctac ctttctcaaa ttcaacaaac    180

aatggattgc tgttcataaa cactaccatc gctagcattg cagctaagga ggagggtgtg    240

tcattagata agagagccga aatcgctcag gcccgggcag cggcagttcc tccagtcggt    300

aagtatgccg tcattttaga cgctggtagt acaggtacac gtatgcatgt ttttagattt    360

gacaagagaa tggacttagt aaagataggg gatgatatag aagtgtttgc aaaggtcaac    420

ccaggtttga gctcatactc tggtcgtcca aaggaagcta ccgagtccat tttaccattg    480

ttacaaaagg ctaactctgt agtacctcaa agattgatga aaaccacccc tgtaaagctt    540

ggcgctacag ccggtttgag attgataggg gataaacaag ctaagcaaat cctcgacgcg    600

gttagaggcg ctgtacacac aaacactaag tttcaataca accctaaatg gattaacgtt    660

cttgagggtt ctcaggaagg ttcctacctt tgggtagctc ttaactatct attggataat    720

ctggggggag attactctaa gacagtcgga gttattgact taggcggtgg aagtgttcaa    780

atggcctatg ctatttcccc agccactgtg gttgccgcac caggtgttcc acatggaaaa    840

gatccttacg ttacaaagga atacttaaaa ggtagagatt acaacatcta cgtccactca    900

tacttgagat atggagcgct ggcttccaga gttgaaatct ttaaagcaaa ggaaggccca    960

ttctcttact gtatgttgag aggcttcagt ggtaagtaca cttacaatgg tgaagagtac   1020

aacgctacag catctactgg tggtgcacaa tacggtaaat gcagaggtga tgtaatgaag   1080

gcccttaaac tagatgcccc atgccaagcg aaaaagtgta cttttgatgg tgtctggaat   1140

ggaggtggag gtccagggca agcaaacttg tacgtcgctt ctagtttcta ctatatggct   1200

tctcaggttg gtctaatcga ctcagatgct ccatcaggaa catctacacc aatggctttc   1260

agagccgtcg cacagaaaat ctgtagaatg tctctgaagg aagttaaggc aaagtaccct   1320

aaggttagag atatccctta catttgcatg gatctagtgt atcaatactc attgttagtt   1380

gacggctttg gtttagaacc tactaaaaac attaccctcg ttgaaaaggt taaacatggc   1440

gagtacttca ttgaagcagc ttggccattg ggcgaagcaa ttgaggcagt ggcgccgaaa   1500

aaggggactt acccatacga cgtgccagat tacgcctag                          1539
```

<210> SEQ ID NO 8
<211> LENGTH: 512
<212> TYPE: PRT
<213> ORGANISM: Artificial Sequence
<220> FEATURE:
<223> OTHER INFORMATION: TUAP1: codon optimized with secretion signal and HAtag

<400> SEQUENCE: 8

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Ala Glu Ile Ala Gln Ala Arg Ala Ala Ala Val
                85                  90                  95

Pro Pro Val Gly Lys Tyr Ala Val Ile Leu Asp Ala Gly Ser Thr Gly
```

```
            100                 105                 110

Thr Arg Met His Val Phe Arg Phe Asp Lys Arg Met Asp Leu Val Lys
        115                 120                 125

Ile Gly Asp Asp Ile Glu Val Phe Ala Lys Val Asn Pro Gly Leu Ser
    130                 135                 140

Ser Tyr Ser Gly Arg Pro Lys Glu Ala Thr Glu Ser Ile Leu Pro Leu
145                 150                 155                 160

Leu Gln Lys Ala Asn Ser Val Val Pro Gln Arg Leu Met Lys Thr Thr
                165                 170                 175

Pro Val Lys Leu Gly Ala Thr Ala Gly Leu Arg Leu Ile Gly Asp Lys
            180                 185                 190

Gln Ala Lys Gln Ile Leu Asp Ala Val Arg Gly Ala Val His Thr Asn
        195                 200                 205

Thr Lys Phe Gln Tyr Asn Pro Lys Trp Ile Asn Val Leu Glu Gly Ser
    210                 215                 220

Gln Glu Gly Ser Tyr Leu Trp Val Ala Leu Asn Tyr Leu Leu Asp Asn
225                 230                 235                 240

Leu Gly Gly Asp Tyr Ser Lys Thr Val Gly Val Ile Asp Leu Gly Gly
                245                 250                 255

Gly Ser Val Gln Met Ala Tyr Ala Ile Ser Pro Ala Thr Val Val Ala
            260                 265                 270

Ala Pro Gly Val Pro His Gly Lys Asp Pro Tyr Val Thr Lys Glu Tyr
        275                 280                 285

Leu Lys Gly Arg Asp Tyr Asn Ile Tyr Val His Ser Tyr Leu Arg Tyr
    290                 295                 300

Gly Ala Leu Ala Ser Arg Val Glu Ile Phe Lys Ala Lys Glu Gly Pro
305                 310                 315                 320

Phe Ser Tyr Cys Met Leu Arg Gly Phe Ser Gly Lys Tyr Thr Tyr Asn
                325                 330                 335

Gly Glu Glu Tyr Asn Ala Thr Ala Ser Thr Gly Gly Ala Gln Tyr Gly
            340                 345                 350

Lys Cys Arg Gly Asp Val Met Lys Ala Leu Lys Leu Asp Ala Pro Cys
        355                 360                 365

Gln Ala Lys Lys Cys Thr Phe Asp Gly Val Trp Asn Gly Gly Gly Gly
    370                 375                 380

Pro Gly Gln Ala Asn Leu Tyr Val Ala Ser Ser Phe Tyr Tyr Met Ala
385                 390                 395                 400

Ser Gln Val Gly Leu Ile Asp Ser Asp Ala Pro Ser Gly Thr Ser Thr
                405                 410                 415

Pro Met Ala Phe Arg Ala Val Ala Gln Lys Ile Cys Arg Met Ser Leu
            420                 425                 430

Lys Glu Val Lys Ala Lys Tyr Pro Lys Val Arg Asp Ile Pro Tyr Ile
        435                 440                 445

Cys Met Asp Leu Val Tyr Gln Tyr Ser Leu Leu Val Asp Gly Phe Gly
    450                 455                 460

Leu Glu Pro Thr Lys Asn Ile Thr Leu Val Glu Lys Val Lys His Gly
465                 470                 475                 480

Glu Tyr Phe Ile Glu Ala Ala Trp Pro Leu Gly Glu Ala Ile Glu Ala
                485                 490                 495

Val Ala Pro Lys Lys Gly Thr Tyr Pro Tyr Asp Val Pro Asp Tyr Ala
            500                 505                 510
```

<210> SEQ ID NO 9

<211> LENGTH: 1419
<212> TYPE: DNA
<213> ORGANISM: Artificial Sequence
<220> FEATURE:
<223> OTHER INFORMATION: GPA1Gi3 chimera

<400> SEQUENCE: 9
atggggtgta cagtgagtac gcaaacaata ggagacgaaa gtgatccttt tctacagaac 60
aaaagagcca atgatgtcat cgagcaatcg ttgcagctgg agaaacaacg tgacaagaat 120
gaaataaaac tgttactatt aggtgccggt gagtcaggta aatcaacggt tttaaaacaa 180
ttaaaattat tacatcaagg cggtttctcc catcaagaaa ggttacagta tgctcaagtg 240
atatgggcag atgccataca atcaatgaaa attttgatta ttcaggccag aaaactaggt 300
attcaacttg actgtgatga tccgatcaac aataaagatt tgtttgcatg caagagaata 360
ctgctaaagg ctaaagcttt agattatatc aacgccagtg ttgccggtgg ttctgatttt 420
ctaaatgatt atgtactgaa gtactcagaa aggtatgaaa ctaggaggcg tgttcagagt 480
accggacgag caaaagctgc tttcgatgaa gacggaaata tttctaatgt caaaagtgac 540
actgacagag atgctgaaac ggtgacgcaa aatgaggatg ctgatagaaa caacagtagt 600
agaattaacc tacaggatat ttgcaaggac ttgaaccaag aaggcgatga ccagatgttt 660
gttagaaaaa catcaaggga aattcaagga caaaatagac gaaatcttat tcacgaagac 720
attgctaagg caataaagca actttggaat aacgacaaag gtataaagca gtgttttgca 780
cgttctaatg agtttcaatt ggagggctca gctgcatact actttgataa cattgagaaa 840
tttgctagtc cgaattatgt ctgtacggat gaagacattt tgaagggccg tataaagact 900
acaggcatta cagaaaccga atttaacatc ggctcgtcca aattcaaggt tctcgacgct 960
ggtgggcagc gttctgaacg taagaagtgg attcattgtt tcgaaggaat tacagcagtt 1020
ttatttgttt tagcaatgag tgaatacgac cagatgttgt ttgaggatga aagagtgaac 1080
agaatgcatg aatcaataat gctatttgac acgttattga actctaagtg gttcaaagat 1140
acaccgttta ttttgttttt aaataaaatt gatttgttcg aggaaaaggt aaaaagcatg 1200
cccataagaa agtactttcc tgattaccag ggacgtgtcg gcgatgcaga agcgggtcta 1260
aaatattttg agaagatatt tttgagcttg aataagacaa acaaaccaat ctacgtgaaa 1320
cgaacctgcg ctaccgatac ccaaactatg aagttcgtat tgagtgcagt caccgatcta 1380
atcatccagc aaaaccttaa agaatgtggt ctatattga 1419

<210> SEQ ID NO 10
<211> LENGTH: 741
<212> TYPE: DNA
<213> ORGANISM: Artificial Sequence
<220> FEATURE:
<223> OTHER INFORMATION: mIL-10_N8S codon optimized with secretion signal

<400> SEQUENCE: 10
atgagattcc catcaatctt caccgcagtt cttttcgcag cctcttccgc actcgcagcc 60
cctgtgaata caacaacaga agatgaaact gctcaaatcc cagctgaagc agtcattggc 120
tacttagatt tggaggggga tttcgatgtt gcagttctac ctttctcaaa ttcaacaaac 180
aatggattgc tgttcataaa cactaccatc gctagcattg cagctaagga ggagggtgtg 240
tcattagata agagagaggc tgaagctcaa tacagtagag aagataactc ctgcactcat 300
tttccagtcg gtcaatctca tatgcttcta gaattgagaa cagcgttttc acaagtaaag 360

```
acattctttc agactaaaga ccaattggat aacattttac tcactgattc tttgatgcaa    420

gacttcaaag gctacttggg ttgtcaggct ttatccgaga tgatccaatt ctacttggta    480

gaagtcatgc cacaggctga aaaacacgga cctgagatta aggaacacct taactcttta    540

ggtgaaaagt tgaaaacact acgtatgaga cttagaagat gccatagatt tctgccatgt    600

gagaacaagt ctaaagccgt tgaacaagtt aagagtgatt tcaacaagtt acaagaccag    660

ggtgtttata aggccatgaa tgaatttgac attttcataa actgtattga agcctacatg    720

atgatcaaga tgaaatctta g                                              741


<210> SEQ ID NO 11
<211> LENGTH: 246
<212> TYPE: PRT
<213> ORGANISM: Artificial Sequence
<220> FEATURE:
<223> OTHER INFORMATION: mIL-10_N8S codon optimized with secretion
      signal

<400> SEQUENCE: 11

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Gln Tyr Ser Arg Glu Asp Asn
                85                  90                  95

Ser Cys Thr His Phe Pro Val Gly Gln Ser His Met Leu Leu Glu Leu
            100                 105                 110

Arg Thr Ala Phe Ser Gln Val Lys Thr Phe Phe Gln Thr Lys Asp Gln
        115                 120                 125

Leu Asp Asn Ile Leu Leu Thr Asp Ser Leu Met Gln Asp Phe Lys Gly
    130                 135                 140

Tyr Leu Gly Cys Gln Ala Leu Ser Glu Met Ile Gln Phe Tyr Leu Val
145                 150                 155                 160

Glu Val Met Pro Gln Ala Glu Lys His Gly Pro Glu Ile Lys Glu His
                165                 170                 175

Leu Asn Ser Leu Gly Glu Lys Leu Lys Thr Leu Arg Met Arg Leu Arg
            180                 185                 190

Arg Cys His Arg Phe Leu Pro Cys Glu Asn Lys Ser Lys Ala Val Glu
        195                 200                 205

Gln Val Lys Ser Asp Phe Asn Lys Leu Gln Asp Gln Gly Val Tyr Lys
    210                 215                 220

Ala Met Asn Glu Phe Asp Ile Phe Ile Asn Cys Ile Glu Ala Tyr Met
225                 230                 235                 240

Met Ile Lys Met Lys Ser
                245


<210> SEQ ID NO 12
<211> LENGTH: 1134
<212> TYPE: DNA
<213> ORGANISM: Artificial Sequence
<220> FEATURE:
```

<223> OTHER INFORMATION: P2Y2 codon optimized DNA

<400> SEQUENCE: 12

```
atggcagctg atttgggacc ttggaacgat acaattaacg gtacttggga tggtgatgaa     60
ctaggttaca gatgcagatt caatgaggac ttcaagtacg ttctactccc agtatcttac    120
ggcgttgtgt gtgtcctggg actttgtcta aacgctgtag ctttgtatat cttcttatgc    180
agattgaaaa catggaacgc tagcacaaca tacatgttcc acttggctgt atcagatgct    240
ctttacgcag cttcacttcc actcttggtt tactactacg ccagaggtga tcattggcct    300
ttttcaacag ttttatgtaa gttggtgaga tttttgttct ataccaactt gtattgctct    360
attttgtttc tgacatgtat ctccgtccat agatgtttgg gtgtcctcag accacttaga    420
tcacttagat gggggagagc tagatacgca agacgtgtcg ctggggcagt ttgggtacta    480
gttctagcct gccaagcccc tgttctttac ttcgtcacta caagtgcaag aggaggcaga    540
gttacctgtc acgacacatc agcgccagaa ctattctcta gatttgttgc atactcctca    600
gtgatgctcg gcttgttgtt tgctgttcct ttcgccgtca ttcttgtctg ctacgtactg    660
atggcaagac gtttattgaa accagcctac ggaacttctg gtggcttacc tagagcaaag    720
agaaagagtg ttagaaccat cgcagtcgtt ctggcagtgt tcgccttatg tttcttacca    780
tttcatgtta ctagaacact gtactactct ttcagaagct tggacttatc atgtcatact    840
ttgaatgcta tcaatatggc ttataaggtt acaagaccac ttgcgtccgc aaattcatgc    900
ttagaccctg tgttatactt tttagccggt caaagattag tgagattcgc tagagatgcc    960
aagccaccaa ctggtccttc tccagcaaca ccagcacgta gacgtttggg gttgagaaga   1020
tctgatagaa ctgatatgca gagaatagag gatgttttag gttcttccga agattctcgt   1080
agaaccgaat ctactccagc gggtagtgaa aacaccaaag acattagact atga         1134
```

<210> SEQ ID NO 13
<211> LENGTH: 377
<212> TYPE: PRT
<213> ORGANISM: Homo sapiens

<400> SEQUENCE: 13

```
Met Ala Ala Asp Leu Gly Pro Trp Asn Asp Thr Ile Asn Gly Thr Trp
1               5                   10                  15

Asp Gly Asp Glu Leu Gly Tyr Arg Cys Arg Phe Asn Glu Asp Phe Lys
            20                  25                  30

Tyr Val Leu Leu Pro Val Ser Tyr Gly Val Val Cys Val Pro Gly Leu
        35                  40                  45

Cys Leu Asn Ala Val Ala Leu Tyr Ile Phe Leu Cys Arg Leu Lys Thr
    50                  55                  60

Trp Asn Ala Ser Thr Thr Tyr Met Phe His Leu Ala Val Ser Asp Ala
65                  70                  75                  80

Leu Tyr Ala Ala Ser Leu Pro Leu Leu Val Tyr Tyr Tyr Ala Arg Gly
                85                  90                  95

Asp His Trp Pro Phe Ser Thr Val Leu Cys Lys Leu Val Arg Phe Leu
            100                 105                 110

Phe Tyr Thr Asn Leu Tyr Cys Ser Ile Leu Phe Leu Thr Cys Ile Ser
        115                 120                 125

Val His Arg Cys Leu Gly Val Leu Arg Pro Leu Arg Ser Leu Arg Trp
    130                 135                 140

Gly Arg Ala Arg Tyr Ala Arg Arg Val Ala Gly Ala Val Trp Val Leu
145                 150                 155                 160
```

```
Val Leu Ala Cys Gln Ala Pro Val Leu Tyr Phe Val Thr Thr Ser Ala
                165                 170                 175

Arg Gly Gly Arg Val Thr Cys His Asp Thr Ser Ala Pro Glu Leu Phe
            180                 185                 190

Ser Arg Phe Val Ala Tyr Ser Ser Val Met Leu Gly Leu Leu Phe Ala
        195                 200                 205

Val Pro Phe Ala Val Ile Leu Val Cys Tyr Val Leu Met Ala Arg Arg
    210                 215                 220

Leu Leu Lys Pro Ala Tyr Gly Thr Ser Gly Gly Leu Pro Arg Ala Lys
225                 230                 235                 240

Arg Lys Ser Val Arg Thr Ile Ala Val Val Leu Ala Val Phe Ala Leu
                245                 250                 255

Cys Phe Leu Pro Phe His Val Thr Arg Thr Leu Tyr Tyr Ser Phe Arg
            260                 265                 270

Ser Leu Asp Leu Ser Cys His Thr Leu Asn Ala Ile Asn Met Ala Tyr
        275                 280                 285

Lys Val Thr Arg Pro Leu Ala Ser Ala Asn Ser Cys Leu Asp Pro Val
    290                 295                 300

Leu Tyr Phe Leu Ala Gly Gln Arg Leu Val Arg Phe Ala Arg Asp Ala
305                 310                 315                 320

Lys Pro Pro Thr Gly Pro Ser Pro Ala Thr Pro Ala Arg Arg Arg Leu
                325                 330                 335

Gly Leu Arg Arg Ser Asp Arg Thr Asp Met Gln Arg Ile Glu Asp Val
            340                 345                 350

Leu Gly Ser Ser Glu Asp Ser Arg Arg Thr Glu Ser Thr Pro Ala Gly
        355                 360                 365

Ser Glu Asn Thr Lys Asp Ile Arg Leu
    370                 375
```

<210> SEQ ID NO 14
<211> LENGTH: 1636
<212> TYPE: DNA
<213> ORGANISM: Artificial Sequence
<220> FEATURE:
<223> OTHER INFORMATION: pFUS1

<400> SEQUENCE: 14

```
aatctcagag gctgagtctc atttttctca aggaaaccat gcagaagctg ttgcgaagtt      60

gacatccgca gctcagtcga accccaatga cgagcaaatg tcaactattg aatcattaat     120

tcaaaaaatc gcaggatacg tcatggacaa ccgtagtggt ggtagtgacg cctcgcaaga     180

tcgtgctgct ggtggtggtt catcttttat gaacacttta atggcagact ctaagggttc     240

ttcccaaacg caactaggaa aactagcttt gttagccaca gtgatgacac actcatcaaa     300

taaaggttct tctaacagag ggtttgacgt agggactgtc atgtcaatgc taagtggttc     360

tggcggcggg agccaaagta tgggtgcttc cggcctggct gccttggctt ctcaattctt     420

taagtcaggt aacaattccc aaggtcaggg acaaggtcaa ggtcaaggtc aaggtcaagg     480

acaaggtcaa ggtcaaggtt cttttactgc tttggcgtct ttggcttcat ctttcatgaa     540

ttccaacaac aataatcagc aaggtcaaaa tcaaagctcc ggtggttcct cctttggagc     600

actggcttct atggcaagct cttttatgca ttccaataat aatcagaact ccaacaatag     660

tcaacagggc tataaccaat cctatcaaaa cggtaaccaa aatagtcaag gttacaataa     720

tcaacagtac caaggtggca acggtggtta ccaacaacaa cagggacaat ctggtggtgc     780
```

-continued tttttcctca ttggcctcca tggctcaatc ttacttaggt ggtggacaaa ctcaatccaa 840
ccaacagcaa tacaatcaac aaggccaaaa caaccagcag caataccagc aacaaggcca 900
aaactatcag catcaacaac agggtcagca gcagcaacaa ggccactcca gttcattctc 960
agctttggct tccatggcaa gttcctacct gggcaataac tccaattcaa attcgagtta 1020
tgggggccag caacaggcta atgagtatgg tagaccgcaa cagaatggtc aacagcaatc 1080
caatgagtac ggaagaccgc aatacggcgg aaaccagaac tccaatggac agcacgaatc 1140
cttcaatttt tctggcaact tttctcaaca gaacaataac ggcaaccaga accgctactg 1200
aacgatgatt cagttcgcct tctatccttt gtttacgtat ttgtttatat atataacttt 1260
attttttttt attaattggg ctgcaagaca attttgttgt cagtgatgcc tcaatccttc 1320
ttttgcttcc atatttacca tgtggaccct ttcaaaacag agttgtatct ctgcaggatg 1380 cccttttttga cgtattgaat ggcataattg cactgtcact tttcgcgctg tctcattttg 1440
gtgcgatgat gaaacaaaca tgaaacgtct gtaatttgaa acaaataacg taattctcgg 1500
gattggtttt atttaaatga caatgtaaga gtggctttgt aaggtatgtg ttgctcttaa 1560
aatatttgga tacgacatcc tttatctttt ttcctttaag agcaggatat aagccatcaa 1620
gtttctgaaa atcaaa 1636

<210> SEQ ID NO 15
<211> LENGTH: 1533
<212> TYPE: DNA
<213> ORGANISM: Homo sapiens

<400> SEQUENCE: 15
atggaagata caaaggagtc taacgtgaag acattttgct ccaagaatat cctagccatc 60
cttggcttct cctctatcat agctgtgata gctttgcttg ctgtggggtt gacccagaac 120
aaagcattgc cagaaaacgt taagtatggg attgtgctgg atgcgggttc ttctcacaca 180
agtttataca tctataagtg gccagcagaa aaggagaatg acacaggcgt ggtgcatcaa 240
gtagaagaat gcagggttaa aggtcctgga atctcaaaat ttgttcagaa agtaaatgaa 300
ataggcattt acctgactga ttgcatggaa agagctaggg aagtgattcc aaggtcccag 360
caccaagaga cacccgttta cctgggagcc acggcaggca tgcggttgct caggatggaa 420
agtgaagagt tggcagacag ggttctggat gtggtggaga ggagcctcag caactacccc 480
tttgacttcc agggtgccag gatcattact ggccaagagg aaggtgccta tggctggatt 540
actatcaact atctgctggg caaattcagt cagaaaacaa ggtggttcag catagtccca 600
tatgaaacca ataatcagga aacctttgga gctttggacc ttgggggagc ctctacacaa 660
gtcacttttg taccccaaaa ccagactatc gagtccccag ataatgctct gcaatttcgc 720
ctctatggca aggactacaa tgtctacaca catagcttct tgtgctatgg gaaggatcag 780
gcactctggc agaaactggc caaggacatt caggttgcaa gtaatgaaat tctcagggac 840
ccatgctttc atcctggata taagaaggta gtgaacgtaa gtgaccttta caagaccccc 900
tgcaccaaga gatttgagat gactcttcca ttccagcagt ttgaaatcca gggtattgga 960
aactatcaac aatgccatca aagcatcctg gagctcttca acaccagtta ctgcccttac 1020
tcccagtgtg ccttcaatgg gattttcttg ccaccactcc agggggattt tggggcattt 1080
tcagcttttt actttgtgat gaagttttta aacttgacat cagagaaagt ctctcaggaa 1140
aaggtgactg agatgatgaa aaagttctgt gctcagcctt gggaggagat aaaaaacatct 1200 tacgctggag taaaggagaa gtacctgagt gaatactgct tttctggtac ctacattctc 1260

```
tccctccttc tgcaaggcta tcatttcaca gctgattcct gggagcacat ccatttcatt   1320

ggcaagatcc agggcagcga cgccggctgg actttgggct acatgctgaa cctgaccaac   1380

atgatcccag ctgagcaacc attgtccaca cctctctccc actccaccta tgtcttcctc   1440

atggttctat tctccctggt ccttttcaca gtggccatca taggcttgct tatctttcac   1500

aagccttcat atttctggaa agatatggta tag                                1533
```

<210> SEQ ID NO 16
<211> LENGTH: 1365
<212> TYPE: DNA
<213> ORGANISM: Solanum tuberosum

<400> SEQUENCE: 16

```
atgttgaacc aaaatagtca ttttattttc ataattttgg caatattttt ggttttgccc     60

ctaagtttat tatccaaaaa tgtgaatgcc caaattccat tgagaagaca tttattaagt    120

catgaatcag aacattatgc agtaatattt gatgctggaa gtactggaag tagagttcat    180

gtttttcgat ttgatgaaaa attaggactt cttcctattg gcaacaatat tgagtatttt    240

atggcgacag agccaggttt aagttcatat gcagaagatc caaaggctgc tgccaattca    300

cttgagccac ttttagatgg agctgaagga gttgttcctc aagaattgca atctgaaaca    360

cctttagaac ttggggcaac agcaggtctt aggatgttaa aaggggatgc agctgaaaaa    420

attctacaag cagtgagaaa tttagtgaag aatcaaagca ctttccatag caaagatcaa    480

tgggtcacta ttcttgatgg aactcaagaa ggctcttata tgtgggctgc aataaattat    540

ttattgggaa atttgggcaa agattataaa agtacaacag caacaattga tcttggtggt    600

ggttcagtcc aaatggcata tgctatatca aatgaacaat ttgcaaaagc tcctcaaaat    660

gaggatggag aaccttatgt tcaacaaaaa catcttatgt caaaagatta taatctctat    720

gtacatagtt atttaaacta tgggcaatta gcaggtcgag ctgagatttt caaggcttca    780

agaaatgaaa gtaatccttg tgctttggaa ggatgtgatg ggtattactc atatggagga    840

gtggactaca aagtaaaagc accaaagaaa ggtagtagtt ggaagagatg caggaggtta    900

actagacatg cacttaaaat aaatgcaaaa tgcaatattg aagaatgcac cttcaatgga    960

gtgtggaatg gtggtggtgg tgatggacaa aaaaatattc atgcttcatc atttttttat   1020

gatattggtg ctcaggttgg cattgttgac accaaatttc catctgctct agcaaagcca   1080

attcaatact taaatgcagc taaagttgct tgccaaacaa atgtggcaga tataaaatcc   1140

atattcccaa aaactcaaga tagaaatatc ccatacttat gtatggactt gatatatgag   1200

tacactttgc ttgttgatgg atttggacta aatccacaca aagaaataac agtgatacat   1260

gatgtgcaat acaaaaacta tctagttgga gcagcatggc cattgggatg tgccattgac   1320

ttggtttctt caactacaaa caaaattaga gttgcatcat cttaa                   1365
```

<210> SEQ ID NO 17
<211> LENGTH: 1311
<212> TYPE: DNA
<213> ORGANISM: Triticum urartu

<400> SEQUENCE: 17

```
atggctcacc tggtgggcat gatggcgctt ctcctcctcc tcctcgcctc gtcagctgag     60

atagcccagg cgcgcgcggc agcggtgccg ccggtgggga agtacgccgt gatcttggac    120

gccggcagca cggggacccg tatgcacgtc ttccggtttg acaagcggat ggatctcgtc    180
```

```
aagatcggcg acgacatcga ggtcttcgcc aaggtgaatc ctggtctgag ttcatactct    240

ggacggccca aggaggctac cgagtccata ttaccactgc ttcaaaaggc caacagcgtc    300

gtgcctcaga ggcttatgaa aacgactcct gttaaactcg gggcgacggc cggactcagg    360

ctcatcggag ataagcaagc aaagcagata cttgacgcgg tcaggggcgc tgtccacact    420

aacaccaagt ttcagtacaa tcccaagtgg atcaatgttc tcgagggatc tcaggaagga    480

tcctacctat gggttgctct gaattacctg ctggataact tgggtgggga ctactcgaaa    540

acggtaggtg tgattgatct tggaggtggg tccgtgcaaa tggcatatgc catttctccg    600

gccaccgttg ttgccgctcc aggagtgcct cacggcaagg atccttatgt tacaaaagag    660

tatctcaagg gaagagatta caacatttat gttcacagct acttacgcta cggcgcctta    720

gcttctcgcg tagagatctt caaggctaag gaaggaccat ttagctactg catgcttcgt    780

ggcttcagtg gcaaatacac ctacaacggt gaggagtaca atgctaccgc gtcaacggga    840

ggtgcacaat acgggaagtg cagaggtgat gtaatgaagg cactcaaact tgatgctcct    900

tgccaagcca agaagtgcac cttcgacggc gtgtggaacg gcgggggcgg ccccggccag    960

gccaacctct atgtcgcatc tagcttctac tacatggcct cgcaggttgg cctcatcgac   1020

agtgatgcac caagcgggac gtccacccca atggctttca gagccgttgc ccagaagata   1080

tgtagaatga gcttgaaaga agtgaaggct aagtacccca aggtccgcga cataccctac   1140

atttgcatgg acctcgtcta tcaatactcc ttgctcgtcg atgggtttgg tttggaaccc   1200

accaagaata ttacactcgt ggagaaggtg aagcatgggg agtacttcat tgaagcggca   1260

tggcctctcg gagaagctat tgaggccgtg gcacccaaaa aggggacttg a             1311
```

```
<210> SEQ ID NO 18
<211> LENGTH: 5
<212> TYPE: PRT
<213> ORGANISM: Artificial Sequence
<220> FEATURE:
<223> OTHER INFORMATION: G protein motif
<220> FEATURE:
<221> NAME/KEY: misc_feature
<222> LOCATION: (1)..(1)
<223> OTHER INFORMATION: Xaa can be aspartic acid or asparagine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 18

Xaa Pro Xaa Xaa Tyr
1               5


<210> SEQ ID NO 19
<211> LENGTH: 510
<212> TYPE: PRT
<213> ORGANISM: Homo sapiens

<400> SEQUENCE: 19

Met Glu Asp Thr Lys Glu Ser Asn Val Lys Thr Phe Cys Ser Lys Asn
1               5                   10                  15

Ile Leu Ala Ile Leu Gly Phe Ser Ser Ile Ile Ala Val Ile Ala Leu
            20                  25                  30

Leu Ala Val Gly Leu Thr Gln Asn Lys Ala Leu Pro Glu Asn Val Lys
        35                  40                  45
```

```
Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
        275                 280                 285

Lys Val Val Asn Val Ser Asp Leu Tyr Lys Thr Pro Cys Thr Lys Arg
    290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
        355                 360                 365

Phe Leu Asn Leu Thr Ser Glu Lys Val Ser Gln Glu Lys Val Thr Glu
    370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
            420                 425                 430

Ser Trp Glu His Ile His Phe Ile Gly Lys Ile Gln Gly Ser Asp Ala
        435                 440                 445

Gly Trp Thr Leu Gly Tyr Met Leu Asn Leu Thr Asn Met Ile Pro Ala
    450                 455                 460
```

```
Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
            500                 505                 510


<210> SEQ ID NO 20
<211> LENGTH: 454
<212> TYPE: PRT
<213> ORGANISM: Solanum tuberosum

<400> SEQUENCE: 20

Met Leu Asn Gln Asn Ser His Phe Ile Phe Ile Ile Leu Ala Ile Phe
1               5                   10                  15

Leu Val Leu Pro Leu Ser Leu Leu Ser Lys Asn Val Asn Ala Gln Ile
            20                  25                  30

Pro Leu Arg Arg His Leu Leu Ser His Glu Ser Glu His Tyr Ala Val
        35                  40                  45

Ile Phe Asp Ala Gly Ser Thr Gly Ser Arg Val His Val Phe Arg Phe
    50                  55                  60

Asp Glu Lys Leu Gly Leu Leu Pro Ile Gly Asn Asn Ile Glu Tyr Phe
65                  70                  75                  80

Met Ala Thr Glu Pro Gly Leu Ser Ser Tyr Ala Glu Asp Pro Lys Ala
                85                  90                  95

Ala Ala Asn Ser Leu Glu Pro Leu Leu Asp Gly Ala Glu Gly Val Val
            100                 105                 110

Pro Gln Glu Leu Gln Ser Glu Thr Pro Leu Glu Leu Gly Ala Thr Ala
        115                 120                 125

Gly Leu Arg Met Leu Lys Gly Asp Ala Ala Glu Lys Ile Leu Gln Ala
    130                 135                 140

Val Arg Asn Leu Val Lys Asn Gln Ser Thr Phe His Ser Lys Asp Gln
145                 150                 155                 160

Trp Val Thr Ile Leu Asp Gly Thr Gln Glu Gly Ser Tyr Met Trp Ala
                165                 170                 175

Ala Ile Asn Tyr Leu Leu Gly Asn Leu Gly Lys Asp Tyr Lys Ser Thr
            180                 185                 190

Thr Ala Thr Ile Asp Leu Gly Gly Gly Ser Val Gln Met Ala Tyr Ala
        195                 200                 205

Ile Ser Asn Glu Gln Phe Ala Lys Ala Pro Gln Asn Glu Asp Gly Glu
    210                 215                 220

Pro Tyr Val Gln Gln Lys His Leu Met Ser Lys Asp Tyr Asn Leu Tyr
225                 230                 235                 240

Val His Ser Tyr Leu Asn Tyr Gly Gln Leu Ala Gly Arg Ala Glu Ile
                245                 250                 255

Phe Lys Ala Ser Arg Asn Glu Ser Asn Pro Cys Ala Leu Glu Gly Cys
            260                 265                 270

Asp Gly Tyr Tyr Ser Tyr Gly Gly Val Asp Tyr Lys Val Lys Ala Pro
        275                 280                 285

Lys Lys Gly Ser Ser Trp Lys Arg Cys Arg Arg Leu Thr Arg His Ala
    290                 295                 300

Leu Lys Ile Asn Ala Lys Cys Asn Ile Glu Glu Cys Thr Phe Asn Gly
305                 310                 315                 320

Val Trp Asn Gly Gly Gly Gly Asp Gly Gln Lys Asn Ile His Ala Ser
                325                 330                 335
```

```
Ser Phe Phe Tyr Asp Ile Gly Ala Gln Val Gly Ile Val Asp Thr Lys
            340                 345                 350

Phe Pro Ser Ala Leu Ala Lys Pro Ile Gln Tyr Leu Asn Ala Ala Lys
        355                 360                 365

Val Ala Cys Gln Thr Asn Val Ala Asp Ile Lys Ser Ile Phe Pro Lys
    370                 375                 380

Thr Gln Asp Arg Asn Ile Pro Tyr Leu Cys Met Asp Leu Ile Tyr Glu
385                 390                 395                 400

Tyr Thr Leu Leu Val Asp Gly Phe Gly Leu Asn Pro His Lys Glu Ile
                405                 410                 415

Thr Val Ile His Asp Val Gln Tyr Lys Asn Tyr Leu Val Gly Ala Ala
            420                 425                 430

Trp Pro Leu Gly Cys Ala Ile Asp Leu Val Ser Ser Thr Thr Asn Lys
        435                 440                 445

Ile Arg Val Ala Ser Ser
    450


<210> SEQ ID NO 21
<211> LENGTH: 436
<212> TYPE: PRT
<213> ORGANISM: Triticum urartu

<400> SEQUENCE: 21

Met Ala His Leu Val Gly Met Met Ala Leu Leu Leu Leu Leu Leu Ala
1               5                   10                  15

Ser Ser Ala Glu Ile Ala Gln Ala Arg Ala Ala Ala Val Pro Pro Val
            20                  25                  30

Gly Lys Tyr Ala Val Ile Leu Asp Ala Gly Ser Thr Gly Thr Arg Met
        35                  40                  45

His Val Phe Arg Phe Asp Lys Arg Met Asp Leu Val Lys Ile Gly Asp
    50                  55                  60

Asp Ile Glu Val Phe Ala Lys Val Asn Pro Gly Leu Ser Ser Tyr Ser
65                  70                  75                  80

Gly Arg Pro Lys Glu Ala Thr Glu Ser Ile Leu Pro Leu Leu Gln Lys
                85                  90                  95

Ala Asn Ser Val Val Pro Gln Arg Leu Met Lys Thr Thr Pro Val Lys
            100                 105                 110

Leu Gly Ala Thr Ala Gly Leu Arg Leu Ile Gly Asp Lys Gln Ala Lys
        115                 120                 125

Gln Ile Leu Asp Ala Val Arg Gly Ala Val His Thr Asn Thr Lys Phe
    130                 135                 140

Gln Tyr Asn Pro Lys Trp Ile Asn Val Leu Glu Gly Ser Gln Glu Gly
145                 150                 155                 160

Ser Tyr Leu Trp Val Ala Leu Asn Tyr Leu Leu Asp Asn Leu Gly Gly
                165                 170                 175

Asp Tyr Ser Lys Thr Val Gly Val Ile Asp Leu Gly Gly Gly Ser Val
            180                 185                 190

Gln Met Ala Tyr Ala Ile Ser Pro Ala Thr Val Val Ala Ala Pro Gly
        195                 200                 205

Val Pro His Gly Lys Asp Pro Tyr Val Thr Lys Glu Tyr Leu Lys Gly
    210                 215                 220

Arg Asp Tyr Asn Ile Tyr Val His Ser Tyr Leu Arg Tyr Gly Ala Leu
225                 230                 235                 240

Ala Ser Arg Val Glu Ile Phe Lys Ala Lys Glu Gly Pro Phe Ser Tyr
```

```
                245                 250                 255

Cys Met Leu Arg Gly Phe Ser Gly Lys Tyr Thr Tyr Asn Gly Glu Glu
            260                 265                 270

Tyr Asn Ala Thr Ala Ser Thr Gly Gly Ala Gln Tyr Gly Lys Cys Arg
        275                 280                 285

Gly Asp Val Met Lys Ala Leu Lys Leu Asp Ala Pro Cys Gln Ala Lys
    290                 295                 300

Lys Cys Thr Phe Asp Gly Val Trp Asn Gly Gly Gly Gly Pro Gly Gln
305                 310                 315                 320

Ala Asn Leu Tyr Val Ala Ser Ser Phe Tyr Tyr Met Ala Ser Gln Val
                325                 330                 335

Gly Leu Ile Asp Ser Asp Ala Pro Ser Gly Thr Ser Thr Pro Met Ala
            340                 345                 350

Phe Arg Ala Val Ala Gln Lys Ile Cys Arg Met Ser Leu Lys Glu Val
        355                 360                 365

Lys Ala Lys Tyr Pro Lys Val Arg Asp Ile Pro Tyr Ile Cys Met Asp
    370                 375                 380

Leu Val Tyr Gln Tyr Ser Leu Leu Val Asp Gly Phe Gly Leu Glu Pro
385                 390                 395                 400

Thr Lys Asn Ile Thr Leu Val Glu Lys Val Lys His Gly Glu Tyr Phe
                405                 410                 415

Ile Glu Ala Ala Trp Pro Leu Gly Glu Ala Ile Glu Ala Val Ala Pro
            420                 425                 430

Lys Lys Gly Thr
        435


<210> SEQ ID NO 22
<211> LENGTH: 455
<212> TYPE: DNA
<213> ORGANISM: Artificial Sequence
<220> FEATURE:
<223> OTHER INFORMATION: pCAS AarI custom multiple cloning site

<400> SEQUENCE: 22

gtatatgtgt tatgtagtat actctttctt caacaattaa atactctcgg tagccaagtt      60

ggtttaaggc gcaagactgt aatttatcac tacgaaatct tgagatcggg cgttcgactc     120

gcccccggga gagatggccg gcatggtccc agcctcctcg ctggcgccgg ctgggcaaca     180

ccttcgggtg gcgaatggga ctttcaaggc aggtggacaa gaggagtgcg gccgcagctg     240

gaactcccac ctgcaacagt tttagagcta gaaatagcaa gttaaaataa ggctagtccg     300

ttatcaactt gaaaaagtgg caccgagtcg gtgctttttt tattttttgt cactattgtt     360

atgtaaaatg ccacctctga cagtatggaa cgcaaacttc tgtctagtgg atataggtct     420

agagatctgt ttagcttgcc tcgtccccgc cgggt                                455


<210> SEQ ID NO 23
<211> LENGTH: 8
<212> TYPE: PRT
<213> ORGANISM: Artificial Sequence
<220> FEATURE:
<223> OTHER INFORMATION: alpha-factor signal peptide

<400> SEQUENCE: 23

Met Arg Phe Pro Ser Ile Phe Thr
1               5


<210> SEQ ID NO 24
```

-continued

```
<211> LENGTH: 16
<212> TYPE: PRT
<213> ORGANISM: Artificial Sequence
<220> FEATURE:
<223> OTHER INFORMATION: alpha-factor signal peptide

<400> SEQUENCE: 24

Glu Gly Val Ser Leu Asp Lys Arg Gln Ile Pro Leu Arg Arg His Leu
1               5                   10                  15


<210> SEQ ID NO 25
<211> LENGTH: 17
<212> TYPE: PRT
<213> ORGANISM: Artificial Sequence
<220> FEATURE:
<223> OTHER INFORMATION: HA tag

<400> SEQUENCE: 25

Asn Lys Ile Arg Val Ala Ser Ser Tyr Pro Tyr Asp Val Pro Asp Tyr
1               5                   10                  15

Ala


<210> SEQ ID NO 26
<211> LENGTH: 16
<212> TYPE: PRT
<213> ORGANISM: Artificial Sequence
<220> FEATURE:
<223> OTHER INFORMATION: alpha-factor signal peptide

<400> SEQUENCE: 26

Glu Gly Val Ser Leu Asp Lys Arg Ala Glu Ile Ala Gln Ala Arg Ala
1               5                   10                  15


<210> SEQ ID NO 27
<211> LENGTH: 17
<212> TYPE: PRT
<213> ORGANISM: Artificial Sequence
<220> FEATURE:
<223> OTHER INFORMATION: HA tag

<400> SEQUENCE: 27

Ala Val Ala Pro Lys Lys Gly Thr Tyr Pro Tyr Asp Val Pro Asp Tyr
1               5                   10                  15

Ala
```